(12) United States Patent
Markowitz et al.

(10) Patent No.: US 8,208,991 B2
(45) Date of Patent: Jun. 26, 2012

(54) DETERMINING A MATERIAL FLOW CHARACTERISTIC IN A STRUCTURE

(75) Inventors: H. Toby Markowitz, Roseville, MN (US); Phillip Falkner, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 676 days.

(21) Appl. No.: 12/422,658

(22) Filed: Apr. 13, 2009

(65) Prior Publication Data

US 2009/0262979 A1    Oct. 22, 2009

Related U.S. Application Data

(63) Continuation of application No. 12/421,364, filed on Apr. 9, 2009, which is a continuation-in-part of application No. 12/117,537, filed on May 8, 2008.

(60) Provisional application No. 61/046,298, filed on Apr. 18, 2008.

(51) Int. Cl.
*A61B 5/05* (2006.01)
(52) U.S. Cl. .......................... 600/424; 600/508
(58) Field of Classification Search .............. 607/6, 116, 607/122, 148; 600/374, 407, 424, 504, 506, 600/526
See application file for complete search history.

(56) References Cited

U.S. PATENT DOCUMENTS

| | | |
|---|---|---|
| 3,837,347 A | 9/1974 | Tower |
| 3,995,623 A | 12/1976 | Blake et al. |
| 4,506,680 A | 3/1985 | Stokes |
| 4,619,246 A | 10/1986 | Molgaard-Nielsen et al. |
| 4,649,924 A | 3/1987 | Taccardi |
| 4,696,304 A | 9/1987 | Chin |
| 4,801,297 A | 1/1989 | Mueller |
| 5,035,246 A | 7/1991 | Heuvelmans et al. |
| 5,076,285 A | 12/1991 | Hess et al. |
| 5,078,714 A | 1/1992 | Katims |
| 5,099,845 A | 3/1992 | Besz et al. |
| 5,167,239 A | 12/1992 | Cohen et al. |
| 5,255,680 A | 10/1993 | Darrow et al. |

(Continued)

FOREIGN PATENT DOCUMENTS

EP    363117    4/1990

(Continued)

OTHER PUBLICATIONS

Birkfellner, Wolfgang, et al. "Calibration of Tracking Systems in a Surgical Environment," IEEE Transactions on Medical Imaginge, IEEE Service Center, Piscataway, NJ, US, vol. 17, No. 5. (Oct. 1, 1998) XP011035767. ISSN: 0278-0062 the whole document.

(Continued)

*Primary Examiner* — Carl H Layno
*Assistant Examiner* — Jeremiah Kimball
(74) *Attorney, Agent, or Firm* — Harness, Dickey

(57) ABSTRACT

An volume of a patient can be mapped with a system operable to identify a plurality of locations and save a plurality of locations of a mapping instrument. The mapping instrument can include one or more electrodes that can sense a voltage that can be correlated to a three dimensional location of the electrode at the time of the sensing or measurement. Therefore, a map of a volume can be determined based upon the sensing of the plurality of points without the use of other imaging devices. An implantable medical device can then be navigated relative to the mapping data.

24 Claims, 38 Drawing Sheets

U.S. PATENT DOCUMENTS

| | | | |
|---|---|---|---|
| 5,265,622 A | 11/1993 | Barbere | |
| 5,297,549 A | 3/1994 | Beatty et al. | |
| 5,342,295 A | 8/1994 | Imran | |
| 5,385,148 A | 1/1995 | Lesh et al. | |
| 5,391,199 A | 2/1995 | Ben-Haim | |
| 5,443,489 A | 8/1995 | Ben-Haim | |
| 5,480,422 A | 1/1996 | Ben-Haim | |
| 5,512,920 A | 4/1996 | Gibson | |
| 5,522,874 A | 6/1996 | Gates | |
| 5,546,951 A | 8/1996 | Ben-Haim | |
| 5,558,091 A | 9/1996 | Acker et al. | |
| 5,568,809 A | 10/1996 | Ben-haim | |
| 5,639,276 A | 6/1997 | Weinstock et al. | |
| 5,697,377 A | 12/1997 | Wittkampf | |
| 5,713,946 A | 2/1998 | Ben-Haim | |
| 5,797,849 A | 8/1998 | Vesely et al. | |
| 5,800,407 A | 9/1998 | Eldor et al. | |
| 5,840,025 A | 11/1998 | Ben-Haim | |
| 5,916,193 A | 6/1999 | Stevens et al. | |
| 5,944,022 A | 8/1999 | Nardella et al. | |
| 5,983,126 A | 11/1999 | Wittkampf | |
| 6,009,349 A | 12/1999 | Mouchawar et al. | |
| 6,050,267 A | 4/2000 | Nardella et al. | |
| 6,088,527 A | 7/2000 | Rybczynski | |
| 6,090,105 A * | 7/2000 | Zepeda et al. | 606/41 |
| 6,122,552 A | 9/2000 | Tockman et al. | |
| 6,152,946 A | 11/2000 | Broome et al. | |
| 6,196,230 B1 | 3/2001 | Hall et al. | |
| 6,236,886 B1 | 5/2001 | Cherepenin et al. | |
| 6,240,307 B1 * | 5/2001 | Beatty et al. | 600/374 |
| 6,246,468 B1 | 6/2001 | Dimsdale | |
| 6,256,121 B1 | 7/2001 | Lizotte et al. | |
| 6,301,498 B1 | 10/2001 | Greenberg et al. | |
| 6,330,356 B1 | 12/2001 | Sundareswaran et al. | |
| 6,389,187 B1 | 5/2002 | Greenaway et al. | |
| 6,470,205 B2 | 10/2002 | Bosselmann et al. | |
| 6,546,270 B1 | 4/2003 | Goldin et al. | |
| 6,569,160 B1 | 5/2003 | Goldin et al. | |
| 6,574,498 B1 | 6/2003 | Gilboa | |
| 6,595,989 B1 | 7/2003 | Schaer | |
| 6,602,271 B2 | 8/2003 | Adams et al. | |
| 6,611,141 B1 | 8/2003 | Schulz et al. | |
| 6,701,176 B1 | 3/2004 | Halperin et al. | |
| 6,714,806 B2 * | 3/2004 | Iaizzo et al. | 600/374 |
| 6,771,996 B2 * | 8/2004 | Bowe et al. | 600/374 |
| 6,868,195 B2 | 3/2005 | Fujita et al. | |
| 6,888,623 B2 | 5/2005 | Clements | |
| 6,892,091 B1 | 5/2005 | Ben-Haim et al. | |
| 6,990,370 B1 | 1/2006 | Beatty et al. | |
| 7,020,522 B1 | 3/2006 | Hoijer et al. | |
| 7,047,073 B2 | 5/2006 | Hoijer et al. | |
| 7,189,208 B1 | 3/2007 | Beatty et al. | |
| 7,207,989 B2 | 4/2007 | Pike, Jr. et al. | |
| 7,215,430 B2 | 5/2007 | Kacyra et al. | |
| 7,263,397 B2 | 8/2007 | Hauck et al. | |
| 7,305,121 B2 | 12/2007 | Kaufmann et al. | |
| 7,328,071 B1 * | 2/2008 | Stehr et al. | 607/131 |
| 7,369,901 B1 | 5/2008 | Morgan et al. | |
| 7,421,300 B2 | 9/2008 | Smits et al. | |
| 7,479,141 B2 | 1/2009 | Kleen et al. | |
| 7,529,584 B2 * | 5/2009 | Laske et al. | 607/9 |
| 7,715,604 B2 | 5/2010 | Sun et al. | |
| 7,941,213 B2 | 5/2011 | Markowitz et al. | |
| 7,988,639 B2 | 8/2011 | Starks | |
| 2001/0031920 A1 | 10/2001 | Kaufman et al. | |
| 2002/0045810 A1 * | 4/2002 | Ben-Haim | 600/374 |
| 2002/0049375 A1 | 4/2002 | Strommer et al. | |
| 2002/0077544 A1 | 6/2002 | Shahidi | |
| 2002/0111662 A1 * | 8/2002 | Iaizzo et al. | 607/119 |
| 2002/0147488 A1 | 10/2002 | Doan et al. | |
| 2002/0183817 A1 | 12/2002 | Van Venrooij et al. | |
| 2003/0028118 A1 | 2/2003 | Dupree et al. | |
| 2003/0055324 A1 | 3/2003 | Wasserman | |
| 2003/0078494 A1 | 4/2003 | Panescu et al. | |
| 2003/0108853 A1 | 6/2003 | Chosack et al. | |
| 2003/0114908 A1 | 6/2003 | Flach | |
| 2003/0225434 A1 | 12/2003 | Glantz et al. | |
| 2003/0231789 A1 | 12/2003 | Willis et al. | |
| 2004/0001075 A1 | 1/2004 | Balakrishnan et al. | |
| 2004/0044295 A1 | 3/2004 | Reinert et al. | |
| 2004/0064159 A1 | 4/2004 | Hoijer et al. | |
| 2004/0068312 A1 | 4/2004 | Sigg et al. | |
| 2004/0070582 A1 | 4/2004 | Smith et al. | |
| 2004/0097805 A1 | 5/2004 | Verard et al. | |
| 2004/0162599 A1 | 8/2004 | Kurth | |
| 2004/0215298 A1 | 10/2004 | Richardson et al. | |
| 2004/0228453 A1 | 11/2004 | Dobbs et al. | |
| 2004/0236395 A1 | 11/2004 | Iaizzo et al. | |
| 2004/0249281 A1 | 12/2004 | Olstad | |
| 2004/0249430 A1 | 12/2004 | Martinez et al. | |
| 2004/0254437 A1 * | 12/2004 | Hauck et al. | 600/374 |
| 2005/0004476 A1 | 1/2005 | Payvar et al. | |
| 2005/0018888 A1 | 1/2005 | Zonneveld | |
| 2005/0119550 A1 | 6/2005 | Serra et al. | |
| 2005/0177151 A1 | 8/2005 | Coen et al. | |
| 2005/0187432 A1 | 8/2005 | Hale et al. | |
| 2005/0245803 A1 | 11/2005 | Glenn Jr. et al. | |
| 2006/0013523 A1 | 1/2006 | Childers et al. | |
| 2006/0058604 A1 | 3/2006 | Avinash et al. | |
| 2006/0117773 A1 | 6/2006 | Street et al. | |
| 2006/0135883 A1 | 6/2006 | Jonsson et al. | |
| 2006/0153468 A1 | 7/2006 | Solf et al. | |
| 2006/0173268 A1 | 8/2006 | Mullick et al. | |
| 2006/0200049 A1 | 9/2006 | Leo et al. | |
| 2006/0206157 A1 | 9/2006 | Hoijer | |
| 2006/0229513 A1 | 10/2006 | Wakai | |
| 2006/0229594 A1 | 10/2006 | Francischelli et al. | |
| 2006/0247520 A1 | 11/2006 | McGee | |
| 2007/0016084 A1 | 1/2007 | Denault | |
| 2007/0038052 A1 | 2/2007 | Swoyer et al. | |
| 2007/0043413 A1 | 2/2007 | Eversull et al. | |
| 2007/0046661 A1 | 3/2007 | Ma et al. | |
| 2007/0049817 A1 | 3/2007 | Preiss et al. | |
| 2007/0112388 A1 | 5/2007 | Salo | |
| 2007/0123944 A1 | 5/2007 | Zdeblick | |
| 2007/0135721 A1 | 6/2007 | Zdeblick | |
| 2007/0135803 A1 | 6/2007 | Belson | |
| 2007/0156019 A1 | 7/2007 | Larkin et al. | |
| 2007/0164900 A1 | 7/2007 | Schneider et al. | |
| 2007/0167801 A1 | 7/2007 | Webler et al. | |
| 2007/0252074 A1 | 11/2007 | Ng et al. | |
| 2007/0270682 A1 | 11/2007 | Huang et al. | |
| 2007/0299351 A1 * | 12/2007 | Harlev et al. | 600/509 |
| 2007/0299352 A1 | 12/2007 | Harlev et al. | |
| 2007/0299353 A1 | 12/2007 | Harlev et al. | |
| 2008/0015466 A1 | 1/2008 | Lerman | |
| 2008/0024493 A1 | 1/2008 | Bordoloi et al. | |
| 2008/0038197 A1 | 2/2008 | John et al. | |
| 2008/0058656 A1 | 3/2008 | Costello et al. | |
| 2008/0071142 A1 | 3/2008 | Gattani et al. | |
| 2008/0118117 A1 | 5/2008 | Gauldie et al. | |
| 2008/0132800 A1 | 6/2008 | Hettrick et al. | |
| 2008/0183072 A1 | 7/2008 | Robertson et al. | |
| 2008/0207997 A1 | 8/2008 | Higgins et al. | |
| 2008/0221425 A1 | 9/2008 | Olson et al. | |
| 2008/0221438 A1 | 9/2008 | Chen et al. | |
| 2008/0243025 A1 | 10/2008 | Holmstrom et al. | |
| 2008/0249375 A1 | 10/2008 | Obel | |
| 2009/0017430 A1 | 1/2009 | Muller-Daniels et al. | |
| 2009/0063118 A1 | 3/2009 | Dachille et al. | |
| 2009/0093857 A1 | 4/2009 | Markowitz et al. | |
| 2009/0099619 A1 | 4/2009 | Lessmeier et al. | |
| 2009/0103793 A1 | 4/2009 | Borland et al. | |
| 2009/0126575 A1 | 5/2009 | Son et al. | |
| 2009/0129477 A1 | 5/2009 | Yang | |
| 2009/0131955 A1 | 5/2009 | Wenderow et al. | |
| 2009/0192381 A1 | 7/2009 | Brockway et al. | |
| 2009/0227861 A1 | 9/2009 | Ganatra et al. | |
| 2009/0253976 A1 | 10/2009 | Harlev et al. | |
| 2009/0253985 A1 * | 10/2009 | Shachar et al. | 600/424 |
| 2009/0262109 A1 | 10/2009 | Markowitz et al. | |
| 2009/0262980 A1 | 10/2009 | Markowitz et al. | |
| 2009/0262982 A1 | 10/2009 | Markowitz et al. | |
| 2009/0262992 A1 | 10/2009 | Markowitz et al. | |
| 2009/0264727 A1 | 10/2009 | Markowitz et al. | |
| 2009/0264738 A1 | 10/2009 | Markowitz et al. | |
| 2009/0264739 A1 | 10/2009 | Markowitz et al. | |

| | | | |
|---|---|---|---|
| 2009/0264740 | A1 | 10/2009 | Markowitz et al. |
| 2009/0264741 | A1 | 10/2009 | Markowitz et al. |
| 2009/0264742 | A1 | 10/2009 | Markowitz et al. |
| 2009/0264743 | A1 | 10/2009 | Markowitz et al. |
| 2009/0264744 | A1 | 10/2009 | Markowitz et al. |
| 2009/0264745 | A1 | 10/2009 | Markowitz et al. |
| 2009/0264746 | A1 | 10/2009 | Markowitz et al. |
| 2009/0264747 | A1 | 10/2009 | Markowitz et al. |
| 2009/0264748 | A1 | 10/2009 | Markowitz et al. |
| 2009/0264749 | A1 | 10/2009 | Markowitz et al. |
| 2009/0264750 | A1 | 10/2009 | Markowitz et al. |
| 2009/0264751 | A1 | 10/2009 | Markowitz et al. |
| 2009/0264752 | A1 | 10/2009 | Markowitz et al. |
| 2009/0264777 | A1 | 10/2009 | Markowitz et al. |
| 2009/0264778 | A1 | 10/2009 | Markowitz et al. |
| 2009/0265128 | A1 | 10/2009 | Markowitz et al. |
| 2009/0267773 | A1 | 10/2009 | Markowitz et al. |
| 2009/0297001 | A1 | 12/2009 | Markowitz et al. |
| 2010/0004724 | A1 | 1/2010 | Markowitz et al. |
| 2010/0030298 | A1 | 2/2010 | Martens et al. |
| 2010/0152571 | A1 | 6/2010 | Hartmann et al. |
| 2011/0054304 | A1 | 3/2011 | Markowitz et al. |

FOREIGN PATENT DOCUMENTS

| | | |
|---|---|---|
| EP | 1393674 A1 | 3/2004 |
| EP | 1421913 A1 | 5/2004 |
| EP | 2136706 | 12/2009 |
| WO | WO-9848722 A1 | 11/1998 |
| WO | WO-0134050 A2 | 5/2001 |
| WO | WO-02064040 A2 | 8/2002 |
| WO | WO-2005112836 A2 | 12/2005 |
| WO | WO-2006042039 A2 | 4/2006 |
| WO | WO-2006117773 A1 | 11/2006 |
| WO | WO-2007067945 | 6/2007 |
| WO | WO-2007111542 A1 | 10/2007 |
| WO | WO-2007136451 A2 | 11/2007 |
| WO | WO-2008108901 | 9/2008 |
| WO | WO-2008147961 A1 | 12/2008 |
| WO | WO-2009126575 A1 | 10/2009 |
| WO | WO-2009129477 A1 | 10/2009 |
| WO | WO-2010074986 A1 | 7/2010 |

OTHER PUBLICATIONS

Hubert-Tremblay, Vincent, et al. "Octree indexing of DICOM images for voxel number reduction and improvement of Monte Carolo simulation computing efficiency," Medical Physics, AIP, Melville, NY, US, vol. 33, No. 8, (Jul. 21, 2006) pp. 2819-2831, XP012092212, ISSN: 0094-2405, DOI: 10.1118/1.2214305 pp. 2820-2821.
International Preliminary Report on Patentability mailed Oct. 11, 2011 for PCT/US2010/030534 claming benefit of U.S. Appl. No. 12/421,375, filed Apr. 9, 2009.
International Search Report and Written Opinon mailed Jul. 25, 2011 for PCT/US2010/047241 claiming benefit of U.S. Appl. No. 12/844,065, filed Jul. 27, 2010.
International Search Report mailed Sep. 13, 2010 for PCT/US2010/030534 claming benefit of U.S. Appl. No. 12/421,375, filed Apr. 9, 2009.
Invitation to Pay Additional Fees mailed Jul. 7, 2010 for PCT/US2010/030534 claming benefit of U.S. Appl. No. 12/421,375, filed Apr. 9, 2009.
"EnSite NavX™ Navigation & Visualization Technology." 3 pages, St. Jude Medical. http://www.sjmprofessional.com/Products/US/Mapping-and-Visualization/EnSite-NavX-Navigation-and-Visualization-Technology.aspx Web. Accessed Jun. 19, 2009.
"Local Lisa® Intracardiac Navigation System Model 9670000/9670025." Technical Manual Version 1.2, Chapter 1, pp. 1-19. 2004.
Brenner, David J., Ph.D., "Computed Tomography—An Increasing Source of Radiation Exposure", The New England Journal of Medicine (Nov. 29, 2007), pp. 2277-2284.
Gepstein, Lior, M.D., "A Novel Method for Nonfluoroscopic Catheter-Based Electroanatomical Mapping of the Heart, in Vitro and in Vivo Accuracy Results", American Heart Association, Learn and Live, Circulation (1997), http://circ.ahajournals.org/cgi/content/abstract/95/6/1611 printed Oct. 2, 2008.

International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Preliminary Report on Patentability and Written Opinion for PCT/US2009/0400984 mailed Oct. 28, 2010, claiming benefit of U.S. Appl. No. 12/117,549, filed May 8, 2008.
International Preliminary Report on Patentability and Written Opinion for PCT/US2009/040979 mailed Oct. 28, 2010 claiming benefit of U.S. Appl. No. 12/117,537, filed May 8, 2008.
International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966,382, filed Dec. 28, 2007.
International Search Report and Written Opinion for PCT/US2009/0400984 mailed Sep. 21, 2009, claiming benefit of U.S. Appl. No. 12/117,549, filed May 8, 2008.
International Search Report and Written Opinion for PCT/US2009/040998 mailed Jul. 29, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.
International Search Report and Written Opinion for PCT/US2009/067486 mailed May 4, 2010, claiming benefit of U.S. Appl. No. 12/336,085, filed Dec. 16, 2008.
International Search Report and Written Opinon for PCT/US2009/040979 mailed Sep. 21, 2009 claiming benefit of U.S. Appl. No. 12/117,537, filed May 8, 2008.
Invitation to Pay Additional Fees for PCT/US2009/0400984 mailed Jul. 30, 2009, claiming benefit of U.S. Appl. No. 12/117,549, filed May 8, 2008.
Invitation to Pay Additional Fees for PCT/US2009/040979 mailed Jul. 30, 2009 claiming benefit of U.S. Appl. No. 12/117,537, filed May 8, 2008.
Invitation to Pay Additional Fees for PCT/US2009/067486 mailed Mar. 5, 2010, claiming benefit of U.S. Appl. No. 12/336,085, filed Dec. 16, 2008.
Invitation to Pay Additional Fees mailed Jul. 7, 2010 for PCT/US2010/030534 claiming benefit of U.S. Appl. No. 12/421,375, filed Apr. 9, 2009.
Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.
Markowitz, Toby, et al., "Unleaded: The Fluoroless 3D Lead Implant", Presented at Heart Rhythm Society, Denver, CO, (May 2007) 1 pg.
Markowitz, Toby, et al., Abstract Submission, "Unleaded: The Fluoroless 3D Lead Implant", Mar. 2007 2 pgs.
Milstein, S. et al., "Initial Clinical Results of Non-Fluoroscopic Pacemaker Lead Implantation." (pre-presentation abstract) May 14-17, 2008. 2 pgs.
Milstein, S. et al., "Initial Clinical Results of Non-Fluoroscopic Pacemaker Lead Implantation." (poster presentation) May 14-17, 2008. 1 pg.
Nelder, J.A., et al. "A simplex method for function minimization." vol. 7, Issue 4, (1965) pp. 308-313.The Computer Journal.
Savage, George, M.D., "Electric Tomography (ET)—A Novel Method for Assessing Myocardial Motion and Cardiac Performance", Heart Rhythm Society, Denver, CO (May 9-12, 2007) 1 pg.
Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.
Wittkampf, Fred., H.M., et al. "Accuracy of the LocaLisa System in Catheter Ablation Procedures." Journal of Electrocardiology vol. 32

Supplement (1999). Heart Lung Institute, University Hospital Utrecht, The Netherlands.

International Preliminary Report on Patentability and Written Opinion mailed Oct. 29, 2009 for PCT/US2007/089087 of which U.S. Appl. No. 12/492,906, filed Jun. 26, 2009 claims benefit.

International Search Report and Written Opinion mailed Dec. 6, 2010 for PCT/US2010/051248 which claims benefit of U.S. Appl. No. 12/609,734, filed Oct. 30, 2009.

International Search Report for PCT/US2007/089087 mailed Jul. 9, 2008, of which U.S. Appl. No. 12/492,906, filed Jun. 26, 2009 claims benefit.

Invitation to Pay Additional Fees for PCT/US2010/047241 mailed Jan. 10, 2011, claiming benefit of U.S. Appl. No. 12/844,065, filed Jul. 27, 2010.

* cited by examiner

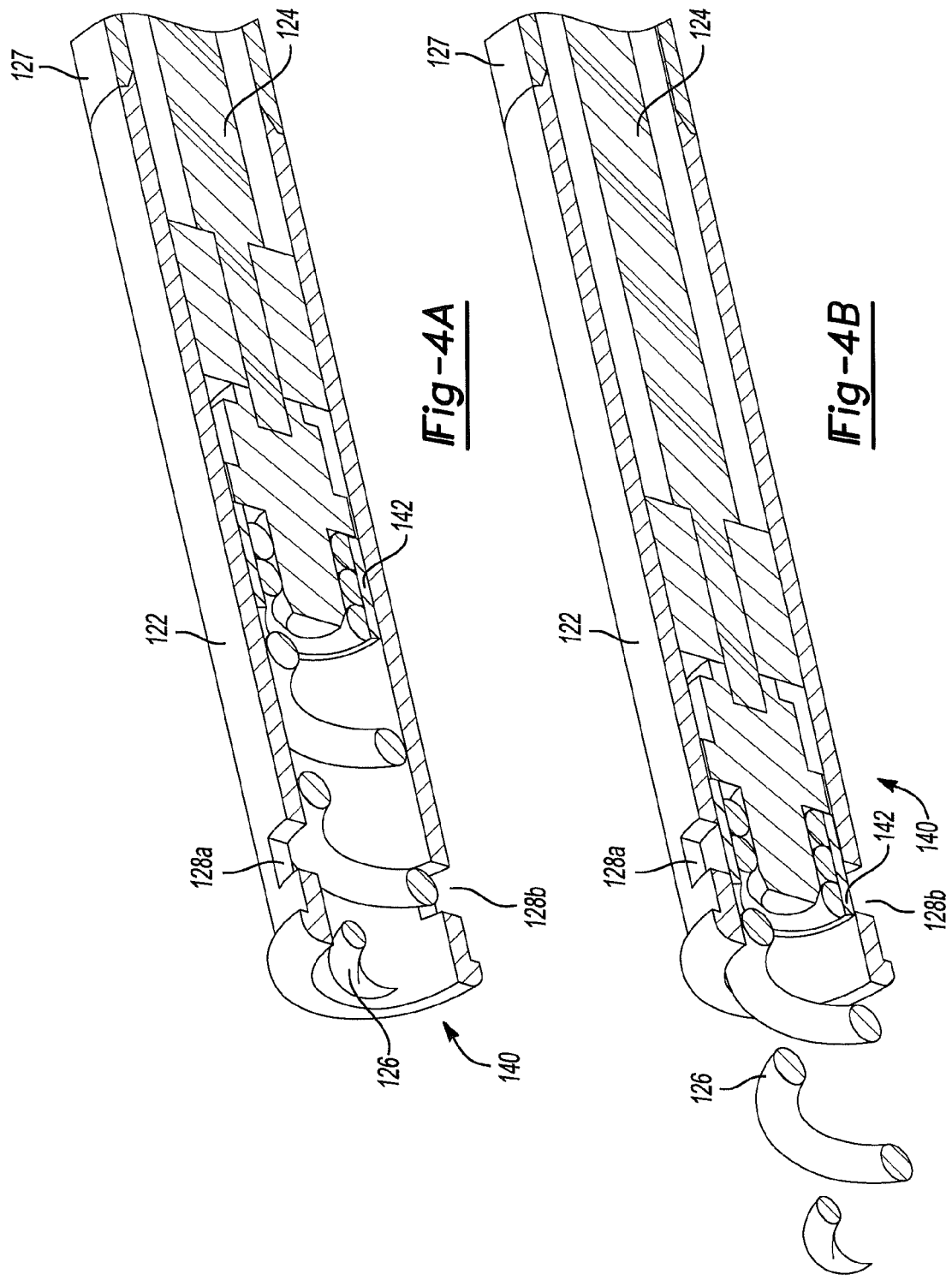

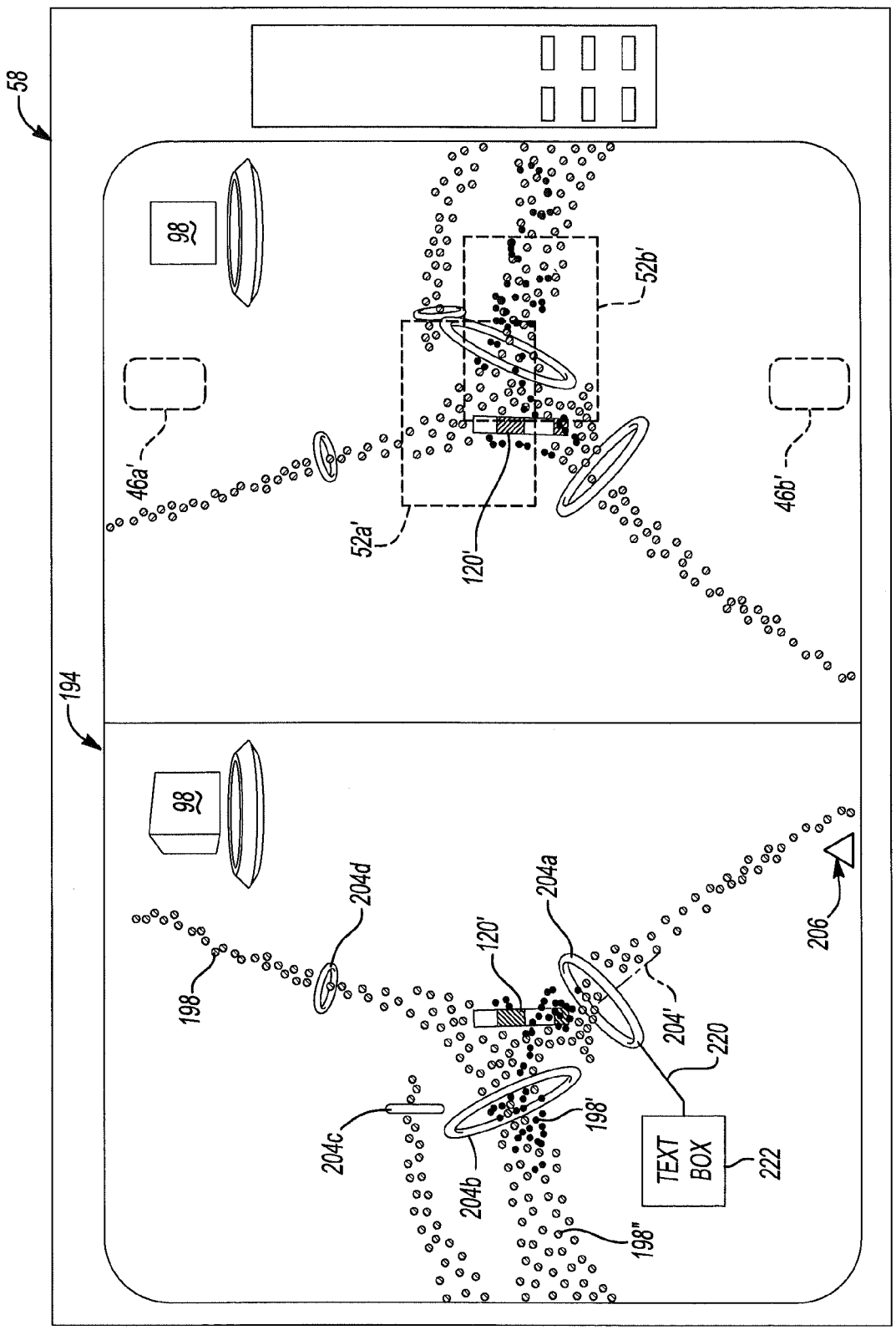

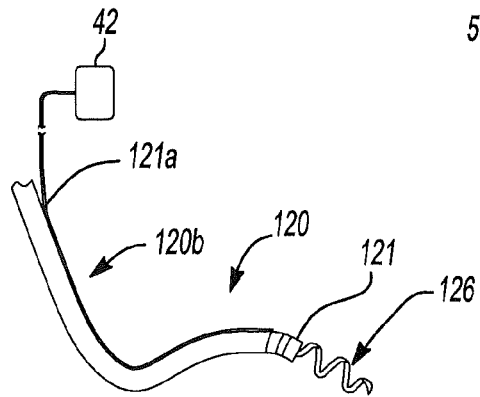
Fig-12Ai
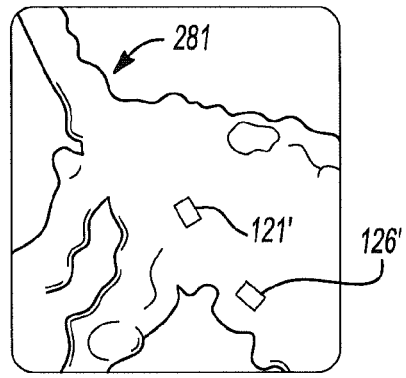
Fig-12Aii
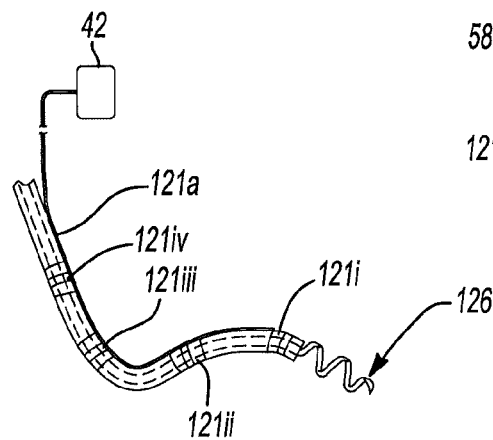
Fig-12Bi
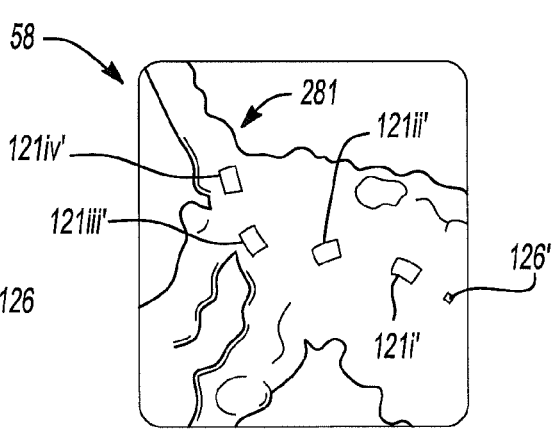
Fig-12Bii
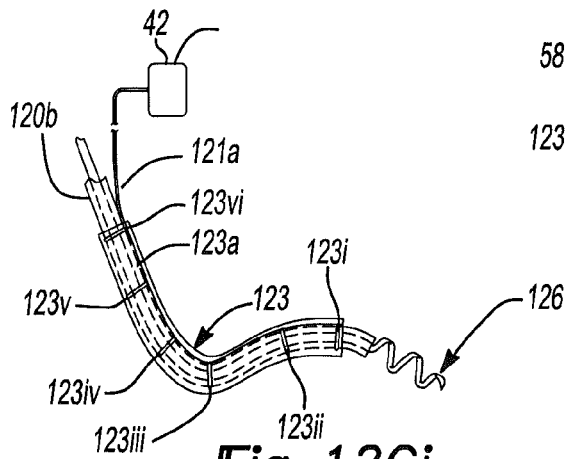
Fig-12Ci
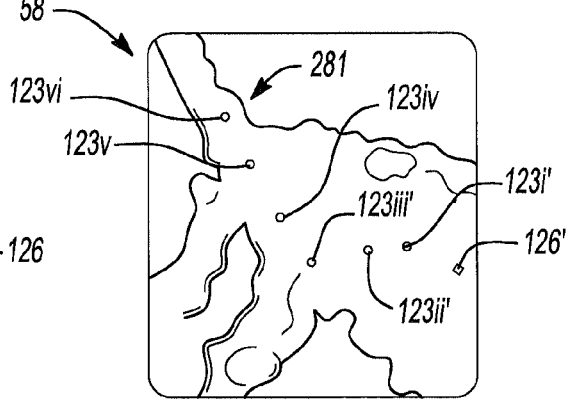
Fig-12Cii

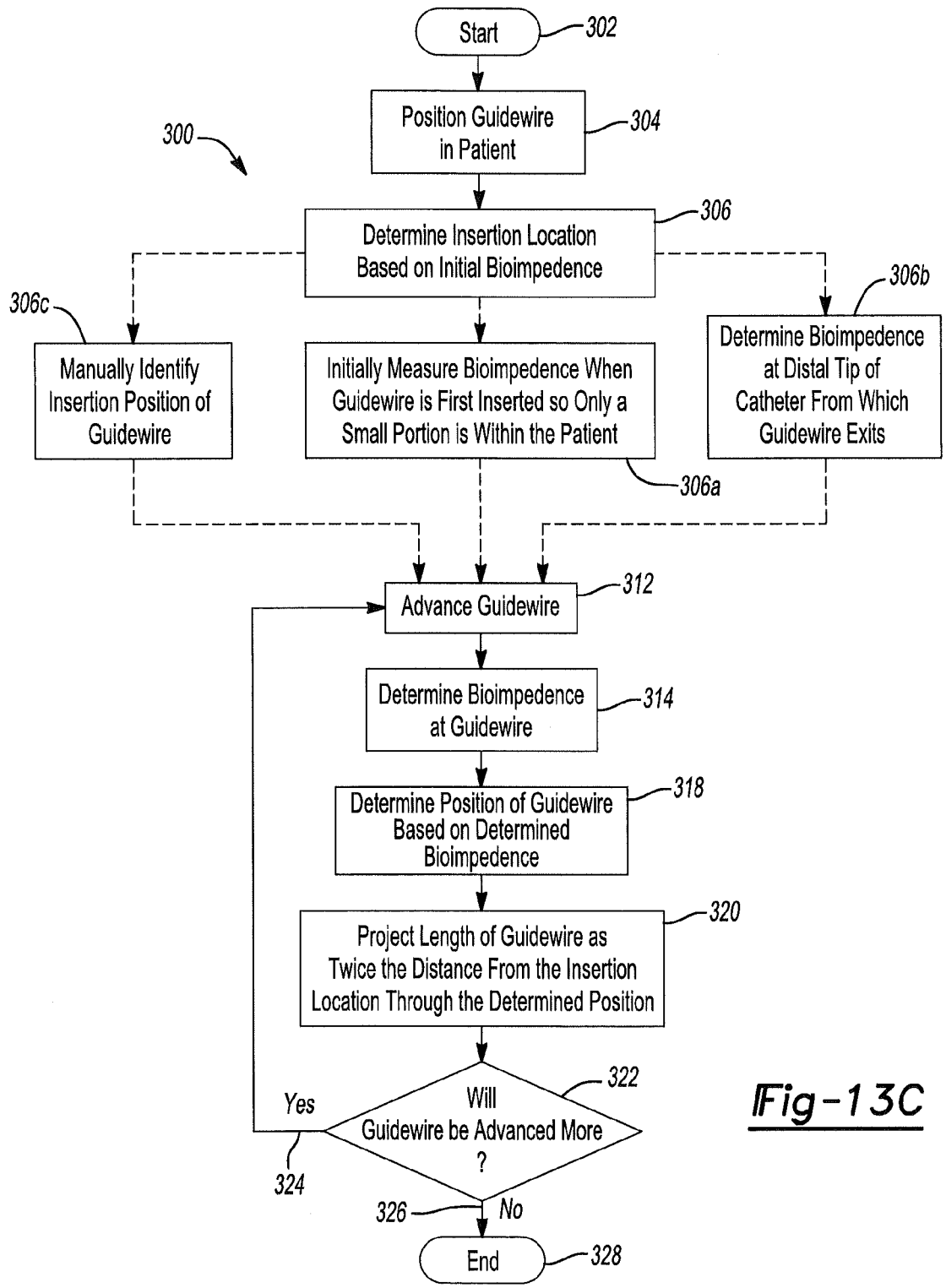

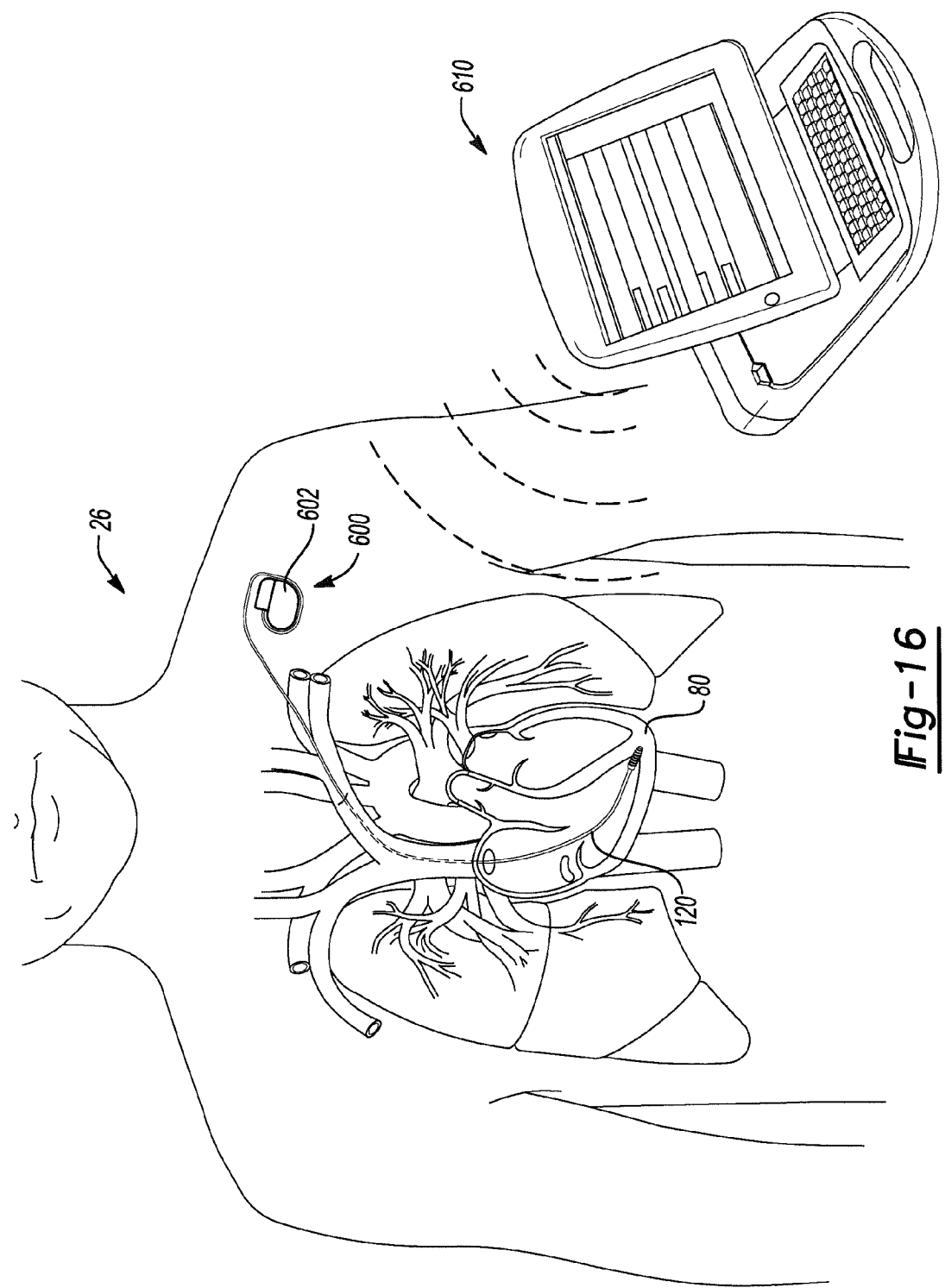

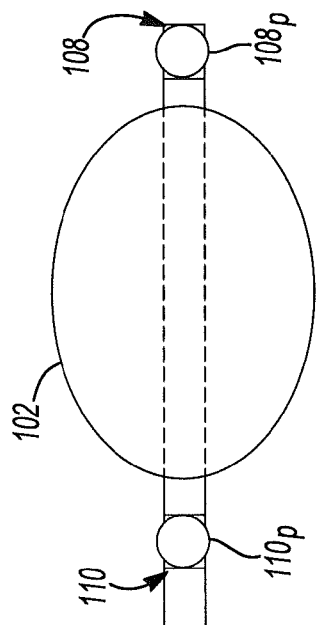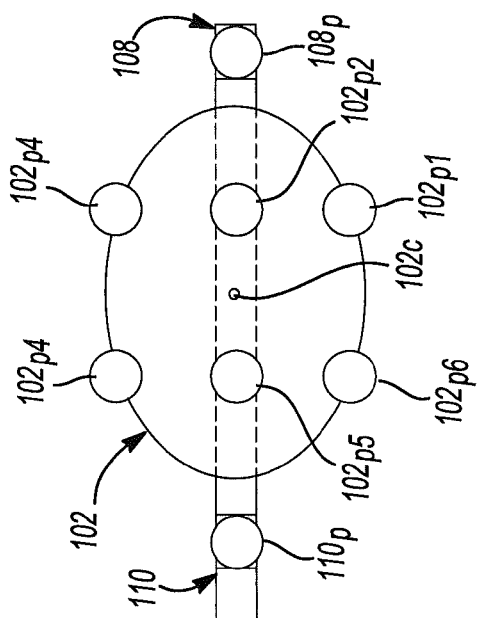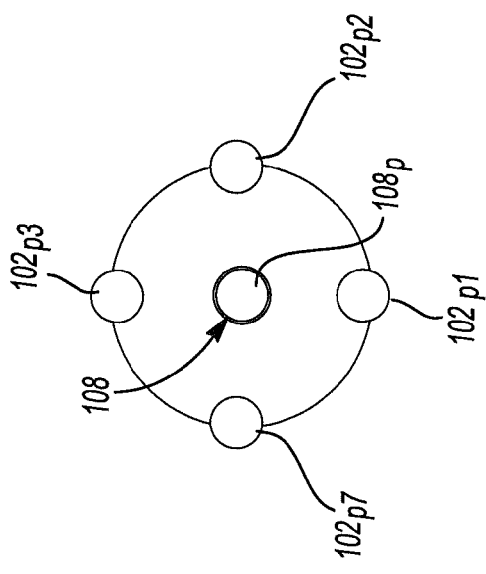
Fig-21A
Fig-21B
Fig-21C

| IF LAST KNOWN STATE OR LOCATION | ONLY POSSIBLE NEW CURRENT STATE( S ) OR LOCATION( S ) |
|---|---|
| Superior Vena Cava - ( SVC ) | Right Atrium - ( RA ) |
| Right Atrium - ( RA ) | Superior Vena Cava - ( SVC )<br>Inferior Vena Cava - ( IVC )<br>Tricuspid Valve ( TCV ) - Right Ventricle - ( RV )<br>Coronary Sinus - ( CS ) |
| Inferior Vena Cava - ( IVC ) | Right Atrium - ( RA ) |
| Right Ventricle - ( RV ) | Right Atrium - ( RA )<br>Pulmonic Valve ( PV ) - Pulmonary Artery - ( PA ) |
| Pulmonic Valve ( PV ) - Pulmonary Artery - ( PA ) | Right Ventricle - ( RV ) |

Fig-29A

594: SVC→RA - Yes - 1. EGM has a Deflection Coincident with ECG P-Wave (Fig 27A)
2. Position of Instrument Inferior of Previous Position
3. Pulse Pressure Non - Existant ( ≤ ≈ 1mmHg )

602: RA→SVC - Yes - 1. EGM Amplitude Coincident with ECG P-Wave Decreases
2. No Pulse Pressure Change Measured or ≤ ≈1mmHg
3. Measured Position of Lead Moved Toward SVC 604: RA→IVC - Yes - 1. A Decrease In EGM Amplitude Coincident with ECG P-Wave
2. No Pulse Pressure Change Measured or ≤ ≈1mmHg
3. Lead Position Moved Away and Inferior From SVC 618: IVC→RA ( Yes ) - 1. An Increase in EGM Coincident with ECG P-Wave
2. Determined Position of Lead in RA 606A: TCV Annulus ( Yes ) - 1. Pressure Pulse Medium ( About 5 - 15mmHg )
2. Spikes in EGM Coincident with R and P-Wave ( Fig - 27C )

606: RA→RV ( Yes ) - 1. Pulse Pressure Large ( Greater Than About 10 - 15 mmHg )
2. EGM has Large Amplitude Coincident with ECG R-Wave 634: RV→RA ( Yes ) - 1. Decrease in Pulse Pressure ( From Large to Non - Existant )
2. EGM has Voltage Amplitude Coincident with ECG P-Wave
3. EGM No Longer has Large Voltage Amplitude Coincident
with ECG R-Wave 640: RV→PA ( Yes ) - 1. Pulse Pressure Medium ( 5 - 15 mmHg ) Less than
RV Pulse Pressure, but Greater than RA Pulse Pressure
2. EGM Similar to TCV EGM ( Fig - 27C )

646: PA→RV ( Yes ) - 1. EGM has Deflection Coincident with ECG R-Wave
2. Pulse Pressure Increased to Large ( ≥ About 10 - 15 mmHg )

608: RA→CS ( Yes ) - 1. Small Pulse Pressure About 1 mmHg to About 5 mmHg

Fig-29C

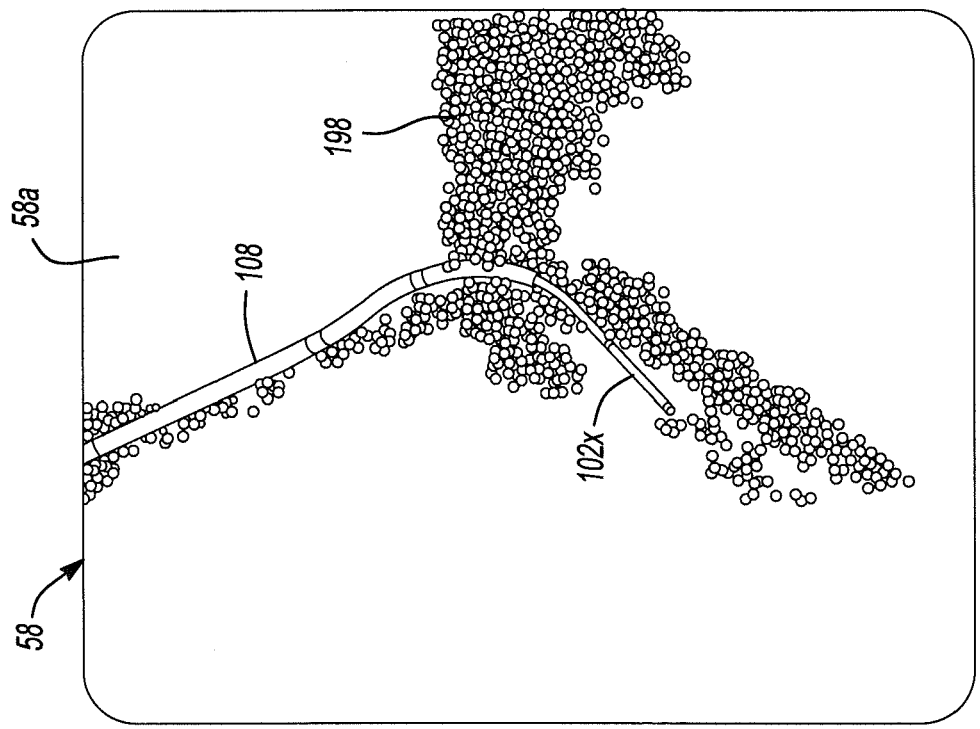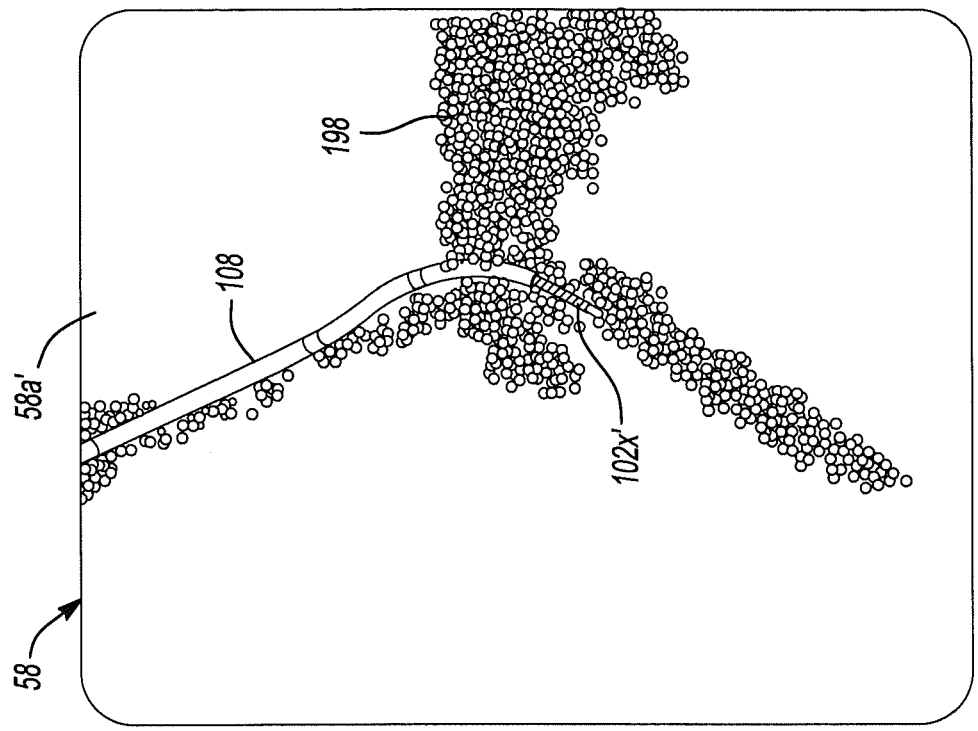
Fig-35

DETERMINING A MATERIAL FLOW CHARACTERISTIC IN A STRUCTURE

CROSS-REFERENCE TO RELATED APPLICATIONS

This application is a continuation of U.S. application Ser. No. 12/421,364, filed Apr. 9, 2009, entitled "Method and Apparatus for Mapping a Structure," which is a continuation-in-part of U.S. application Ser. No. 12/117,537, filed May 8, 2008, entitled "Method and Apparatus for Mapping a Structure," which claims benefit of U.S. Provisional Application No. 61/046,298, filed Apr. 18, 2008, entitled "Method and Apparatus for Mapping A Structure." The disclosures of all of the above identified applications are incorporated herein by reference.

This application also includes subject matter related to the subject matter disclosed in U.S. patent application Ser. No. 12/421,375, filed on Apr. 9, 2009; and U.S. patent application Ser. No. 12/421,332, filed on Apr. 9, 2009; and U.S. application Ser. No. 12/117,549, filed May 8, 2008, entitled "Method and Apparatus for Mapping a Structure." The disclosures of all of the above identified applications are incorporated herein by reference.

FIELD

The present disclosure relates generally to anatomical position determination, and particularly to mapping an anatomical region and illustrating the map.

BACKGROUND

The statements in this section merely provide background information related to the present disclosure and may not constitute prior art.

The human anatomy includes many types of tissue that can either voluntarily or involuntarily, perform certain functions. After disease or injury, or due to certain genetic predispositions certain tissues may no longer operate within general anatomical norms. For example, after disease, injury, time, or combinations thereof, the heart muscle may begin to experience certain failures or deficiencies. These failures or deficiencies may be corrected or treated with implantable medical devices (IMDs), such as implantable pacemakers, implantable cardioverter defibrillator (ICD) devices, cardiac resynchronization therapy defibrillator devices, or combinations thereof.

One of the main portions of the IMD can include one or more leads that are directly connected to tissue to be affected or treated by the IMD. The lead can include a tip or electrode portion that is directly connected to a first portion of the anatomical tissue, such as a muscle bundle, and a lead body that connects to the second main portion, which is the device body or therapeutic driving device. It is generally known that the device body or case portion can be implanted in a selected portion of the anatomical structure, such as in a chest or abdomen, and the lead can be inserted through various venous portions so that the tip portion can be positioned at the selected position near or in the heart muscle.

The IMDs are implantable devices that may require the use of imaging devices for implantation. The imaging devices can include fluoroscopes that expose a patient and a surgeon to ionizing radiation. In addition, the use of the imaging device can require time for acquiring image data and understanding the images from the image data. For example, considerable experience and training may be required for proper interpretation of fluoroscopic images.

The use of various imaging devices can require various additional costs and procedures. For example, fluoroscope devices employ ionizing radiation to acquire images of a patient. Individuals, such as surgeons and technicians that attend the implantation procedure may be constantly or repeatedly exposed to the ionizing radiation and are generally required to wear protective clothing. The protective clothing, however, can be heavy and may strain operators and staff. In addition, the imaging devices, such as fluoroscopes, magnetic resonance imagers, ultrasound systems, can be relatively expensive and require extensive training in the use of the imaging device. Due to cost and training requirements, therefore, certain facilities may forego acquiring the imaging devices thereby reducing the number of facilities able to perform certain procedures.

SUMMARY

A position sensing unit (PSU) system is operable to map and illustrate mapped and saved points. The system can determine the location or position of a tracking or position element. The tracking element can be an electrode and a position is determined by generating a voltage in a patient and calculating an impedance at the electrode. The calculated impedance is used to determine the position of the electrode as in a patient or other appropriate conducting medium.

The saved points may be used to create a map determined with the electrode that can be used to determine a location of a later positioned electrode. The electrode positioned in the anatomy can include a pacing lead, defibrillation lead, or lead for any other purpose. The electrode can generally be a part of an IMD. The map generated with the PSU can be used to guide or navigate a lead to a selected location without the use of other prior or concurrent imaging devices, such as an external fluoroscope, magnetic resonance imaging (MRI), ultrasound (US), etc.

The use of the position sensing unit to generate a map can eliminate or reduce the need for another imaging device. The imaging devices, such as fluoroscopes, as discussed above, can require additional costs and training requirements that may be eliminated. For example, if a fluoroscope is not used, protective clothing, such as a lead apron, may not be required to be worn by individuals in a room and can reduce stress and weight carried by the individuals. In addition, elimination of ionizing radiation doses can benefit a patient and a user. Further, with the use of the position sensing unit and the elimination or reduction in use of another imaging device, a cost center or capital investment may be reduced or eliminated while allowing a facility to perform selected procedures, as discussed herein.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4A is a detailed view of the implantable retractable lead in a retracted configuration, according to various embodiments;

FIG. 4B is a detailed view of the implantable retractable lead in an extended configuration, according to various embodiments;

FIG. 6 is a detailed view of a display device with mapping data illustrated thereon;

Figure 13B:
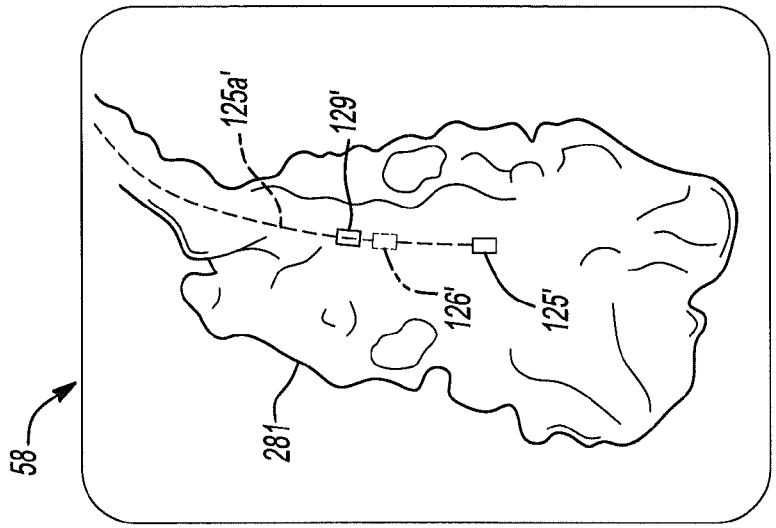
Figure 13A:
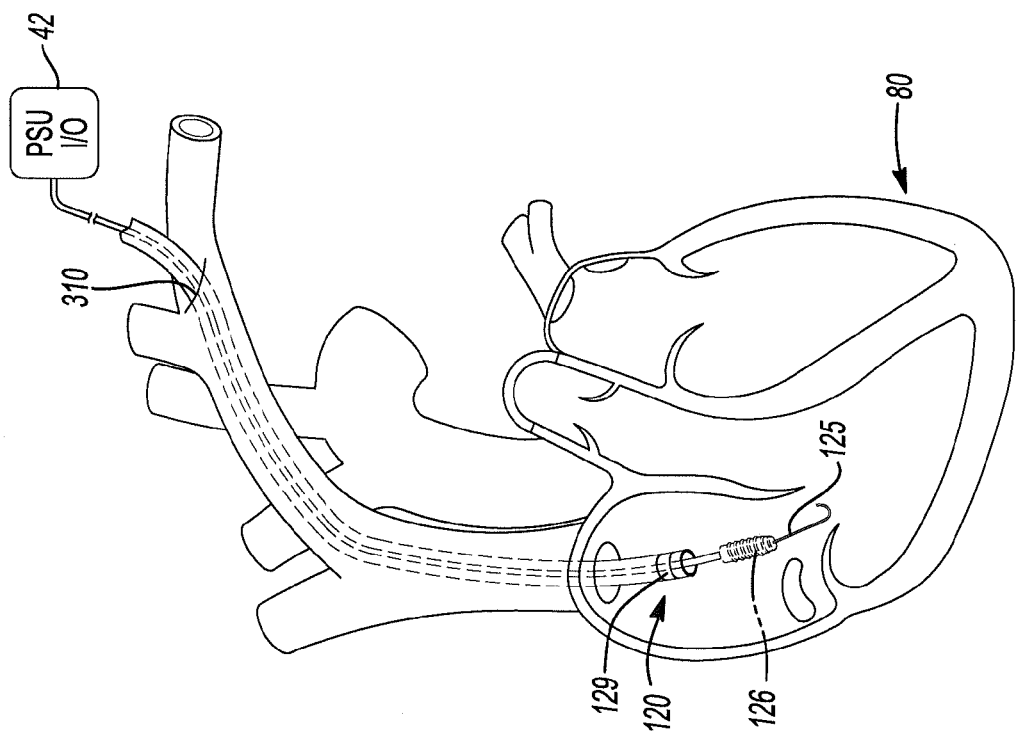
Figure 14:
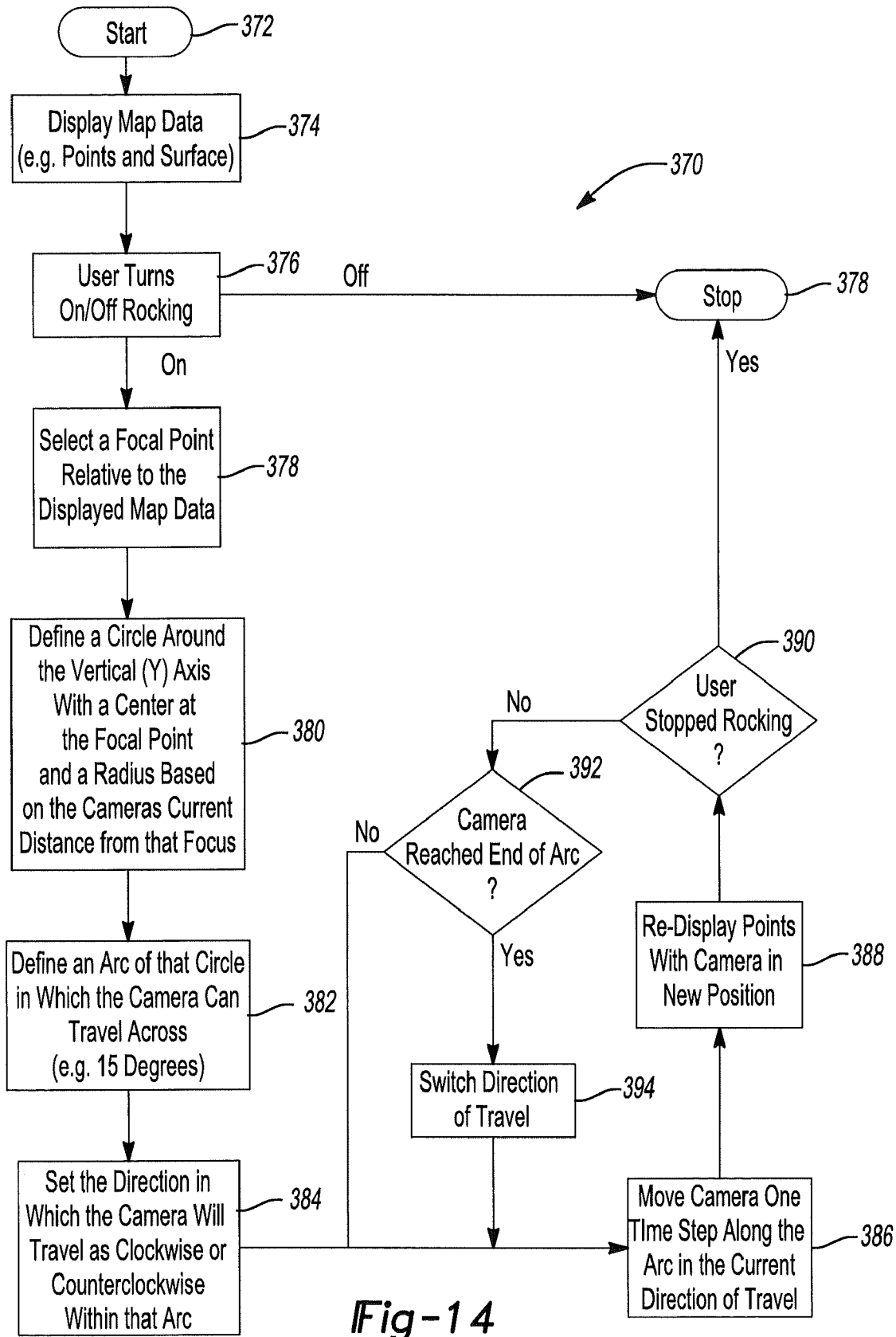
Figure 15A:
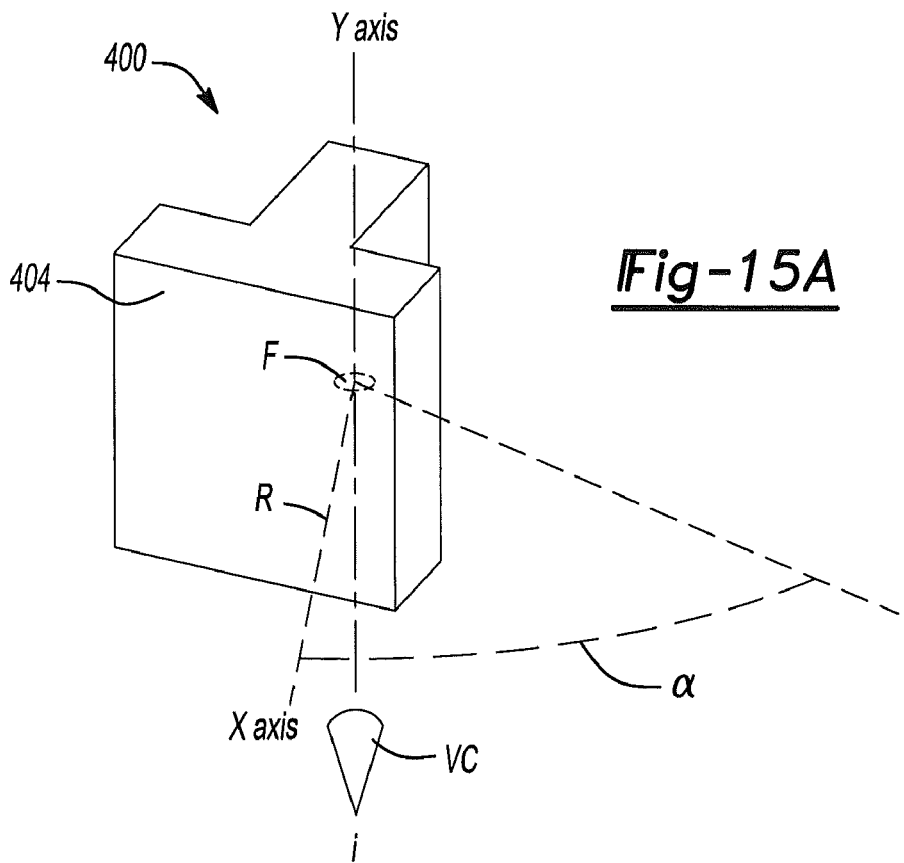
Figure 15B:
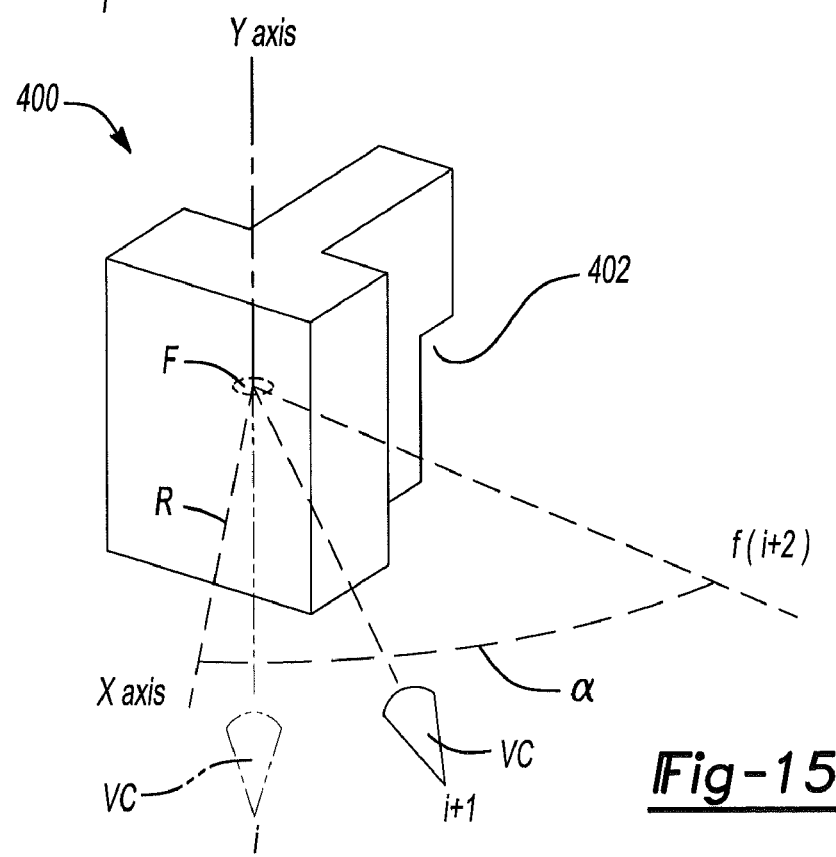
Figure 17:
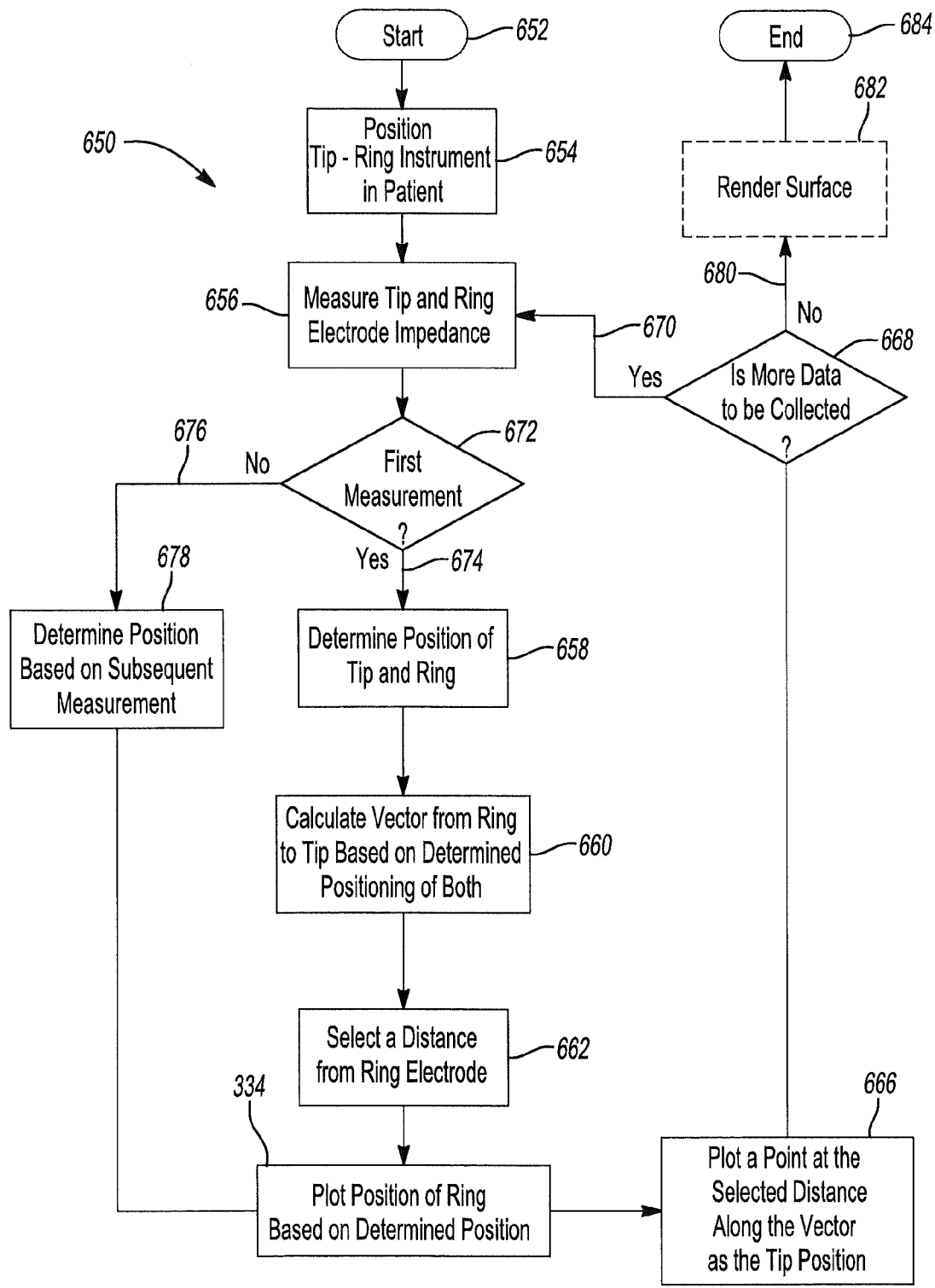
Figure 18B:
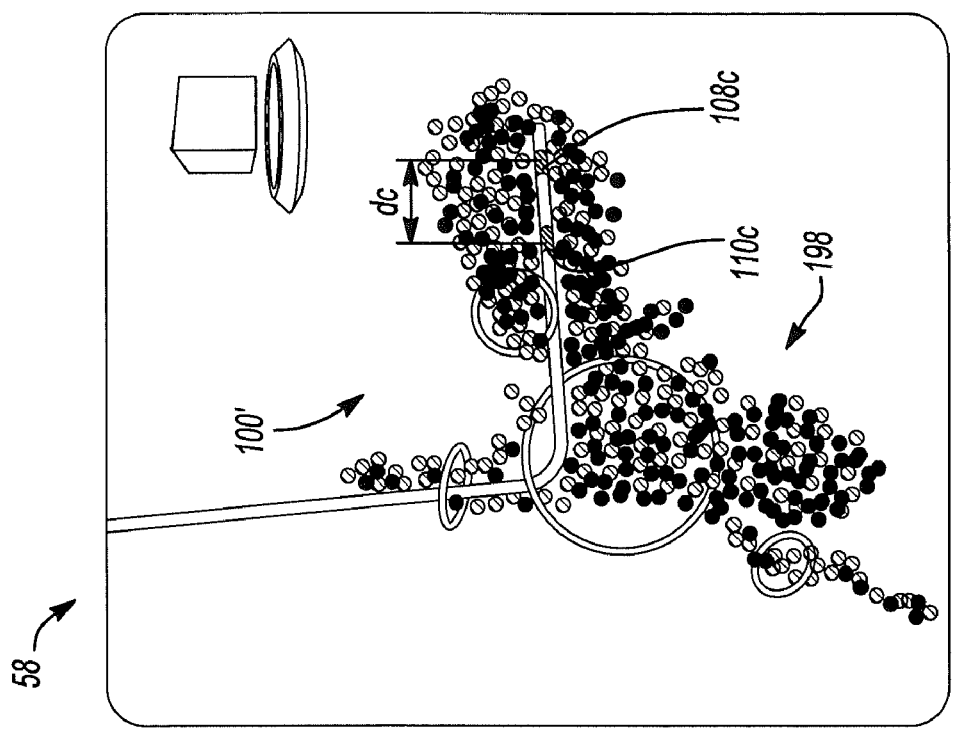
Figure 18A:
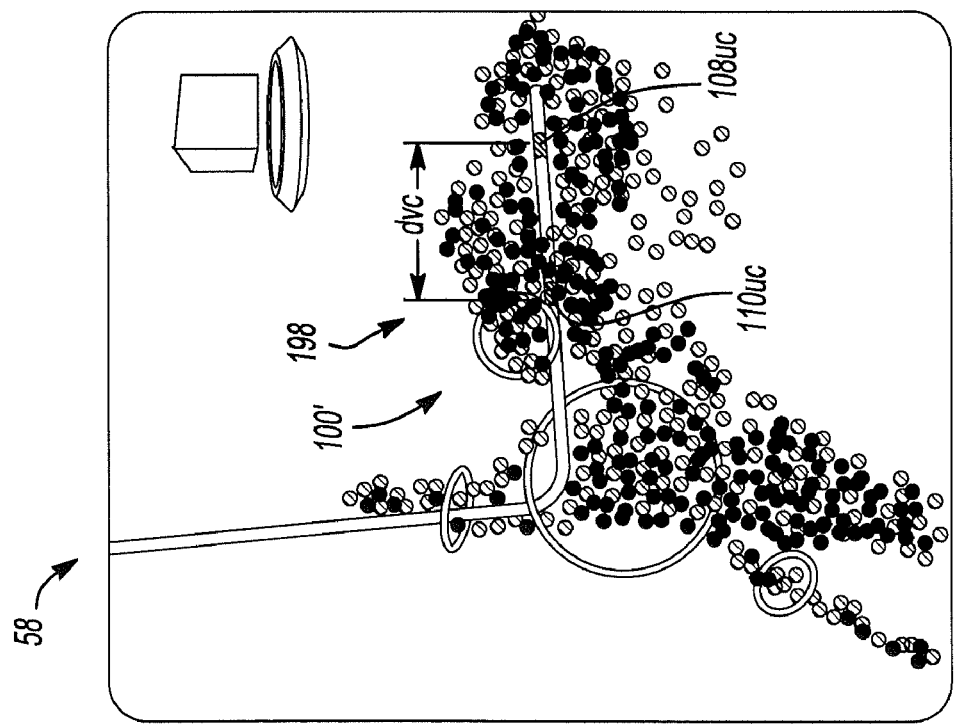
Figure 19A:
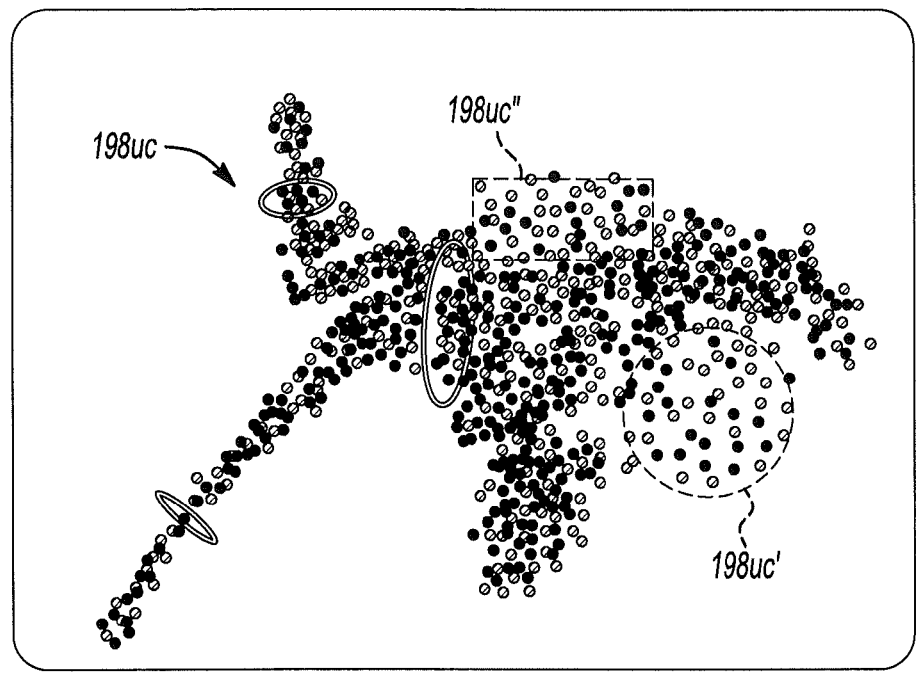
Figure 19B:
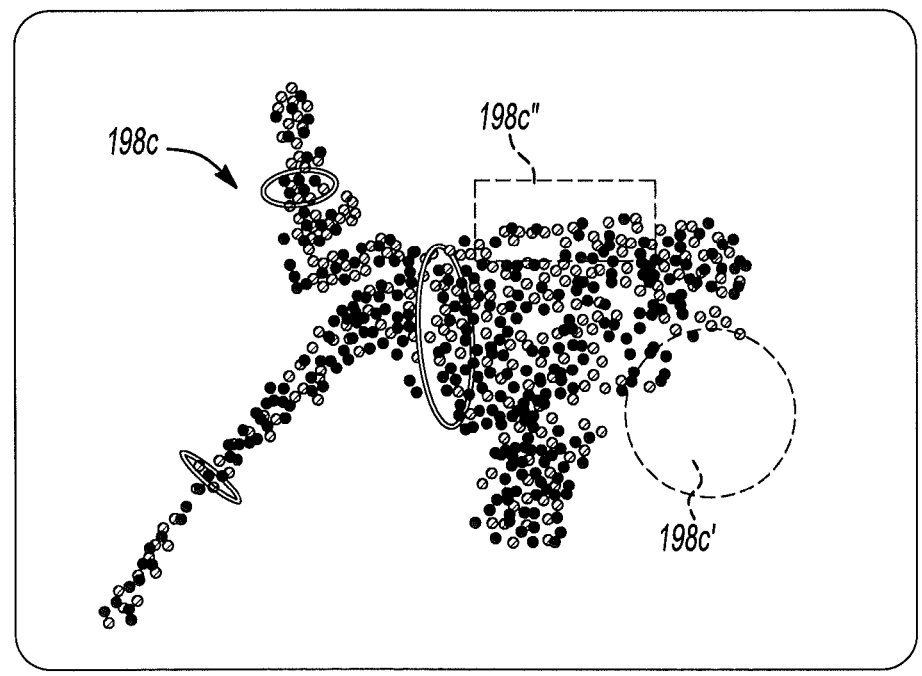
Figure 20:
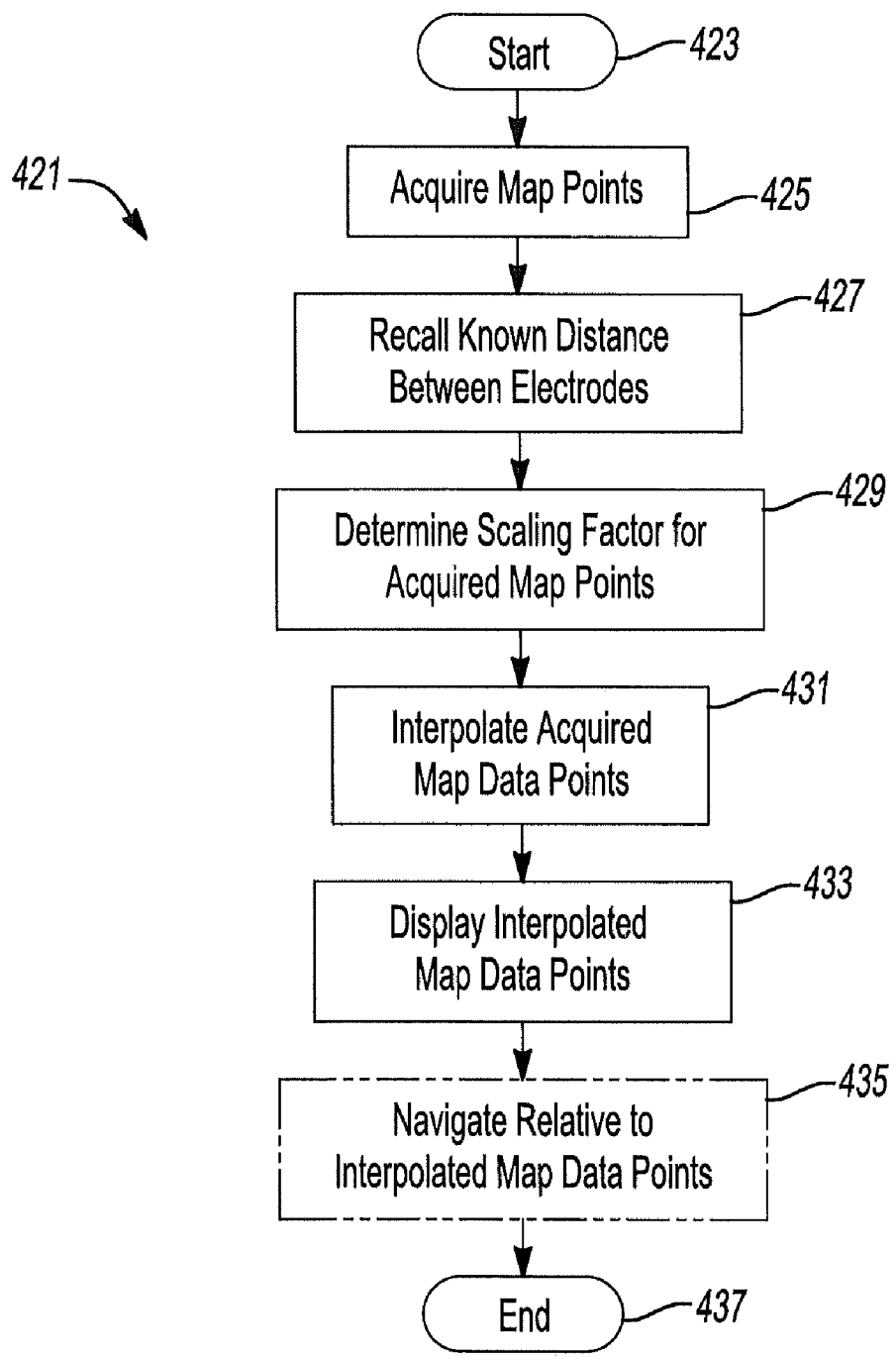
Figure 22A:
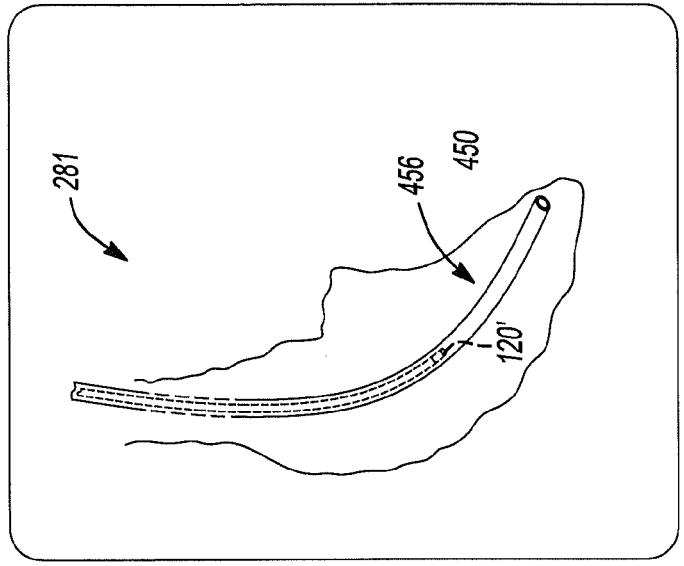
Figure 22B:
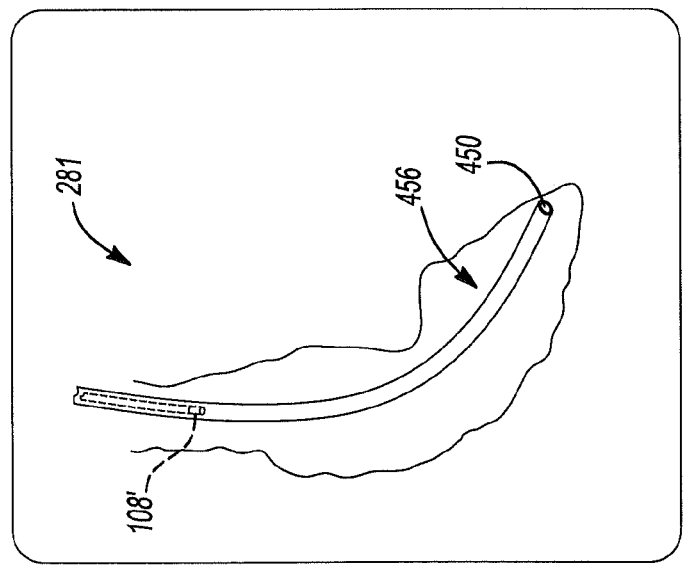
Figure 22C:
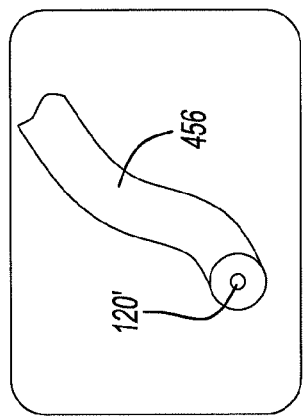
Figure 23B:
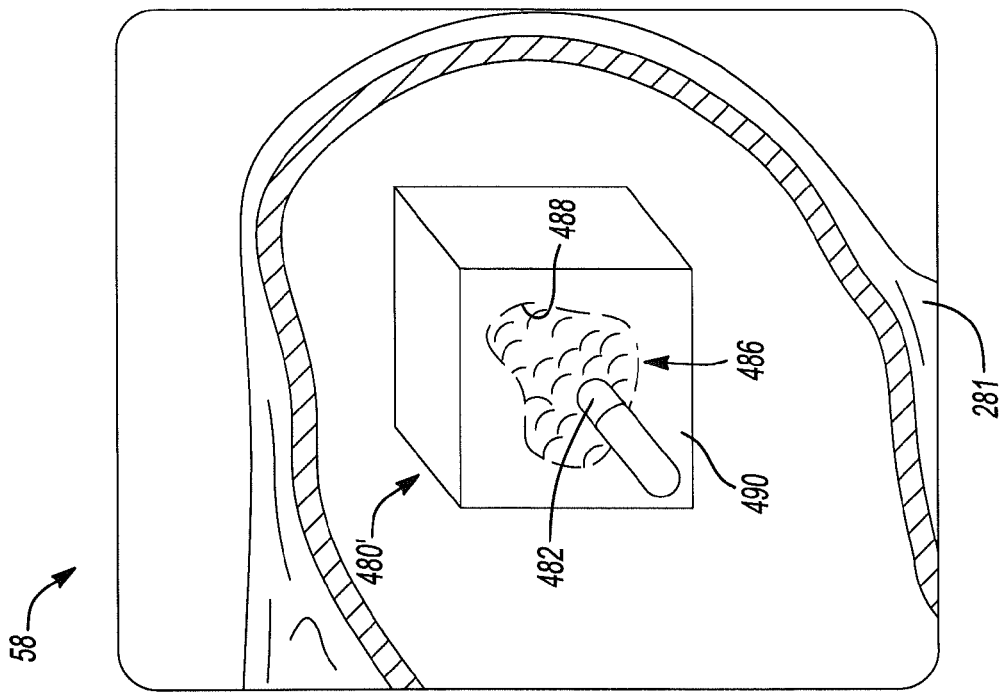
Figure 23A:
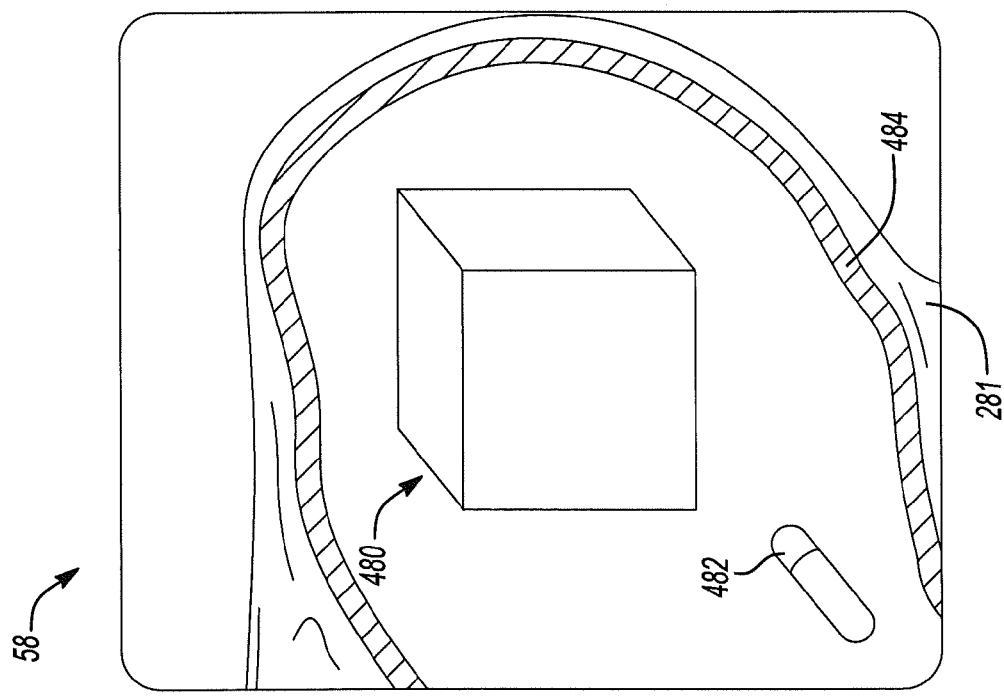
Figure 24A:
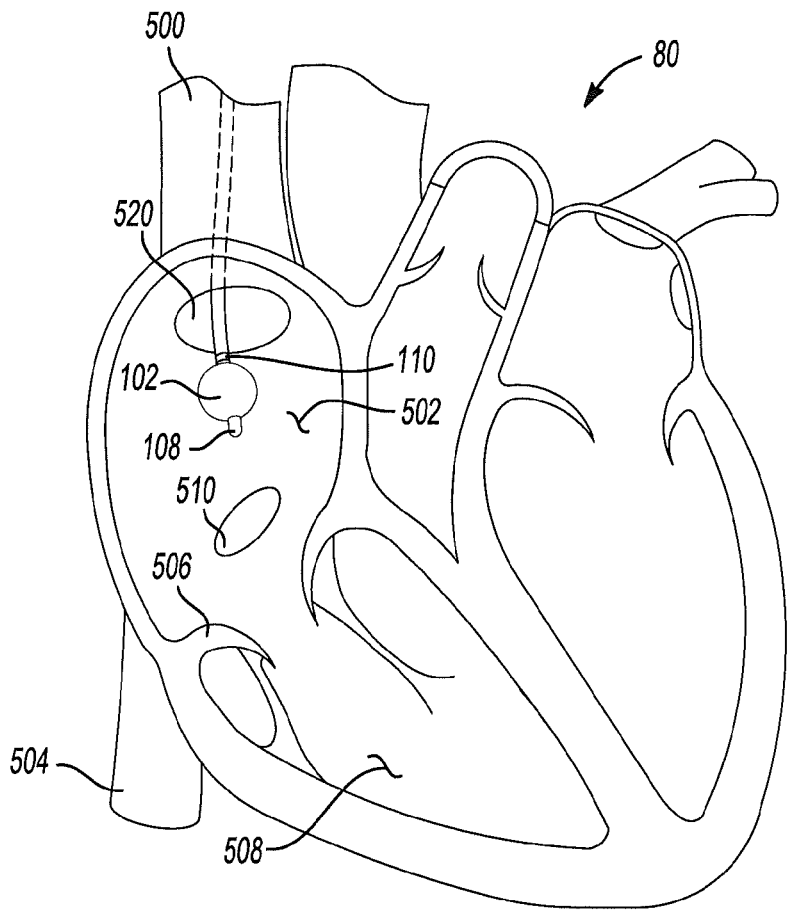
Figure 25:
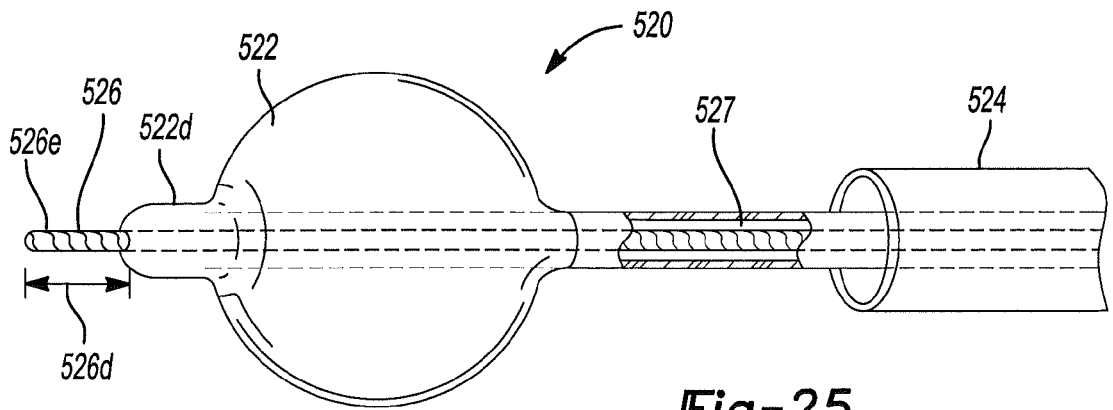
Figure 24B:
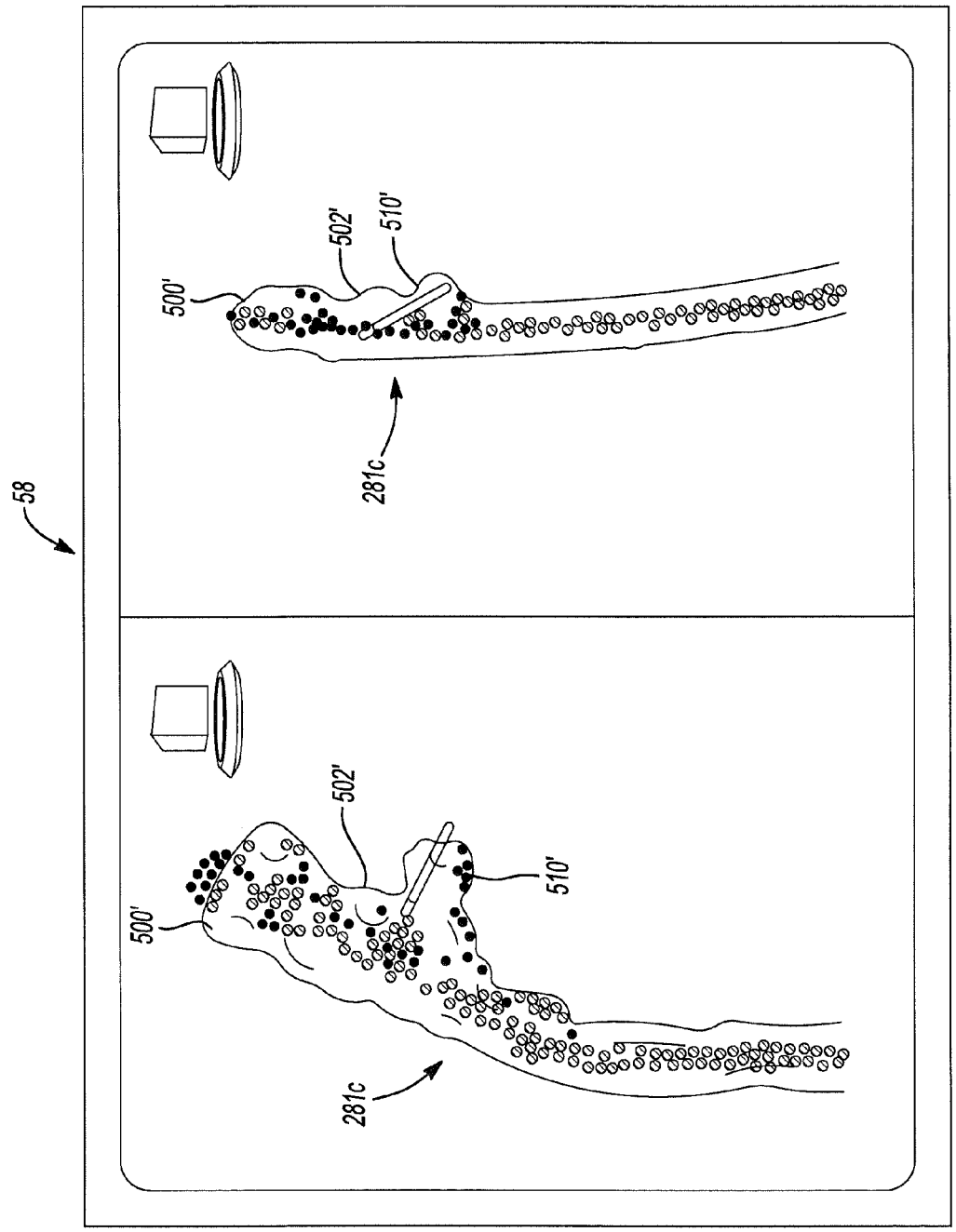
Figure 24C:
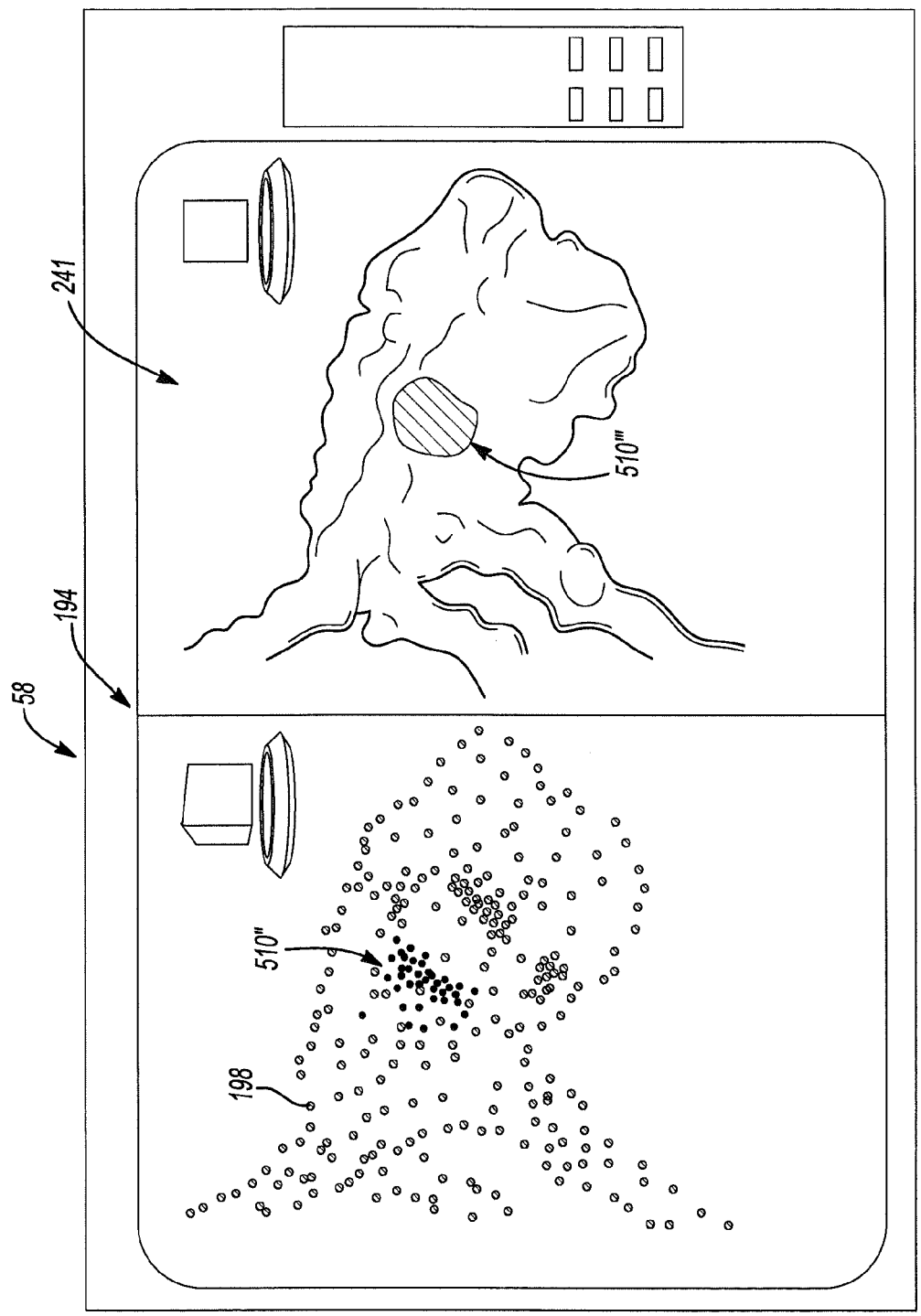
Figure 26A:
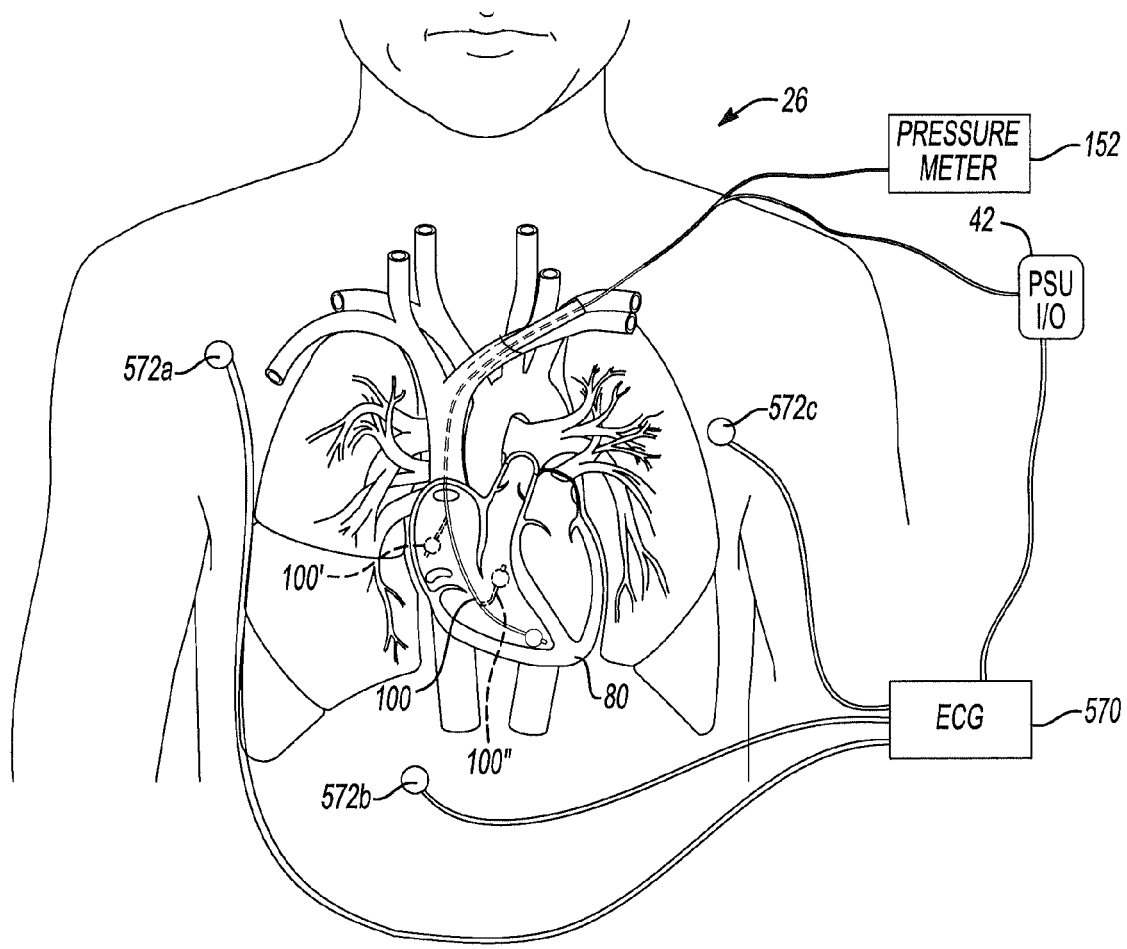
Figure 26B:
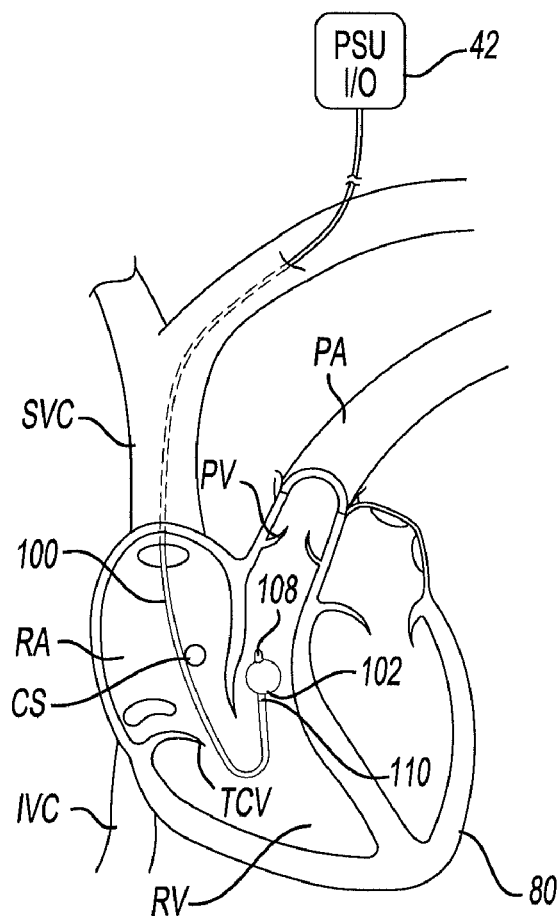
Figure 28:
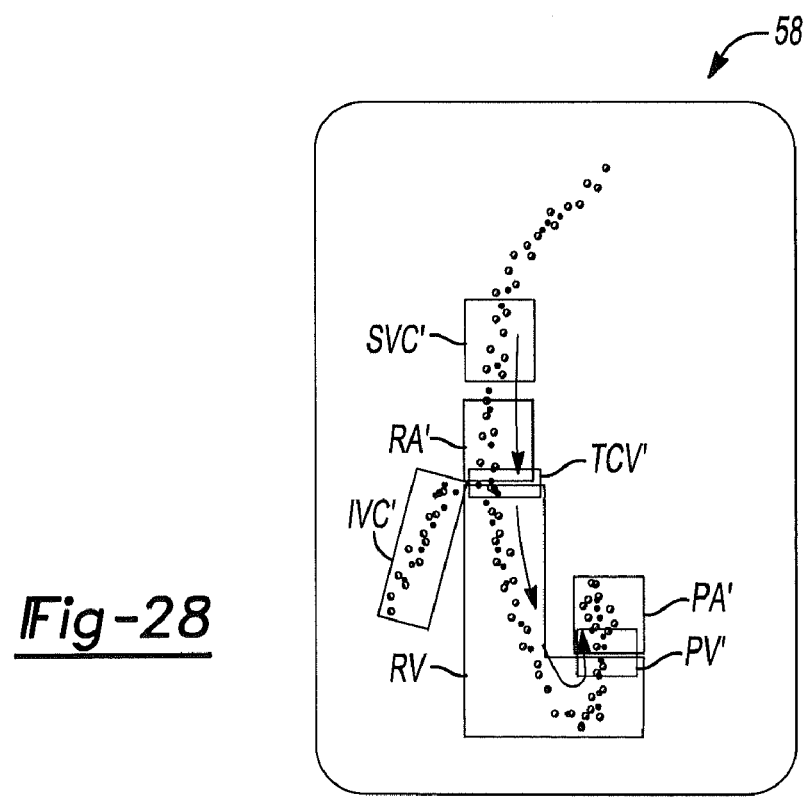
Figure 29B:
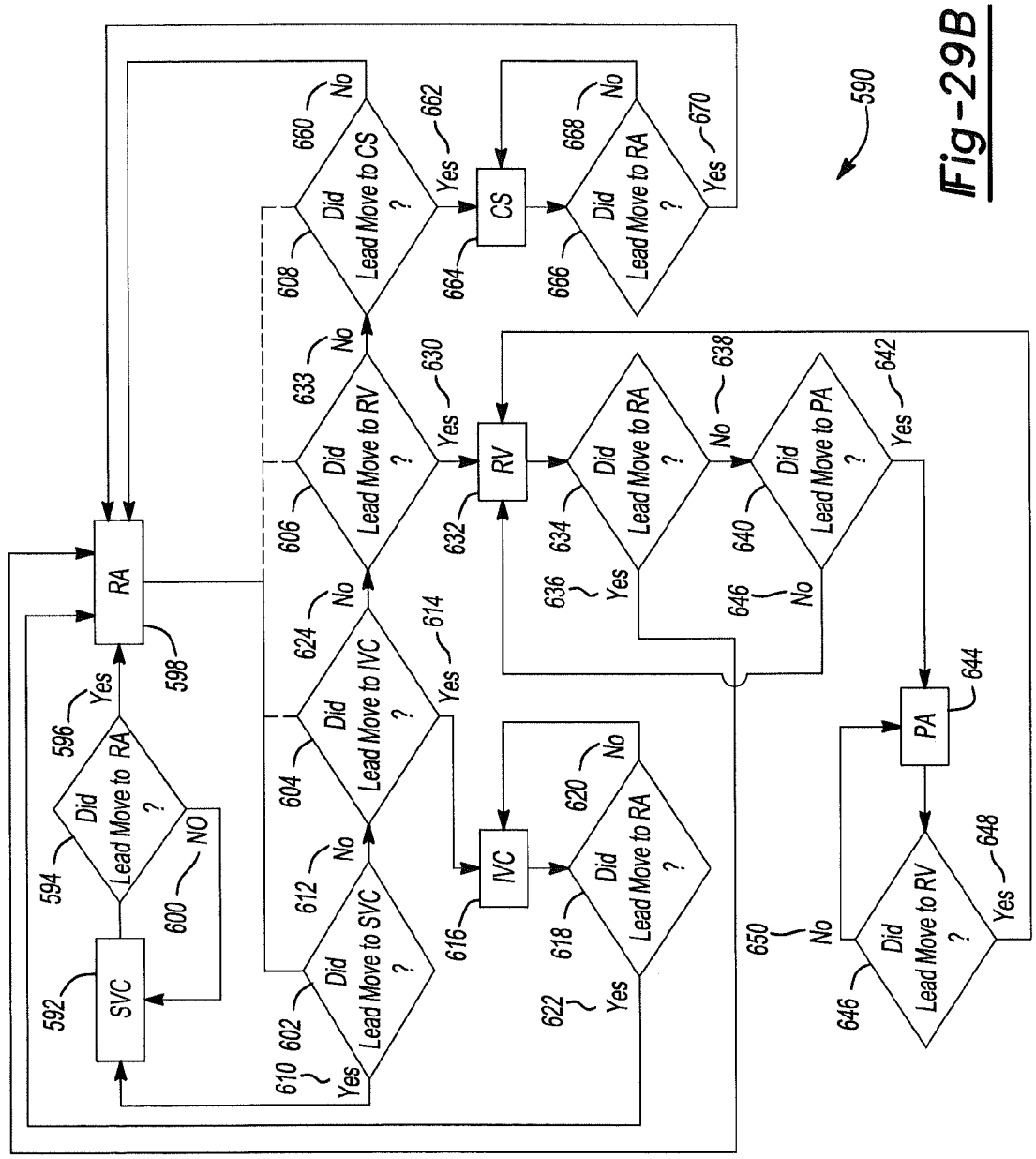
Figure 29C:
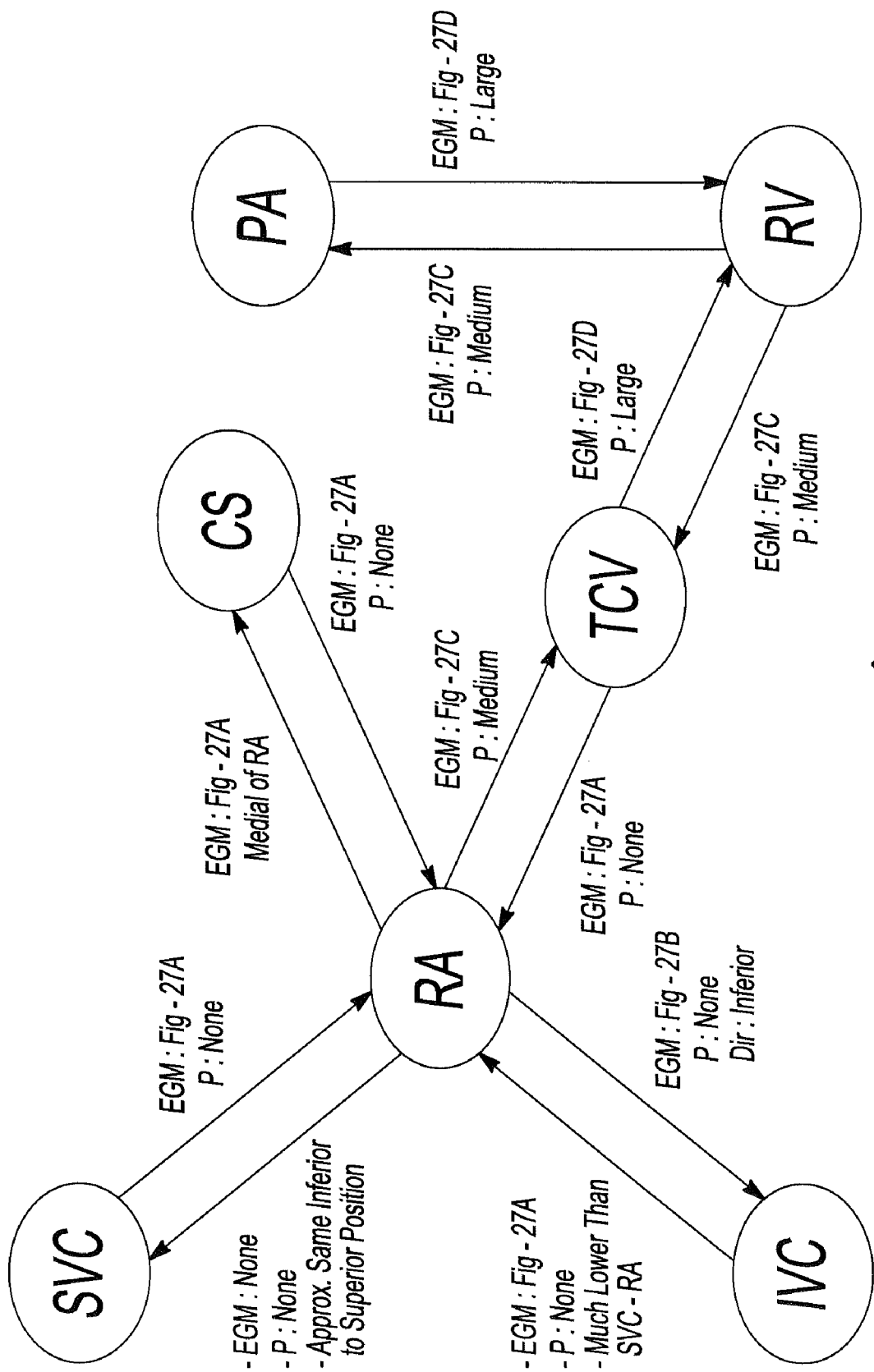
Figure 30A:
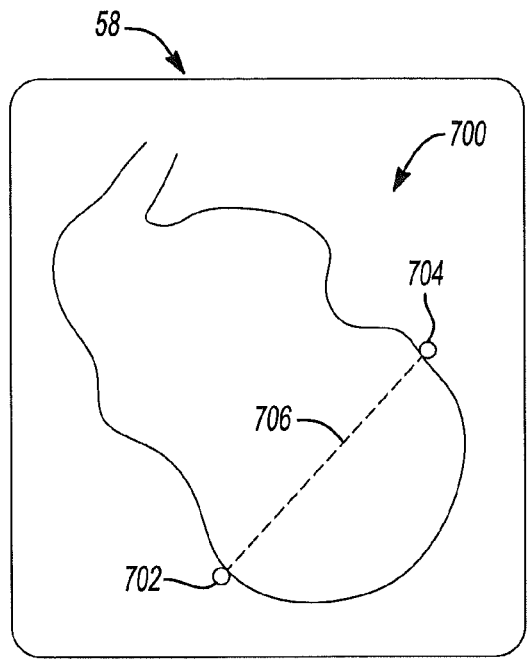
Figure 30B:
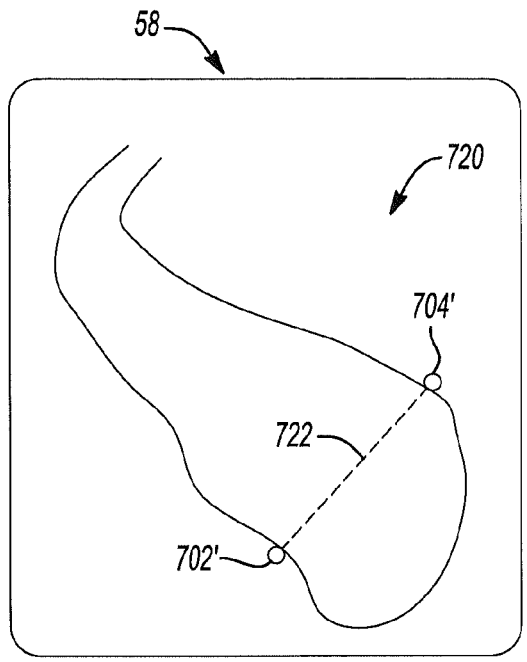
Figure 31A:
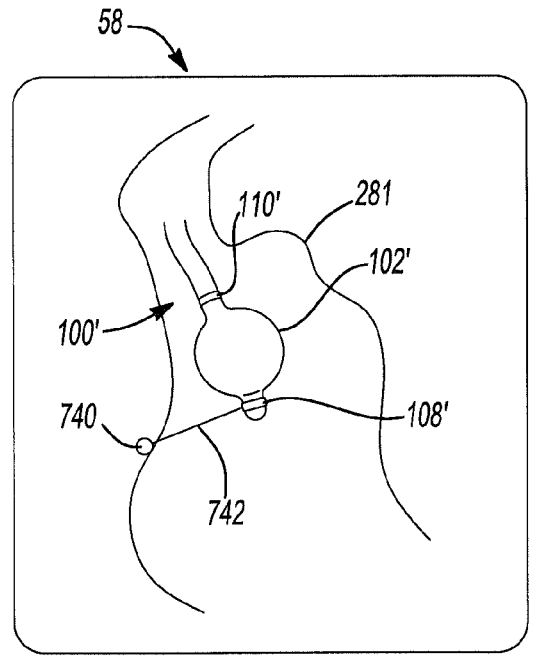
Figure 31B:
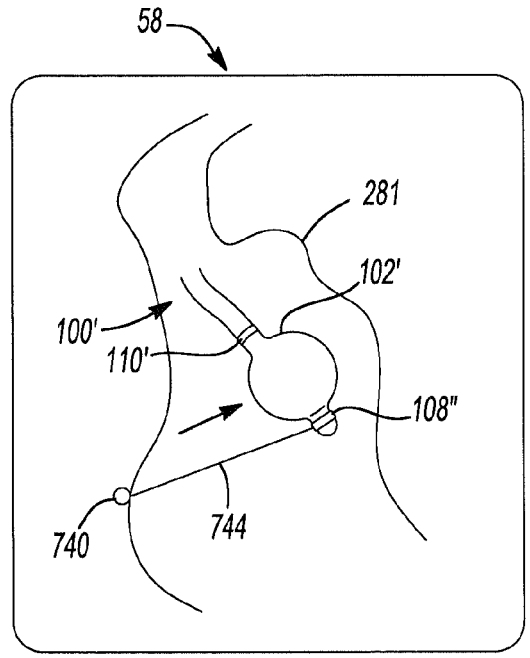
Figure 32:
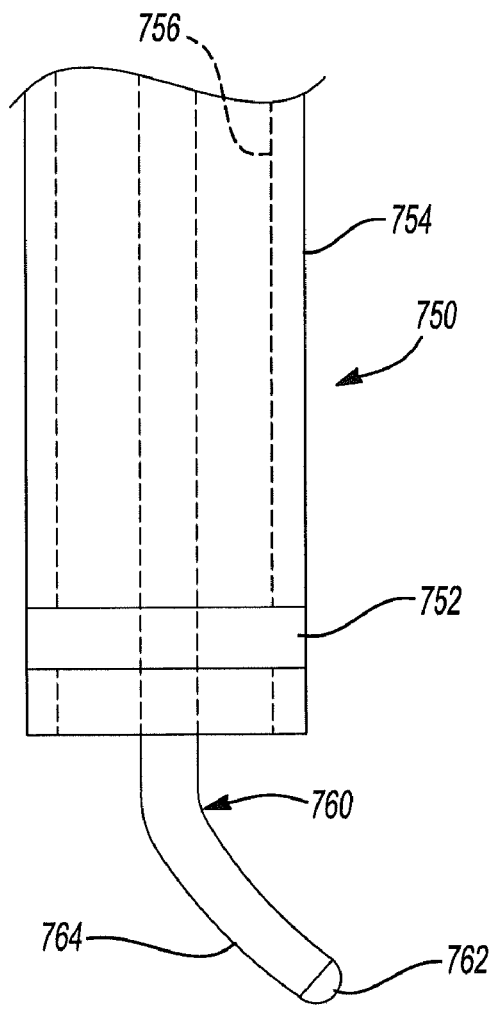
Figure 33:
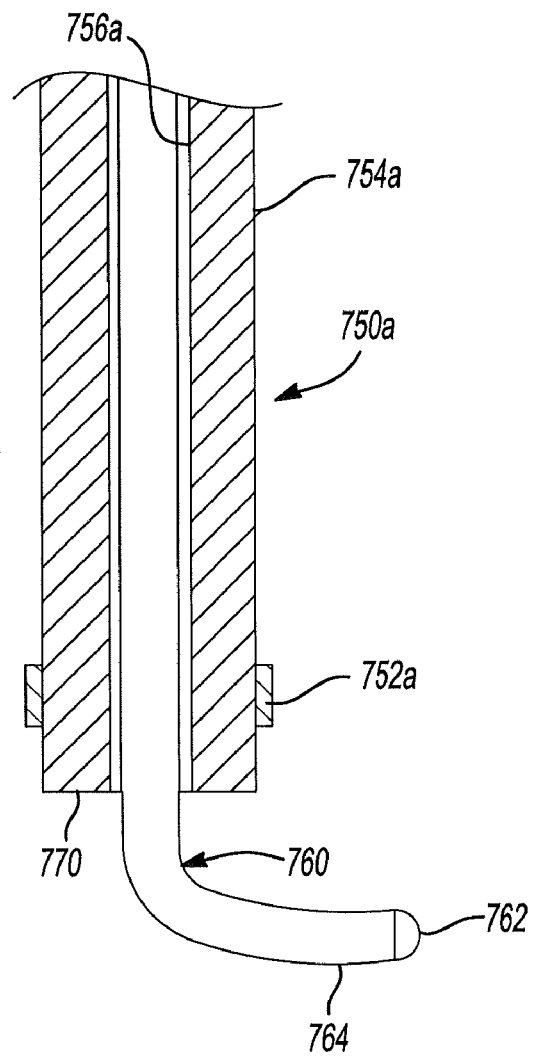
Figure 34B:
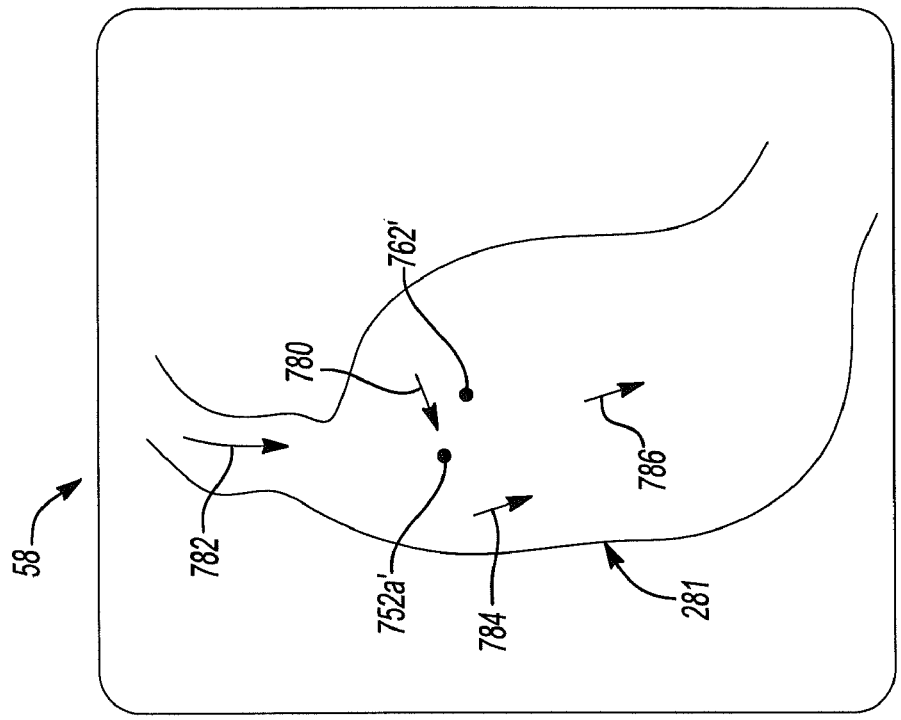
Figure 34A:
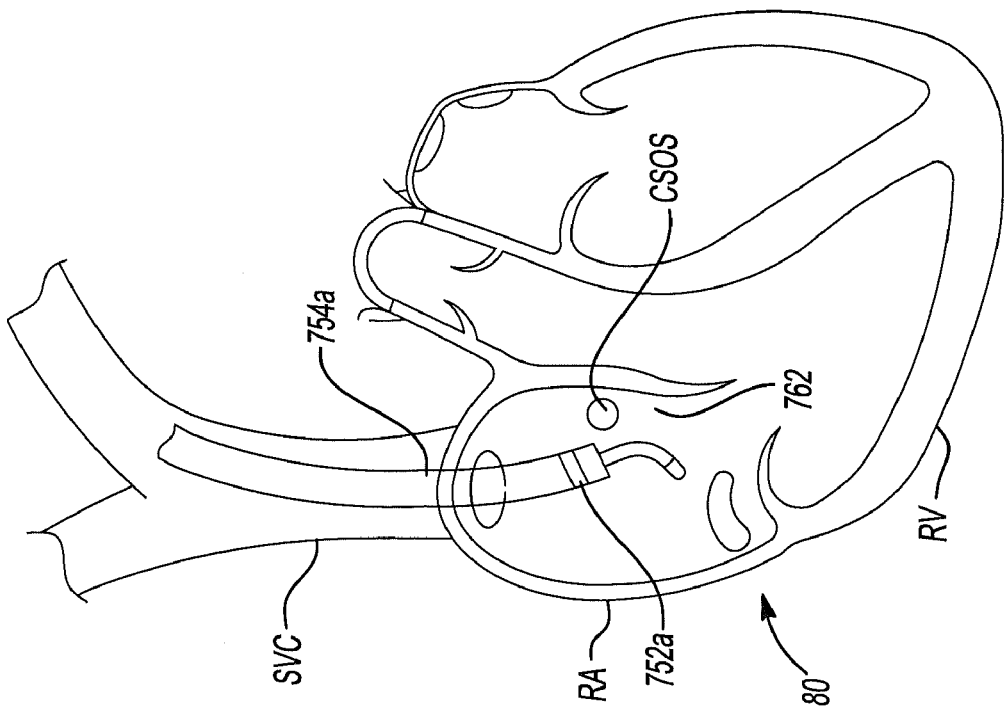
Figure 36:
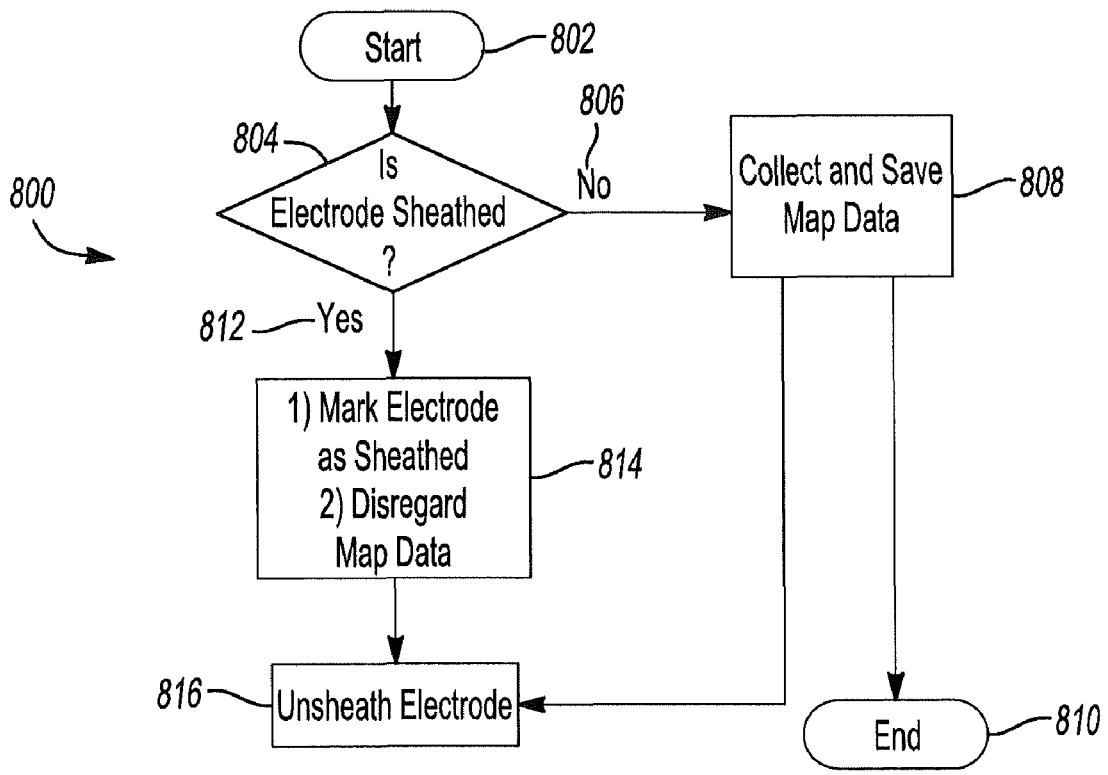

FIGS. 12A(i)-12C(ii) illustrates various embodiments of a lead with multiple tracking electrodes and illustrations and a display thereof;

FIG. 13A is a detailed partial cut-away view of a heart and a lead positioned therein with a guide wire;

FIG. 13B is an illustration on a display for tracking a lead with a guide wire;

FIG. 13C is a flowchart illustrating a method of tracking a guide wire;

FIG. 14 is a flowchart illustrating a method of displaying a three dimensional nature of data;

FIGS. 15A-15B illustrate an example of demonstrating a three dimensional nature of data;

FIG. 16 is a view of an implantable medical device positioned within a patient;

FIG. 17 is a flowchart illustrating a method of correcting of a distortion;

FIGS. 18A and 18B illustrate a graphical representation of data before and after correcting for a distortion;

FIGS. 19A and 19B illustrate a graphical representation of data before and after correction for a distortion;

FIG. 20 is a flowchart illustrating a method of correcting a display for distortions;

FIGS. 21A-21C is a schematic view of a mapping catheter and multiple virtual points;

FIGS. 22A-22C is a graphical representation of a pathway generation and display on a display device;

FIGS. 23A-23B is a graphical representation of displaying position data;

FIG. 24A is a schematic illustration of a heart with a lead positioned therein;

FIG. 24B is a graphical representation of a surface based upon mapping data;

FIG. 24C is a graphical illustration of data on a display device based upon mapping data and sensor data;

FIG. 25 is a mapping catheter, according to various embodiments;

FIG. 26A is an illustration of a PSU and various physiological sensors;

FIG. 26B is a schematic view of a mapping catheter within a heart;

FIGS. 27A-27D illustrate schematic representations of an electrogram graph and an electrocardiogram graph illustrated on the same time axis;

FIG. 28 is a graphic representation on a display device of identified locations within a patient;

FIG. 29A is a chart showing next possible locations based on last known position;

FIGS. 29B-29C illustrate a flowchart for identifying a state or position of a mapping catheter or leads;

FIG. 29C' is a simplified flow chart showing next possible locations within a heart of an instrument based on last known locations;

FIGS. 30A-30B illustrate a dimensional change displayed on a display device;

FIGS. 31A-31B illustrate a flow direction graph representation of movement on a display device;

FIG. 32 illustrates a mapping catheter with a flexible portion;

FIG. 33 illustrates a mapping catheter with a flexible portion, according to various embodiments;

FIG. 34A is a schematic view of a heart with a mapping catheter and a flexible portion, according to various embodiments;

FIG. 34B is a graphical representation of location information;

FIG. 35 is a representation of a display device illustrating a sheathed and unsheathed electrode; and FIG. 36 is a flowchart for utilization of position data.

DETAILED DESCRIPTION

The following description is merely exemplary in nature and is not intended to limit the present disclosure, application, or uses. The devices described herein include an exemplary number of leads, case bodies, etc. One will understand that the components, including number and kind, may be varied without altering the scope of the disclosure. Also, devices according to various embodiments may be used in any appropriate diagnostic or treatment procedure, including a cardiac, neural, or other anatomical procedures.

Overview

Figure 1:
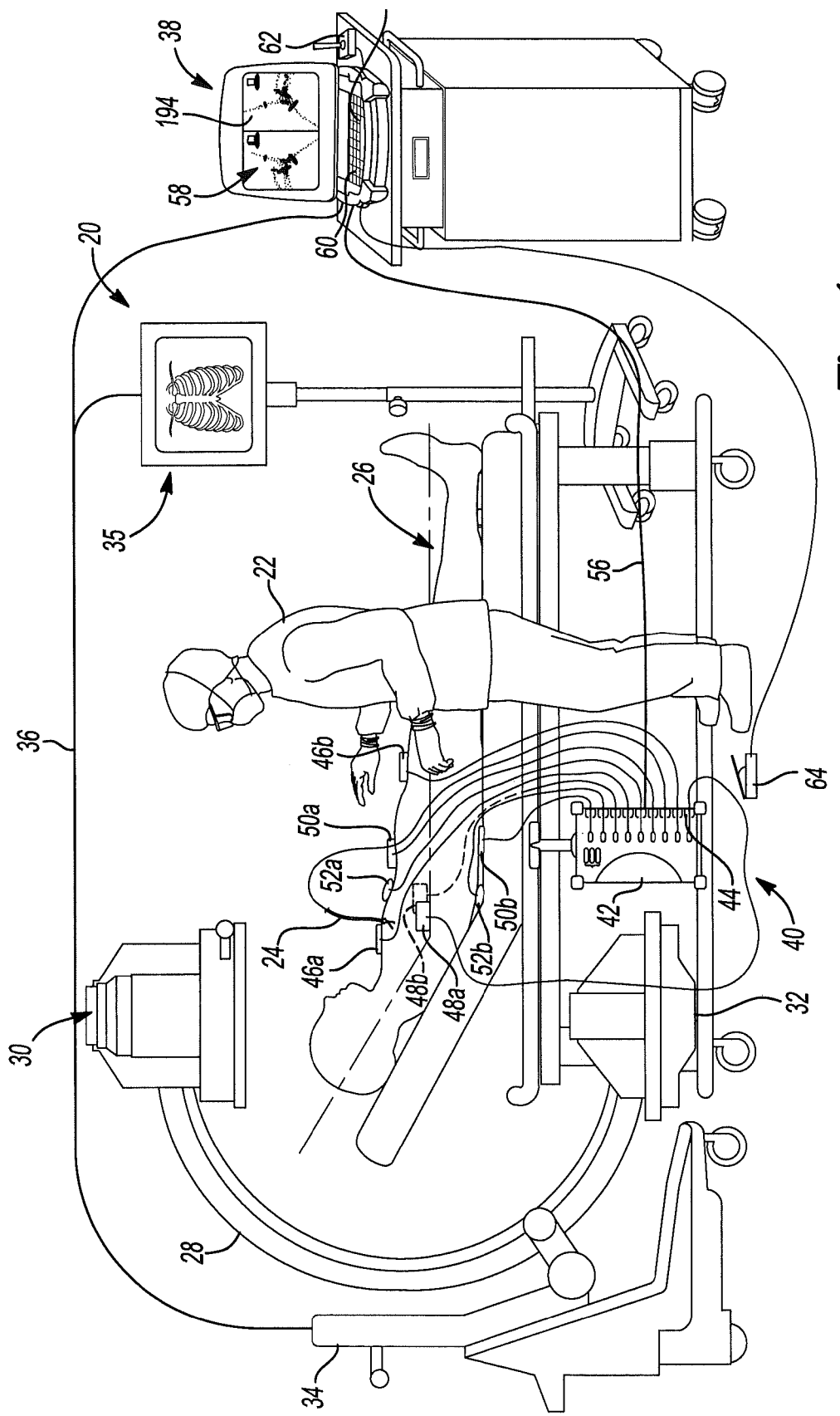
FIG. 1 is an environmental view of a mapping or navigation system.

As discussed herein, a navigation system, such as the navigation system 20 illustrated in FIG. 1, can be used to navigate a procedure relative to a patient 26. As discussed in detail herein, various instruments can be moved relative to the patient 26 and tracked relative to the patient 26. Although an image-guided system can include acquiring image data of the patient 26, such as with an imaging device 28, the imaging device is not required, as discussed herein. A portion of the patient's 26 anatomy can be mapped by identifying a plurality of points within the patient 26 by determining a relative location of an instrument. The plurality of points can be illustrated individually, or sequentially, or a surface can be illustrated over or without the plurality of points to illustrate or identify a portion of the anatomy of the patient 26. The discussion herein may refer to map data or map data points and will be understood to include individual acquired data points, illustrated individual or managed points an algorithm process applied to acquired data points to improve visual display by eliminating regions of especially high density and useful in modulating characteristics of rendered surfaces, a rendered surface, or any appropriate manner of illustrating the acquired map data. Once the map has been created of the patient 26 or a portion of the patient 26, either with or without a surface rendered relative to the individual points, a procedure can be guided or navigated using the map data. The map data can be generated without other imaging information, such as image data that might be acquired with a fluoroscopic system, magnetic resonance imaging (MRI) System, computed tomography (CT) Imaging System, three-dimensional echo, ultrasound (2D, 3D, or 4D), or other imaging systems such as the imaging system 28.

Figure 10:
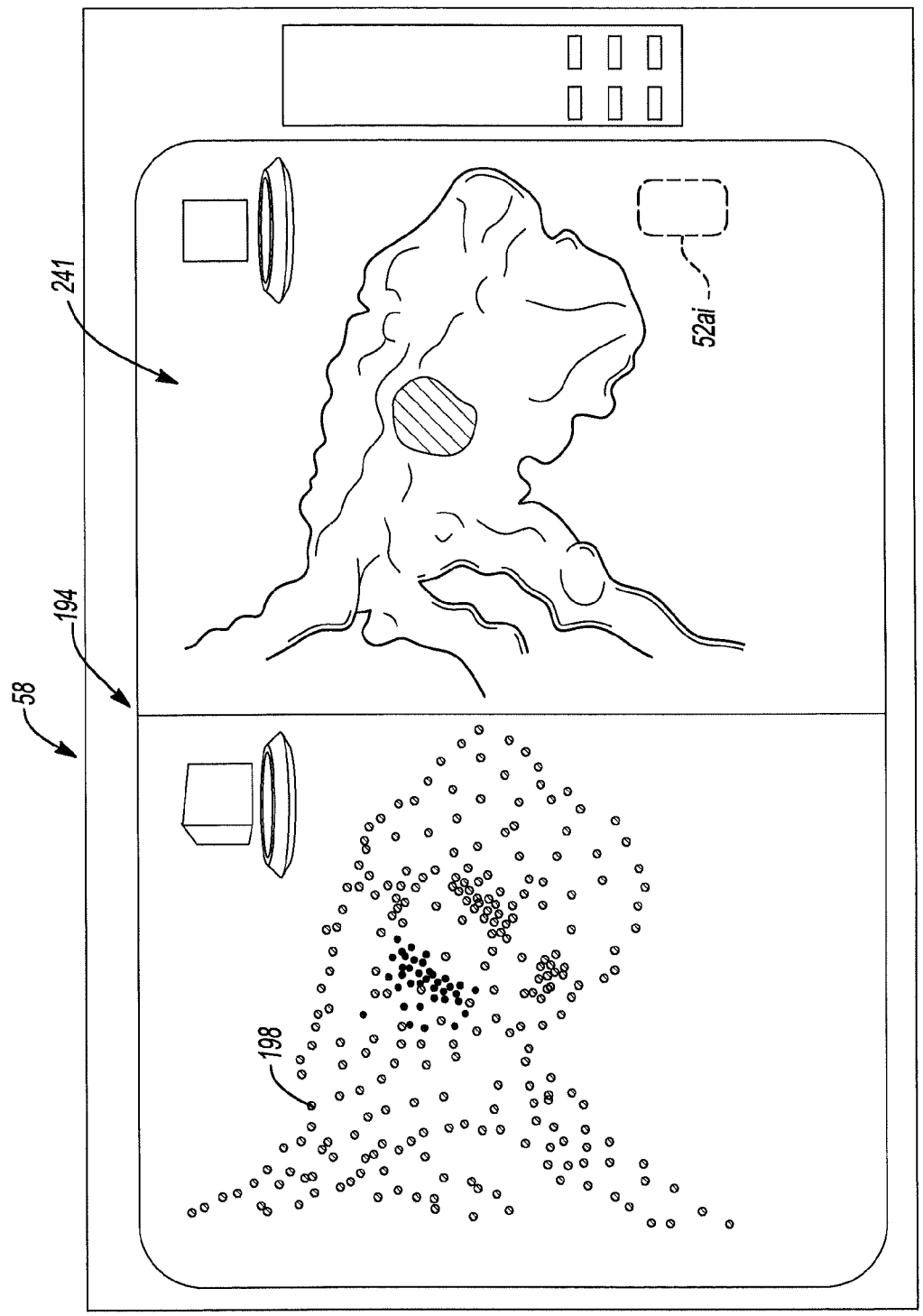
FIG. 10 is a display device illustrating raw mapping information and surface rendered data.

The map data that can be displayed, such as illustrated in FIG. 10, can be used to identify various anatomical features. In addition, instruments can be navigated relative to the patient 26 using the map data. Identification of implants, ablation or cannulation procedures, or other procedures can be performed. Accordingly, a procedure can be navigated and performed substantially precisely with the generated map data. A display device can be used to display the map data and/or illustrate icons representing various portions or reference points relative to the patient 26. For example, an icon can represent a position of the instrument relative to the patient 26. In addition, the map data can be generated in a substantially three dimensional or even four dimensional manner. Accordingly, the display can include a three dimensional viewing, simulated three dimensional viewing, or even four dimensional viewing, such as to illustrate a change in the patient 26 over time.

The map data can be generated or acquired with any appropriate system. As discussed herein, a position sensing unit (PSU) can acquire multiple points of or within the patient 26. The PSU system can measure voltage, bioimpedance, acoustic (e.g., sound and ultrasound), time-of-travel, magnetic field strengths, or any appropriate characteristic.

It will be understood, however, that the navigation system 20 can be used to navigate a procedure relative to the patient 26 without using image data generated by another imaging system, such as a fluoroscopic imaging system, other than the PSU 40. Although image guided navigation is generally known in the art. The display can include the map data which includes one or a plurality of points that are determined or generated by tracking a position element or device within or relative to the patient 26. The position element can be associated with, connected to, or include an instrument that is tracked with any appropriate tracking system, such as a bio-impedance, electromagnetic, optical, acoustic, or other appropriate tracking system. As discussed further herein, the map data can be used to generate or render a surface to more clearly or selectively illustrate or identify various anatomical features and locations within the patient 26.

With further reference to FIG. 1, the navigation or mapping system 20 can be operated by a user 22 with an instrument 24 to map a selected space, such as a portion of the patient 26. The instrument 24 can also be navigated relative to the patient 26. The instrument 24 can be moved relative to the patient 26 for various procedures, including lead (e.g. temporary or permanent implantable cardiac pacing leads, with insulated wiring for stimulating and/or recording signals in or on the heart) placement relative to the heart, mapping of the heart, mapping of a selected organ of the patient 26, or guiding or navigating the instrument 24 relative to any appropriate portion of the patient 26.

The navigation system 20 can include various components, such as the optional imaging device 28. The optional imaging device 28 can include a fluoroscope, such as a fluoroscope configured as a C-arm. The C-arm fluoroscope can include an imaging section 30 and a x-ray emitting section 32. The imaging device 28 can be controlled by a controller 34. Images acquired with the imaging device 28 can be displayed on a display device 35 that is associated with the imaging device 28. It will be understood, however, that the separate display device 35 is not required. In addition, if the imaging device is an x-ray imaging device any radio-opaque portions will appear as a part of the image when viewed, including the instrument 24. Further, other imaging systems, such as ultrasound, can be used to image the patient 26 and may also include information regarding instruments within the imaging field of the ultrasound transducer.

The controller 34 can control the imaging device 28 and can store images generated with the imaging device 28 or transmit data or receive instructions via a data transmission line 36 to or from a processor and/or memory, such as one that may be included in a workstation 38. While the optional imaging device 28 illustrated here is a fluoroscopic c-arm other imaging devices, such as CT, MRI, ultrasound, etc., can also be employed. Moreover, it will be understood that the communication line 36 can be any appropriate communication line such as a wired communication line, a wireless communication system, or any other data transfer mechanism.

Figure 2:
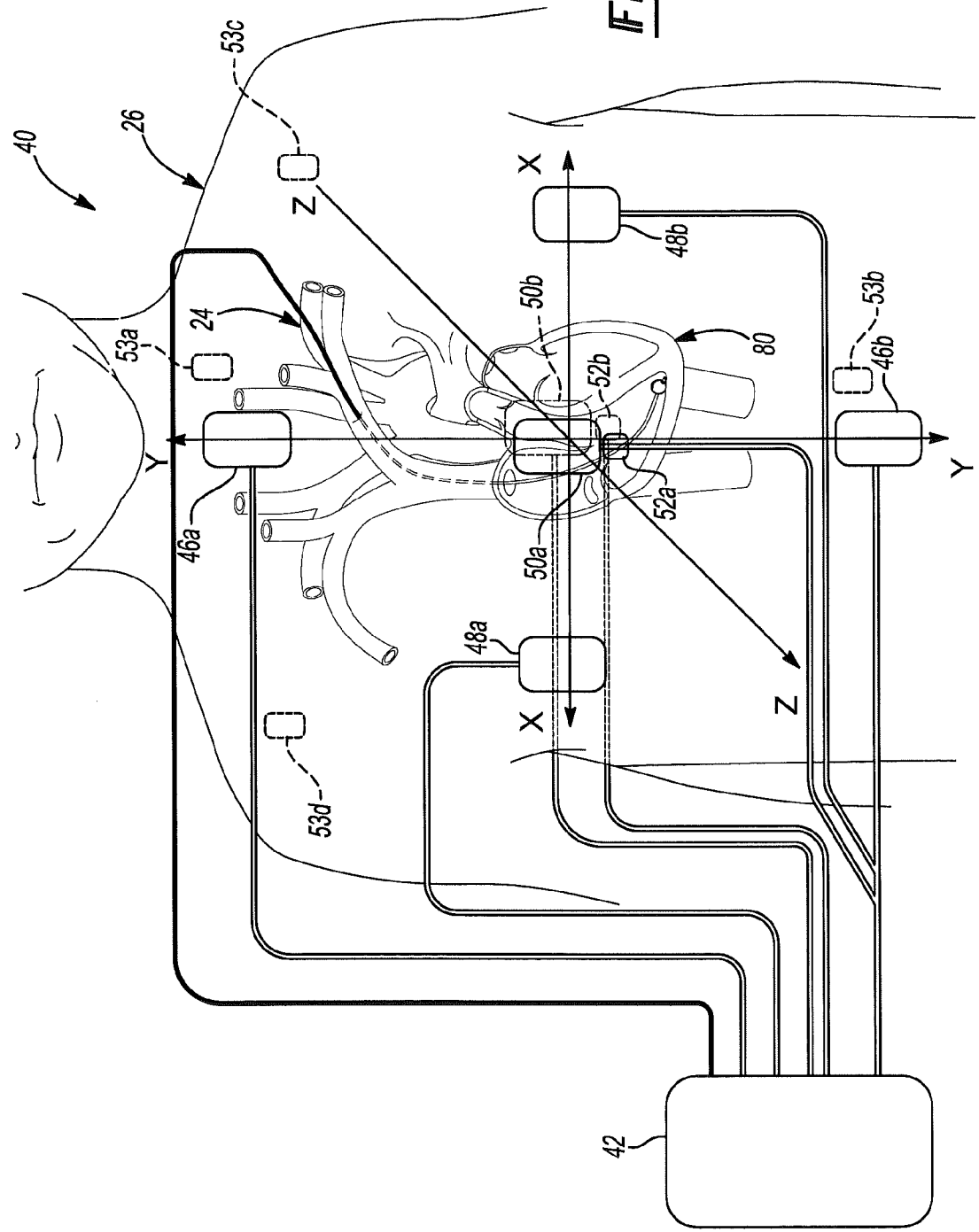
FIG. 2 is a detailed view of a position sensing unit (PSU) and associated devices, according to various embodiments.

The navigation system 20 can further include a Position Sensing Unit (PSU) 40 as illustrated in FIG. 2. The PSU 40 can include an impedance or Electrical Potential (EP) system. The PSU can be the LocaLisa® Intracardiac Navigation System as previously provided by Medtronic, Inc. of Minneapolis, Minn., USA. The PSU 40 can also include any appropriate tracking system such as an electromagnetic (EM) or optical tracking system. An exemplary EM tracking system can include the Stealthstation® Axiem® electromagnetic tracking system and an exemplary optical tracking systems include the Stealthstation® TRIA® optical tracking system, both sold by Medtronic Navigation, Inc. having a place of business in Colorado, USA.

Bio-Impedance Position Sensing Unit

If the PSU 40 includes an EP tracking unit it can include a control or driving unit 42 that includes one or more input or output connectors 44 to interconnect with a plurality of current conducting or drive patches connected directly with the patient 26. The current patches can include patches to create three substantially orthogonal voltage or current axes within the patient 26. For example, a first y-axis patch 46a and a second y-axis patch 46b can be interconnected with the patient 26 to form a y-axis (such as an axis that is generally superior-inferior of a patient as illustrated in FIG. 2) with a conductive path such that the conducted current establishes a voltage potential gradient substantially along this axis and between the patches 46a and 46b. A related y-axis current flows from the first y-axis patch 46a to the second y-axis patch 46b substantially along the y-axis. Likewise, a first x-axis patch 48a and a second x-axis patch 48b can be connected with the patient 26 to create a x-axis (such as an axis that is generally medial-lateral of a patient) with a voltage gradient substantially along the x-axis between the patches 48a and 48d and a corresponding x-axis current flowing between patches 48a and 48b. Finally, a first z-axis patch 50a and a second z-axis patch 50b can be connected with a patient 26 to create a z-axis (such as an axis that is generally anterior-posterior of a patient) with a voltage potential gradient substantially along the z-axis between the patches 50a and 50b with a corresponding z-axis current flowing between the patches 50a and 50b. The three axes are generally formed to have an organ or area of interest that the common intersection or origin of each of the axes x, y, z. Accordingly, the patches 46-50 can be positioned on the patient 26 to achieve the selected placement of the axes x, y, z relative to the patient 26. Each of the patches 46a-50b can be interconnected with the PSU input/output (I/O) box 42, via a wire connection or other appropriate connection at the ports 44.

The current applied between the related patches generates a small or micro-current, which can be about 1 microampere (μA) to about 100 milliamperes (mA), in the patient along the axis between the respective patch pairs. The induced current can be of a different frequency for each of the related patch pairs to allow for distinguishing which axis is being measured. The current induced in the patient 26 will generate a voltage gradient across different portions, such as the heart, that can be measured with a position element. The position element can be an electrode, as discussed in further detail herein. The sensed voltage can be used to identify a position along an axis (whereby each axis can be identified by the particular frequency of the current being measured) to generally determine a position of an electrode along each of the three axes. Although a voltage can be sensed, an impedance can also be calculated or measured to determine a location in a similar manner. It will be understood, that a sensing of voltage will not eliminate other possible measurements for position determination, unless specifically indicated. As discussed further herein, the position of the electrode with respect to each of the three axes can be used as map data to be illustrated on the display device 58. Position elements can be electrodes within the patient and reference electrodes are interconnected with the PSU I/O box 42 such that the signals are processed by high impedance circuitry so as to not load and distort the sensed signals.

In addition, reference patches can be interconnected with the patient 26 for reference of guiding or mapping with the instrument 24 relative to the patient 26. The reference patches can include a first reference patch 52a and a second reference patch 52b. The placement of the reference patches 52a, 52b can be any appropriate position on the patient 26, including those discussed further herein according to various embodiments. For example, the first reference patch 52a can be positioned substantially over the xiphoid process on the skin of the patient 26 directly exterior to the xiphoid process of the patient 26. The second reference patch 52b can be positioned substantially directly across from the first patch 52a on a dorsal surface of the patient 26.

By positioning the reference patch 52a at the xiphoid process of the patient 26, the reference patch 52a has relatively less motion with respect to the heart than many other locations on the skin of the patient 26. The heart 80 of the patient 26 is substantially static in position relative to the xiphoid process. By positioning the reference patches 52a,b at these locations, respiration may be monitored by measuring the relative voltage or impedance difference between the two reference electrodes 52a, b using the PSU 40. As discussed herein, impendence or voltage measured between the two reference patches 52a,b can be used to determine a respiratory cycle and the portion of the cycle that the patient 26 is in. Also, the reference patches 52a,b can be used to assist in cardiac cycle monitory in a similar manner.

The PSU I/O box 42 can be interconnected with the workstation 38, via a connection or data transfer system 56. The data transfer system 56 can include a wire transmission, wireless transmission, or any appropriate transmission. The workstation 38 can receive signals, which can be analog or digital signals, regarding voltages sensed by the reference patches 52a, 52b and electrodes on the instrument 24. The signals can be used to determine a relative location of the instrument 24 and to display the determined relative location on the display device 58. The display device 58 can be integral with or separate from the workstation 38. In addition, various interconnected or cooperating processors and/or memory can be provided to process information, each may be a part of the workstation 38 or separate therefrom. The processors can process the signals from the patches 46-52 and instrument 24 to determine the position of the instrument 24, display the determined positions or other data on the display device 58.

The navigation system 20 can further include user input or data input devices such as a keyboard 60, a joystick 62, or a foot pedal 64. Each of the input devices, 60-64 can be interconnected with the workstation 38 or appropriate systems for inputting information or data into the workstation 38. This information or data can include identifying appropriate information, as discussed further herein, such as various components, or anatomic regions.

With continuing reference to FIGS. 1 and 2, with particular reference to FIG. 2, the multiple driving or voltage patches 46a-50b are used to conduct current in the patient to create voltage potentials within the patient 26 that can be sensed by electrodes that are positioned on or within the patient 26. It will be understood that the driving patches 46-50 can be positioned on the patient 26 at any appropriate locations, such as the locations described with the Local Lisa™ position sensing unit previously provided by Medtronic, Inc. of Minneapolis, Minn., USA. The PSU I/O box 42, can create voltages and generate a small current along the axes between the related patches. The current generated can include different frequencies along the different x, y, and z axes to distinguish the x, y, and z-axes.

The instrument 24 can include an electrode, as discussed further herein, which is able to sense the voltage generated within the patient 26 due to the patches 46a-50b positioned on the patient 26. The sensed voltage can be used to calculate an impedance of the tissue in the patient 26 based upon the voltage potential gradient generated between the respective pairs of patches and the corresponding current. Generally, the current is carried due to an electrolyte in the patient 26, such as blood, interstitial fluid, etc. within a heart 80 and body of the patient 26.

Tracking References

As discussed further here, the calculated impedance or sensed voltage can be used to determine a location of the electrode of the instrument 24 relative to a selected reference, such as reference patch 52a or 52b. The reference patches 52a, 52b can be positioned at any appropriate position on the patient 26. As discussed above, the first reference patch 52a can be positioned substantially over the xiphoid process of the patient 26. The positioning of the first reference patch 52a over the xiphoid process of the patient 26 can limit movement of the reference patch 52a due to respiration or cardiac movement. The reference patches 52a, 52b can also be used for repeat or multiple procedures at different times. For example, the reference patches can be used to reorient or register the mapping data 194 to the patient 26 at a second time, such as during a later procedure. Therefore, the reference patch 52a can be a substantially fixed reference patch for reference regarding the voltage generated by the PSU 40.

The second reference patch 52b can be positioned substantially directly across the thickness of the patient 26 on a dorsal side of the patient 26 from the first reference patch 52b. The two reference patches 52a, 52b can be on the same horizontal plane. The horizontal plane is perpendicular to the coronal or median planes of an anatomy. The second reference patch 52b can also be substantially fixed relative to the patient 26, at least in part because it is positioned on the dorsal side of the patient 26 and the patient is supine for the procedure of lead implantation.

In addition, the second reference patch 52b can be used to reorient or continue reference of the data acquired with the electrodes of the instrument 24 if the first reference patch 52a is removed. For example, during a procedure an emergency may require the removal of all of the patches from a ventral side of the patient 26, including the first reference patch 52a. After the treatment of the emergency, however, the data acquired with the instrument 24 can be reoriented relative to the patient 26 or relative to the instrument 24 using the second reference patch 52b. Also, the second reference patch can be used to continue mapping and provide a reference even if the first reference patch 52a is not repositioned. Accordingly, use of at least two reference patches 52a, 52b can assist to reference the mapping data acquired relative to the patient 26.

The PSU 40 including the several patches can inject a current into the patient 26. The current that is injected can be a substantially stable current that is not substantially changed over time. If the current is substantially stable then a voltage can be measured with an instrument or reference patch, as discussed herein and above, to be used in determining a location of the instrument or the reference patch relative to the axis on the patient 26. Alternatively, or in addition thereto, an impedance can be determined based upon a measured current that is injected in the patient and the measured voltage with the instrument reference patch. The impedance can, therefore, be used to determine a location of the instrument or the referenced patch. Accordingly, it will be understood that the position of an electrode, such as of an instrument, can be determined based upon a relationship of Ohms Law by determining an impedance or measuring voltage within the patient or any appropriate volume 26.

It will be further understood that the PSU 40 can be understood to be an imaging system. The imaging system or image acquisition of the PSU 40, however, can be based upon the determination of multiple points within the patient 26 and illustrating or displaying the points or a surface relative to the points on a display device. The PSU 40 can be used alone without any other imaging devices. Other imaging devices may include those that are external to the patient or positioned within the patient to generate a field of view, such as an MRI, CT or an ultrasound of the patient.

In addition to electrodes being positioned on or near a xiphoid process of the patient 26, various reference electrodes can be positioned at other locations on the patient. For example, as illustrated in FIG. 2, other locations on the patient 26 can include positions superiorly, such as exemplary reference patch 53a, inferiorly, such as at the illustrated position of patch 53b, or any appropriate quadrant such as an upper left or upper right, reference patch locations 53c and 53d. Each of the reference patches, including the xiphoid reference patch 52a and the other patches 53a-53d can include respective anterior and posterior patch pairs. In addition, each of the reference patch pairs can be connected to the PSU I/O box 42. Thus, measurements can be made with the various reference patches 52a-b and 53a-d and provided to the PSU 40 of the navigation system 20.

As discussed above, the xiphoid reference electrodes 52a, 52b can be used for various purposes. For example, the xiphoid reference electrodes 52a, 52b can be used to reference the position of the mapped data, as exemplarily illustrated in FIG. 10, with reference icon 52ai relative to the reference electrodes 52a, 52b. Similarly, the additional reference electrodes 53a-53d can also be used to orient the map data. This can be useful for example, if the mapping or tracked instrument is moved within the patient 26 and temporary localization or tracking is lost, for example, if a connection is lost between the instrument and the PSU I/O box 42. Upon reacquiring a signal between the instrument and the PSU I/O box 42 the reference electrodes 52a, 52b, or any of the other reference electrodes 53a-53d can be used to reorient the illustrated map data relative to the tracked instrument and the reference electrodes 52a-b, 53a-d.

The reference electrodes, whether the xiphoid reference electrodes 52a, 52b or the other reference electrodes 53a-53d can be illustrated relative to the mapped data such as including the surface rendering 241. For example, the surface rendering 281 can represent a portion of the anatomy, such as a right ventricle. The xiphoid reference patch 52a can be positioned on the patient 26 at the xiphoid process which is at a selected physical location relative to the right ventricle of the heart 80. Accordingly, the position of the reference electrode 52a can be illustrated on the display 58 as a reference mark 52ai. Accordingly, the reference electrodes, such as the xiphoid reference electrode 52a, can be used as a tracked portion or illustrated icon on the image display 58. Similarly, the reference electrodes 53a-53d can be illustrated at specific locations relative to the map data on the display device 58 to provide a reference for the displayed map data relative to the patient 26. The reference electrodes, including the xiphoid electrode pair 52a, 52b and the other reference electrodes 53a-53d can be tracked along or with the tracking electrodes 56a-56b. Such as the instruments that are tracked within the heart 80 of the patient 26. Accordingly, the position of the various reference electrodes 52a, 52b, and 53a-53d can be tracked using the tracking or localization system PSU 40.

Reference patches can also be used to measure a voltage drop of the tissue patch interface. Patches driven with current have a voltage drop across the electrode tissue interface. Using raw unreferenced voltage introduces measurement error which is eliminated by use of a reference. The reference electrodes can be used to measure the voltage drop.

Mapping Catheter

Figure 3:
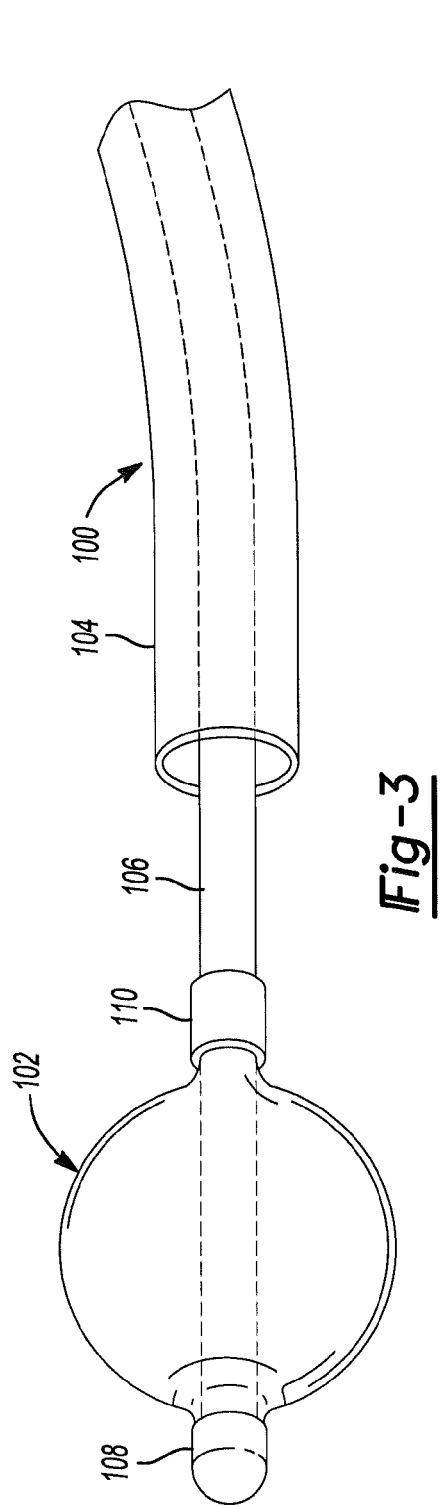
FIG. 3 is a detailed view of a mapping catheter according to various embodiments.

With reference to FIG. 3, according to various embodiments, a mapping or navigation catheter 100 can be used as the instrument 24. The mapping catheter 100 can include various portions, such as a balloon or inflatable portion 102. The inflatable or expandable portion 102 can be part of a catheter system, such as a Swan-Ganz Balloon Catheter System sold by Edwards Lifesciences REF: D97120F5 (5F)] and generally known in the art.

The mapping catheter 100 can further include a sheath 104, which can be deflectable. A lead or catheter defining a lumen 106 can extend through the sheath 104 and through the balloon 102. A tip or first electrode 108 can be provided on a distal end of the catheter 106 and a ring or second electrode 110 can be provided on a proximal end of the balloon portion 102. This can provide at least two electrodes to sense a voltage within the patient 26 when the mapping catheter 100 is positioned within the patient and the current patches are being driven. As discussed further herein, the electrodes 108, 110 can sense a voltage produced within the patient 26 and from the sensed voltage an impedance can be calculated to determine a location of the mapping catheter 100, as discussed further herein.

In addition, during mapping, the balloon portion 102 can assist in assuring that the catheter 106 does not puncture, lacerate or perforate a wall of the heart 80 or other blood vessel. The balloon portion 102 can also act as a stop when the mapping catheter 100 is being moved through the heart 80 or other anatomical portion. The balloon portion 102 can be inflated or deflated as selected by the user 22. Inflation of the balloon portion 102 can be performed in any appropriate manner such as directing a fluid, such as a liquid or gas, through the catheter 106. In addition, the mapping catheter 100 can be moved relative to the patient 26 in any appropriate manner, such as a steering mechanism (not particularly illustrated) or via anatomical forces placed upon various portions of the catheter 100, such as a drag created on the balloon portion 102 by the flow of blood. Further, various conductors can be used to transfer the sensed voltage from the electrodes 108, 110 to the PSU I/O box 42.

Lead Instrument

Figure 4:
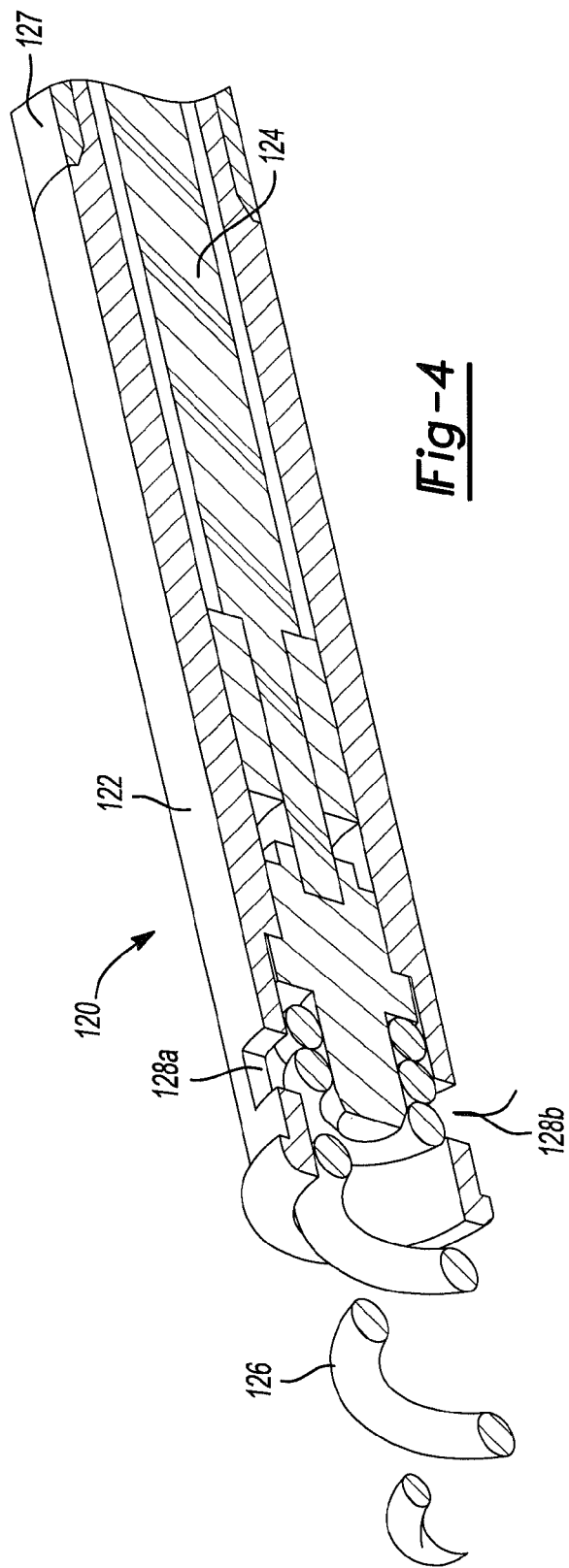
FIG. 4 is a detailed view of an implantable retractable lead with a retractable electrode, according to various embodiments.

With reference to FIG. 4, a lead 120 is illustrated that can also be used as the instrument 24. The lead 120 can be any appropriate lead such as the model 5076 sold by Medtronic, Inc. of Minneapolis, Minn., USA. The lead 120 can be used as part of an implantable medical device 300 (illustrated in FIG. 13), but need not generally be used to acquiring mapping data. The position of the lead 120, can be determined and displayed on the display device 58, as discussed further herein. The lead 120 can include an external sheath or covering 122 that substantially insulates an interior of the lead 120 from an external environment, such as an anatomical portion. The lead 120 can include a conductor 124 and a retractable helix electrode 126. The electrode 126 can be used with the PSU 40 to determine the location of the electrode 126. However, generally during insertion and placement of the lead 120, the electrode 126 is substantially retracted into the covering 122 of the lead 120. Accordingly, an appropriate or strong signal of the voltage may not be efficiently determined in the retracted state. This may be because the signal may have high source impedance when the electrode is retracted and voltage measurements may be misleading. Therefore, an opening, which can include one or more portals or windows 128a, 128b can be formed in the covering 122 to allow an electrolyte to contact the electrode 126 while moving the electrode 126 through the patient 26. A voltage can be efficiently sensed by the exposed electrode 126 through the window portions 128a, 128b.

As discussed herein, the determined position of the lead 120 can be illustrated on a display device relative to data collected either with the lead 120 or with the mapping catheter 100. Accordingly, the sensed voltage through the window 128 can be used to determine a position of the lead 120 relative to the mapping data. It will also be understood, the lead 120 may include more than the implantable electrode 126. The lead 120 may include at least a second electrode, such as a ring electrode 127. A voltage can also be sensed by the ring electrode 127 and also be used for determining a position of the lead 120 or a portion thereof.

Catheter Opening or Passage

With reference to FIGS. 4A and 4B, a lead 140, according to various embodiments, can include a moveable window covering portion 142. The cover 142 can move with the electrode 126 as the electrode 126 is moved out of the covering sheath 122. As illustrated in FIG. 4A, when in the retracted configuration the windows 128a, 128b are uncovered to allow an electrolyte to contact the electrode 126 over a large surface area which lowers impedance of the circuit. As illustrated in FIG. 4B, when in the extended configuration the windows 128a, 128b are covered by the window covering 142 which blocks access to the electrode 126 though the windows 128a, 128b.

Accordingly, the cover 142 can move from a non-covering or opened position to a covering position relative to the window 128 when the electrode 126 is deployed or extended. The cover 142 can cover the window 128 to ensure that a material, such as blood or other material does not enter the cover 122 after extension of the electrode 126. It will be understood that providing the cover 142 may not be necessary for appropriate operation of the lead 120 with an implantable medical device.

Display Map Data Points

Figure 5:
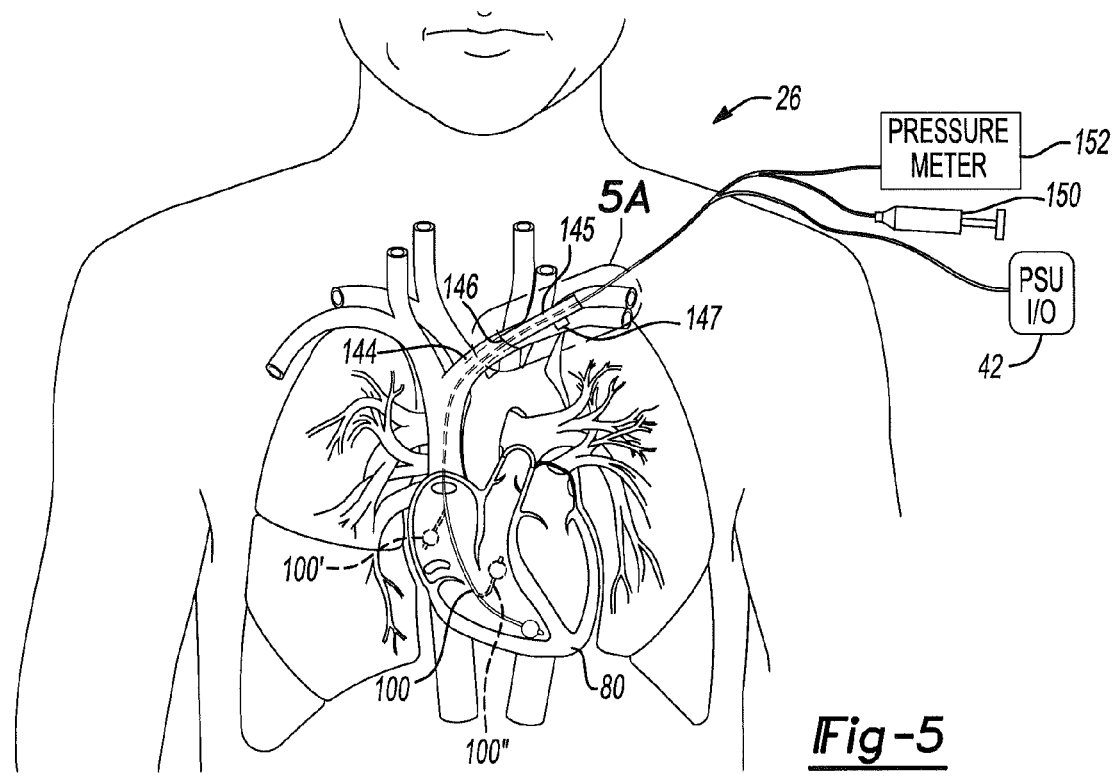
FIG. 5 is a view of a patient with a mapping catheter inserted into an internal organ of the patient.

With reference to FIGS. 1-3 and further reference to FIGS. 5 and 6, a selected map data 194 of an anatomical region, such as a heart 80 can be produced. The map data 194, as illustrated in FIG. 6, can be generated using only the PSU 40. Thus, the map data 194 can be considered without reference to an external imaging device or other imaging device. A surface or virtual image, however, can be generated as discussed herein.

As discussed above, the heart 80 includes an electrolyte, such as blood, which can be used to allow the sensing of a voltage or bio-impedance with an electrode, such as the electrodes 108, 110 of the mapping catheter 100 or electrode 126 of the lead 120. The voltages sensed by the electrodes 108, 110 are generated by the currents conducted through patches 46a-50b, as particularly illustrated in FIGS. 1 and 2 and removed from FIG. 5 for clarity. The patches positioned on the patient 26 create virtual axes within the patient 26 of induced voltage gradients. A determination of a position of the electrode can be made by sensing the voltages or determining impedance within the patient while the current is conducted in the patient 26. The particular voltage or impedance sensed or determined is based upon a location of an electrode in the patient 26. The electrodes 108,110 of the mapping catheter 100 can sense the voltage of each of the three axes to determine a three dimensional position of the mapping electrodes 108, 110 within the patient 26. Similarly, the electrodes of the leads 120, 140 can be used to sense the voltages in the three axes to determine the position of the electrodes within the patient 26. The mapping catheter 100, including the electrodes 108, 110, can be moved through various portions in the patient 26 while the electrodes sense the voltages, substantially continuously or as selected, among the three axes to determine multiple three dimensional positions of the electrodes.

A selected number of position measurements or determination can be made, such as manual selection or automatic selection at selected time intervals. The sensed voltages can then be used to determine a relative position of the electrodes, as discussed herein. In addition, such as when the two electrodes 108, 110 are provided, a direction of the catheter 100 can also be determined. For example, a location of both of the electrodes 108 and 110 can be made. Based upon this determination a determination of direction of the catheter 100 or orientation of the catheter can be made based upon the two location or position determinations. It will be understood, that a similar direction determination can be made regarding any appropriate catheter with at least two electrodes positioned along its length.

As discussed above, the mapping catheter 100 can include the Swan-Ganz catheter which can include a syringe or similar device 150 to inject a fluid or gas to inflate the balloon 102. A pressure meter or sensor 152 can also be interconnected with the lead that is within the balloon 102 to sense a pressure placed on the balloon 102 when the balloon is within the patient 26. For example, once the balloon 102 is inflated, such as when the balloon 102 is positioned exterior to the sheath 104, a pressure induced on the balloon 102 will be transmitted through the catheter 106 and can be measured with the pressure meter 152. It will be further understood, however, that a pressure meter or transducer can also be positioned at any appropriate location, such as within the balloon 102. As discussed further herein, the measurement of a pressure pulse or a pressure change can be used to identify various regions of the heart 80 by the user 22. In this regard, an increase or change in pulsative pressure can be used to identify regions of the heart such as the right atrium, right ventricle, pulmonary artery, and the locations of valves.

The mapping catheter 100 can be introduced into the patient 26 via any appropriate method to collect map data. Returning reference to FIG. 5A, the catheter 100 can be positioned in a vein 144 of the patient 26 through an incision 146 made in the dermis of the patient 26 and an introducer 145. Other appropriate mechanisms can also be used to introduce the mapping catheter 100 into the vein 144. The introducer 145 can be any appropriate introducer, such as the introducer HLS-1007 sold by Pressure Products, Inc. having a place of business in San Pedro, Calif., USA. The introducer 145 generally provides a semi- or substantially rigid opening for introducing or moving the catheter 100 into the patient 26. The introducer 145 can include an opening that includes a diameter of a selected dimension larger than an external diameter of the catheter 100. The opening in the introducer 145 can generally be defined a throughbore or cannula extending from a first end to a second end of the introducer 145. An instrument, such as the mapping catheter 100, can be passed through the instrument introducer 145.

The introducer 145 can be tracked relative to the patient and to the mapping catheter 100 with any appropriate mechanism. For example, the introducer 145 can include an electrode 145a that can be tracked or have its position determined by the PSU 40. As discussed above, the position of the mapping catheter 100 can be identified or determined with the PSU 40 using a measured voltage or impedance at the electrode. The electrode 145a of the introducer 145 can operate substantially identically and have its position determined with the PSU 40.

Figure 5A:
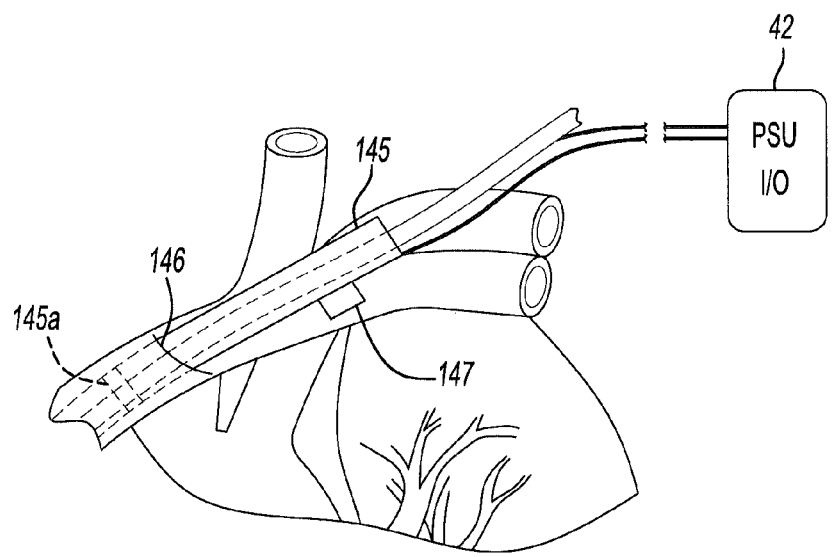
FIG. 5A is a detailed view of a mapping catheter inserted in a patient.

It will be understood that any appropriate tracking system, however, can also be used to track the location of the introducer 145. For example, an electromagnetic, optical, acoustic, or any appropriate tracking system can be used to track at least a portion of the introducer 145. As illustrated in FIG. 5A, a tracking device 147 can be interconnected with the introducer 145. Tracking the tracking device 147 can allow for a determination of a position of the introducer 145 relative to the patient 26 using a tracking system that can be separate or additional to the PSU 40.

Various navigation or tracking systems can include those disclosed in U.S. Patent Application Publication No. 2008/0132909, assigned to Medtronic Navigation, Inc., and incorporated herein by reference. According to various embodiments, image data of the patient 26 can be acquired prior to a procedure and the image data can be registered to the patient 26 according to appropriate methods and with appropriate devices. Therefore, the introducer 145 including the tracking device 147 can be tracked and navigated, such as with the image data of the patient 26, to position the introducer 145 at a selected location relative to the patient 26. Also, the introducer 145 can be navigated relative to the map data 194 generated of the patient 26.

Figure 7:
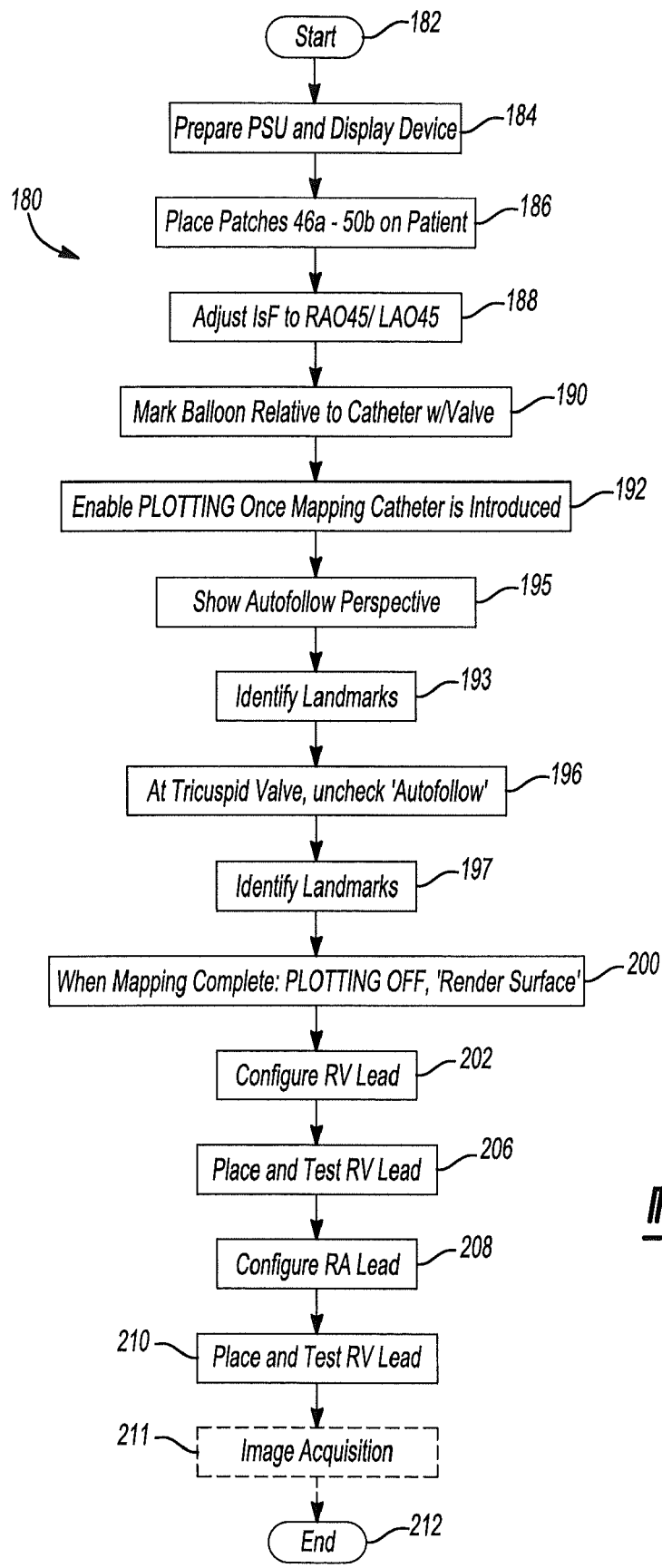
FIG. 7 is a flow chart illustrating a method of mapping with a position sensing unit.

With initial reference to FIG. 7, a procedure 180 is illustrated that can use the position sensing unit 40, its associated patches interconnected with the PSU I/O box 42, the mapping catheter 100, and the lead 120 to map and determine a position of the lead 120 in the patient 26 without the need to employ an external imaging device. The procedure 180, as briefly discussed here, can include creating a map of a portion of the patient 26 and positioning leads within a portion of the patient 26. It will be understood that although the procedure 180 is discussed relating to a cardiac procedure, other appropriate procedures can be performed by positioning the mapping catheter 100, current patches and reference electrodes in different portions of the patient 26. For example, a map can be made of other areas, such as gastrointestinal areas, pleural areas, or other areas of the anatomy of the patient 26 including an electrolyte material. Accordingly, the procedure 180 can be modified in an appropriate manner to be used with an appropriate procedure.

The procedure 180 can start in start block 182. The procedure 180 can then proceed to preparing and configuring the position sensing unit and a display device, as illustrated in FIG. 1. Preparing the PSU in block 184 can include various steps, such as labeling the patches for positioning on the patient 26, interconnecting the patches with the PSU I/O box 42, the workstation 38 with the PSU I/O box 42, and other appropriate steps.

After the PSU 40 is prepared in block 184 and the patches 46a-50b can be positioned on the patient 26 in block 186. In addition, the reference patches 52a and 52b can be positioned on the patient 26 as well in block 186. The patches 46a-52b can be positioned on the patient 26 as illustrated in FIGS. 1 and 2. Positioning of the patches on the patient 26 allows for the position sensing unit 40 to generate potentials within the patient 26 that can be sensed with the electrodes 108, 110 of the mapping catheter and electrodes of the lead 120. The patches 46-52 can be attached on a skin surface of the patient 26. This can allow for efficient generation of the current in the patient 26.

The current can be any appropriate amount. For example, the current injected along the various axes can be about 1 µA to about 100 mA. As a specific example, the current may be a current that is about 1 µA. Such a micro-current, however, may not always be injected exactly at 1 µA, but may vary by 1%, 2%, 5% or any acceptable percentage. Determining an impedance may assist in obtaining a precise or accurate position. Determining an impedance is based on a sensed voltage at a known or measured current. Also, determining an impedance rather than a voltage may adjust and account for differences in current between the three orthogonal axes. Thus, a changing or inconstant current can be used to determine a precise impedance for position determinations. Generally both sensing a voltage and/or determining an impedance can be referred to as evaluating an electrical property, such as for position determination.

The display device 58 and its associated controller or processor can then be adjusted to illustrate or display a right anterior oblique (RAO) and a left anterior oblique (LAO) view in block 188 and as particularly illustrated in FIG. 6. The two oblique views can illustrate for the user 22 views of the data mapped of the patient 26 that can be generally similar to fluoroscopic or x-ray images otherwise acquired of the patient 26. However, because no imaging device is necessary to form the images, the view of the patient 26 or access to the patient 26 is not obstructed by the imaging device 28. As illustrated in FIG. 6, a legend cube 98 can be used to identify the view angles being represented. As discussed above, the use of the mapping catheter 100 and the position sensing unit 40 can eliminate or substantially reduce fluoroscopic imaging of the patient 26, while maintaining an appropriate level of location identification of various portions, such as the lead 120 within the patient 26. It will be understood, however, that any appropriate viewing angles can be displayed on the display device 58, the oblique views are merely exemplary.

Display Reference

Even with a reference cube and known display orientation, reference to a physical location of the patient 26 can be useful for orienting the display 58 to the patient 26. Thus, the display 58, shown in FIG. 6 can also be used to selectively display information in addition to the mapping and data points 198. Icons 46a', 46b' can show the pseudo location of the axes patches of the PSU 40. The pseudo location of the patches shown by icons 46a', 46b' or other patches can be based upon relative positions of the axis patch electrodes 46a-50b. That is because the axis patch electrodes 46a-50b inject current and are not inputs into the PSU 40 so that their position can be determined with the PSU 40. The patch electrodes 46a-50b are positioned on the patient 26 according to an appropriate manner. For example, as illustrated in FIG. 2 above, the patches can be positioned on the patient to generate axis x, y, and z currents. The patches 46a-50b that are positioned on the patient 26 can also be used to orient the data illustrated on the display 58. For example, the user 22 can select to illustrate or show the patches on the display 58.

As illustrated in FIG. 6, selected patches can be displayed. To better illustrate the orientation of the data on the display device 58 relative to the patient 26, the user 22 can select to have the icons 46a', 46b' displayed to represent the relative physical location of the patches 46a, 46b. Because the patches 46a, 46b are physically on the patient 26, the user 22 can be oriented on the display device 58 relative to the patient 26. It will be understood that the PSU 40 can have an input to allow the user to select to show the patches as icons on the display 58 or not show the patches as icons on the display 58.

The position of the patches illustrated as icons on the display 58, such as the two patch icons 46a' and 46b' can be determined based upon the position of the map point data 198. As discussed herein, the map point data 198 is determined by measuring a voltage or bioimpedance based upon a current generated between pairs of patches 46a-50b. Accordingly, the determination of the location of the electrode being used to measure the voltage can also be used to determine the position of the patches relative to the measured voltage for determining an appropriate location for illustrating the patch icons on the display 58. In a similar manner, the relative positioning of the reference electrodes 52a,b can be shown as icons 52a', b' on the display 58.

Returning reference to FIG. 7 of the collection of the map data is further discussed. The mapping catheter 100 can be prepared in block 190. For example, the catheter 106 can be marked relative to the sheath 104 for illustrating the position of the balloon 102 necessary to position the balloon 102 and electrodes just free of the sheath 104. This is generally a sterile procedure, and can be performed in an appropriate sterile manner.

The mapping catheter 100 can then be inserted or introduced into the patient in block 192. It will be understood that the mapping catheter 100 can be introduced into the patient 26 in any appropriate manner. Upon introduction into the patient 26, plotting of data points with the mapping catheter 100 can begin in block 192. The plotting of the data points can include illustrating data points on the display device 58, illustrated in FIGS. 1 and 6. The data points can be acquired substantially continuously or at a selected rate. The plotting of the data points can produce mapping data 194 that can be illustrated in any appropriate manner, such as a plurality of points 198 on the display device 58. The plurality of points illustrated on the display device 58 can be produced by moving the mapping catheter 100 through the heart 80, the veins of the patient 26, and other appropriate portions or moving mechanisms.

For example, once the balloon 102 has been inflated, drag is induced on the balloon 102, due to the flow of blood in the patient 26. This can assist the balloon 102 to move generally in the direction of the flow of blood in the patient and allow for ease of movement and guiding of the balloon catheter 100 within the patient 26. For example, the balloon catheter 100 can be introduced into the patient 26 and the flow of blood can direct the balloon catheter 100, from the right ventricle through the right ventricular outflow tract and into the pulmonary artery.

As illustrated in FIG. 6, the display device 58 can display a plurality of points that are acquired as the mapping catheter 100 is moved through the various portions of the patient 26. The plurality of points as the catheter 100 is moved through the patient, which is generally over time, allows for the creation of a map of the portion of the patient 26 through which the mapping catheter 100 is moved. As exemplary illustrated in FIG. 6, the display device 58 can illustrate the acquired mapping data 194 to illustrate appropriate portions of the heart 80.

The map data points 198 illustrated on the display device can also be managed for ease and efficiency of the user 22. For example, a selected density of data points 198 can be selected. Once a density threshold is reached a representative data point can be illustrated on the display device 58 rather than all acquired map data points that have been acquired with the mapping catheter 100. In other words, a representative data point 198 may actually represent more than one acquired position map point allowing fewer than all acquired position data points to be illustrated, but all can be used for rendering a surface, as discussed further herein. This can allow the map data 194 display to be selectively uncluttered with multiple overlapping map data point icons 198.

Landmarks can be identified in block 193 for display on the display device 58. Landmarks identified in block 193 can be any appropriate landmark and can be illustrated such as with a toroid 204 or a selected point, such as a point of a different color or shape 206 in the mapping data 194. The landmarks identified in block 193 can be any appropriate anatomical feature used as a landmark for a procedure. For example, an anatomical feature or landmark can include an ostium or opening, a valve, wall, or apex of the heart 80 or other portions of the patient 26 being mapped with the mapping catheter 100. The landmarks or further locations can be further limited based upon a determination of only the possible subsequent locations of the electrodes of the mapping catheter or lead. For example, from within the pulmonary artery the mapping catheter 100 or lead 120 can generally only move back into the right ventricle. Accordingly, the mapped points or the information regarding the same can be provided to the user 22 to limit the possible further or next positions.

The landmarks can include, as illustrated in FIG. 6, a first toroid 204a representing a junction of the inferior vena cava and the right atrium, a second toroid 204b representing a tricuspid valve, a third toroid 204c representing a pulmonic valve, and a fourth toroid 206d representing a junction of the superior vena cava and the right atrium. Other icons can also be used to represent landmarks, such as a triangle 206 that can represent an apex.

As various portions of the data are being acquired, the perspective or position of the virtual camera on the display device 58 can be changed. For example, during initial plotting of the data an auto-follow position can be illustrated, as selected in block 195. The auto-follow position allows the primary electrode or the electrode being tracked or the mapping electrode to remain at the center of the display device. The auto-follow position can move the virtual camera as illustrated on the display device 58 based upon speed of movement of the electrode being tracked or the location of the tracked or primary electrode relative to the position of the virtual camera. Thus, the view on the display device 58 can be based upon the position of the electrode relative to the virtual position of the camera.

The auto-follow feature can keep the tip of the primary electrode as the center of focus on display device 58. Rather than allowing the camera view to jump to wherever the electrode tip happens to be at a given point in time, the method works by smoothly transitioning to that point. The rate of the transition is dependent upon the distance between the current center of focus and the desired center of focus (the tip electrode's location). The set of rules define how the center of focus gets updated and can include moving the camera view at a speed proportional to distance to the tip or moving it immediately to the new desired position if the point of current focus is close to the new desired focus. These rules allow the transition to be rapid when necessary, while avoiding unnecessary and exaggerated movement when the camera is close to being centered.

At a desired point, the auto-follow position can be discontinued in block 196. When discontinued the view of the mapping data 194 can remain unchanged on the display device 58 as the electrode, such as the electrode 126 of the lead 120, is moved through the heart 80 and its relative position is displayed on the display device 58. The auto-follow feature, however, can be restarted to maintain the tracked position of the electrode near a center of the display device 58. Further landmarks can be identified in block 197 during or after any portion of the map data acquisition, such as after the tricuspid valve has been past or observed.

At an appropriate time a rendering of one or more of a point 198 in the mapping data 194 can be produced in block 200. The rendering can include a 3D rendered surface using the data points 198 in the mapping data 194. The mapping data 194 can be rendered, as discussed further herein, to illustrate or form a surface on the points 198 or relative to the points 198. The rendered data can be used to illustrate the mapping data 194 for appropriate purposes.

The map data can be rendered at any appropriate time. A user 22 can select that an appropriate amount of data has been selected or illustrated. Alternatively, or in addition to manual selection, the PSU 40 or other appropriate automatic processor can render a surface when appropriate amount of map data is collected with no additional input from the user 22.

Once an appropriate amount of data has been acquired and illustrated on the display device 58, a selected procedure can use the mapping data 194 acquired from patient 26. For example, various leads can be positioned within the patient 26, such as in a right ventricle or in a right atrium. Therefore, the procedure 180 can exemplary include configuring a RV lead in block 202. Configuring the RV lead in block 202 can include interconnecting the RV lead with the PSU I/O box 42 for guiding the RV lead, such as the lead 120, to a selected point in the patient 26 and configuring the PSU 40 to illustrate and display the RV lead as it is introduced and navigated through the patient. For example, as illustrated in FIG. 6, a graphical representation 120' of the lead 120 can be displayed relative to or superimposed on the mapping data 194. Illustrating a graphical representation of the lead 120 can allow the user 22 to understand the position of the lead 120 relative to the mapped data of the patient 26. The representation of the lead 120' can be displayed relative to the data points 198. For example, the data points can represent a 3D volume; accordingly the lead representation 120' may be partly obscured by some of the data points 198. The representation of the mapping data 194, however, can be rotated as selected by the user 22 to view the mapping data 194 and the lead representation 120' in any appropriate selected manner.

It will also be understood that the mapping catheter can be removed from the patient 26 prior to positioning the lead 120 in the patient 26. The procedure 180 can then proceed to placing and testing the RV lead in the patient 26 in block 206. Placing and testing the RV lead can proceed according to generally known methods such as for placing leads for pacing or defibrillation IMDs. In addition, configuring a RA lead in block 208 and placing and testing a RA lead in block 210 can also follow. It will be understood, however, that any appropriate procedure can be performed and a cardiac procedure is merely exemplary. In addition, any appropriate type of lead or number of leads can be positioned within the heart 80 of the patient 26 for a selected procedure.

At a selected point, such as after the leads are positioned and tested, an option image can be obtained by an external imaging device in block 211. The external imaging device can include the fluoroscope 28 or other appropriate external imaging system. The minimal or single image acquired by the imaging device can substantially reduce exposure to x-rays or the requirement of equipment usage.

The procedure 180 can then end or terminate in block 212. The ending of the procedure can include appropriate steps, such as programming an IMD positioned within the heart, as illustrated in FIG. 13 connecting implanted leads to the IMD, closing the incision, implanting the implantable medical device, or other appropriate steps. Programming the IMD can include wireless programmer, such as using the Medtronic 2090 or Carelink™ programmer, provided by Medtronic, Inc. of Minneapolis, Minn., USA.

Electrode Patch Positioning

With reference to FIGS. 1 and 2, the electrode patches 46a-50b that are prepared in block 184 and placed in a patient in block 188 can be any appropriate patches, such as the patches and controller of the Local Lisa™ previously sold by Medtronic Inc. of Minneapolis, Minn., USA. As an example, the LocaLisa® device can be used to generate the current in the patient 26. The PSU 40 can also be that disclosed in U.S. Pat. Nos. 5,697,377 or 5,983,126 to Wittkampf, incorporated herein by reference. It will be understood that any appropriate number of axes patches can be used, but the six disclosed herein can limit issues with sterile field maintenance and allow reasonable access to the patient 26 during a procedure. The patches can be positioned on the patient 26, such as orthogonally or generally nearly orthogonally to one another, to create three orthogonal or generally nearly orthogonal axes within the patient 26, and particularly intersecting within the heart 80 or other organ of interest of the patient 26. The patches 46-50 can be oriented based upon the organ or region of interest in the patient so that the original is at the region of interest. In addition, various instruments can be used, such as of different size or configuration, based upon the organ being explored or mapped.

The applied patches 46, 48, and 50, can each be used to conduct a substantially unique current waveform through the patient 26. For example, each pair of the patches can be used to conduct current at a different frequency. Alternatively, the currents could be time division multiplexed. Thus, the PSU 40 can be used to generate the unique currents in the patient 26. The currents generated in the patient 26 produce voltages that can be sensed with the electrodes, 108, 110 of the mapping catheter 100 or the lead 120, to be used to determine the electrode's relative position in the patient 26.

The reference electrodes 52 positioned on the patient 26 can be used to as a reference electrode for the electrodes being used to sense a voltage in the patient 26. The reference electrode 52a that is positioned over the xiphoid process can remain substantially fixed relative to the patient 26 Reference electrodes positioned on the patient 26 provide a reference for determination of voltages by the electrodes 108, 110 of the mapping catheter 100 within the patient 26.

As discussed above, at least one of the reference electrodes, such as the first reference electrode 52a, can be positioned substantially on or over the xiphoid process of the patient 26. Positioning the reference patch 52a substantially near the xiphoid process of the patient 26 can allow for a substantially fixed location of the reference patch 52a relative to the patient 26 regardless of respiration movement, cardiac movement, or the like of the patient 26. Also, as discussed above, positioning the second reference electrode 52b substantially directly across from the first reference electrode 52a (such as on a horizontal plane, as discussed above) can provide a second reference that can be used to reference the mapping data 194 generated or produced relative to the patient 26. Also, by positioning the second reference patch 52b at this location relative to the first reference patch 52a, respiration can be monitored by measuring the relative voltage or impedance difference between the two reference patches 52a, 52b using the PSU 40.

The various patches can be affixed to the patient 26 in any appropriate manner, such as via generally known semi-permanent or permanent adhesives. The patches 46-50 are also generally electrically coupled to the skin of the patient 26 to allow current to be conducted within the patient 26. For example, the patches 46-50 can be directly attached to a skin surface of the patient 26. The patches 46-50, however, can be removed once mapping or other procedures are completed.

Enabling plotting in block 192 allows for generation of the multiple data points for generation of the mapping data 194 of the patient 26 and mapping of selected regions of the patient 26, such as the heart 80. The mapping of the heart 80 of the patient 26 can be achieved by moving the mapping catheter 100 through selected portions of the heart 80 of the patient 26. It will be understood, as discussed above, that any appropriate region of the patient 26 can be mapped. Moving the mapping catheter 100 through the heart 80 of the patient 26 allows for generation of the mapping data 194 based upon a plurality of sensed voltages and calculated impedances at multiple locations within the heart 80 by the electrodes 108, 110 of the mapping catheter 100. As the mapping catheter 100 moves through the heart 80 of the patient 26, as exemplary illustrated in FIG. 5, data points can be acquired at a set interval of time or when selected by the user 22. The user 22 can use the foot pedal 64 to determine when a data point is to be acquired or for selecting where a landmark should be illustrated and identified. Nevertheless, the movement of the mapping catheter 100 through the heart 80 allows for collection of data points based upon sensing a voltage and/or calculating an impedance at multiple locations in the heart 80.

Managed Points

For example, as illustrated in FIG. 5, as the mapping catheter 100 moves through the heart 80, it can be positioned at different locations within the heart 80. For example, as it enters the right atrium chamber of the heart it can be positioned in a first selected location, as illustrated by the phantom mapping catheter 100'. A data point can be determined for the mapping catheter when it is at position 100'. The mapping catheter can further be moved through the heart 80 such as to a second or third location, as illustrated at 100 or 100", and data points can be further acquired at these additional locations. Although three points are specifically mentioned here, it will be understood, that any appropriate number of data points may be collected to form the mapping data 194, as illustrated in FIG. 6. These data points can be illustrated on the display device 58 as the data points 198. As also illustrated in FIG. 6, a plurality of data points 198 can be generated or acquired as the mapping catheter 100 is moved relative to the patient 26. It will also be understood that any appropriate number of data points 198 can be displayed on the display device 58.

The data points 198 can be represented individually or as a group. For example, a selected sphere, circle, or other appropriate geometric shape can be used to represent one or more acquired data points 198 of a position of the mapping catheter 100, or its respective electrodes 108, 110, within the patient 26. A single sphere data icon (or managed point) illustrated on the display device 58 can be displayed when two, three, or more data points have been collected for a respective voxel of the mapping data 194. Therefore, a single data point representation 198 on the display device 58 can be representative of one or more position data points acquired with the mapping catheter 100. Accordingly, the image display 58 can be densely or sparsely populated with representations of the position data points of the mapping catheter 100. The representation can be based upon a selection of the user 22 or other appropriate selections.

In addition, the mapping catheter 100 can move through the heart 80 according to various forces. For example, the sheath 104 of the mapping catheter 100 can be a substantially deflectable or guidable sheath. Additionally, the mapping catheter 100 can be guidable according to generally known techniques or processes. Therefore, the mapping catheter 100 can be moved through the patient 26 by direction of the user 22. In addition, forces within the patient 26, such as the flow of blood, can be used to move the mapping catheter 100 through the heart 80.

The balloon portion 102 can generate drag within the patient 26 due to blood flow or other fluid flows within the patient 26. Therefore, as illustrated in FIG. 5, the mapping catheter 100 can enter the heart 80 at a selected location and be moved through the heart 80 via drag formed on the balloon portion 102 to assist in moving the balloon portion 102, and the associated electrodes 108, 110, through the heart 80 such as to or through the pulmonary artery. Therefore, the mapping catheter 100 can move relative to the patient 26 in any appropriate manner, including a drag generated on the balloon portion 102.

Landmarks

Figure 8:
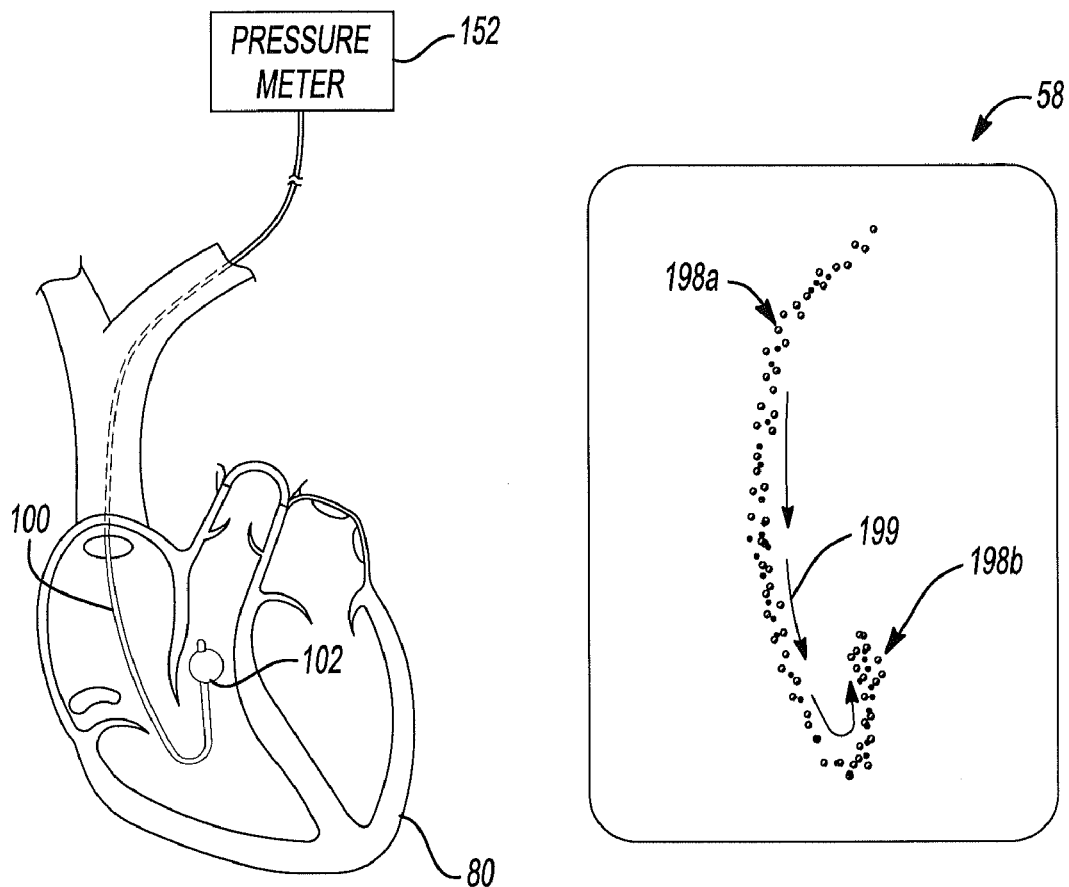
FIG. 8 is a detailed environmental view of a mapping catheter and a display device displaying related mapping information.

With continuing reference to FIGS. 2, 5, and 7 and further reference to FIG. 8, the catheter 100 can be moved through the heart 80. As the catheter 100 is moved through the heart 80, the position sensing unit system 40 can determine or calculate positions of the electrodes 108, 110 of the mapping catheter 100. Each of these determined locations can be displayed on the display device 58, as illustrated in FIG. 8, as various data points including 198a and 198b. Each of the data points collected regarding a position of the mapping catheter 100 can also include a time stamp or cycle stamp. Therefore, for example, a first data point 198a and a second data point 198b can include different time stamps. The time stamps can indicate which was acquired first as the mapping catheter 100 moved relative to the heart 80. As discussed above, drag on the balloon portion 102 can cause movement of the catheter 100 through the heart 80.

Accordingly, a movement direction can be determined and illustrated based upon the calculated or determined locations over time of the mapping catheter 100. An arrow 199 can also be illustrated on the display device 58 to represent the movement direction. The arrow 199 can provide an indication to a user 22 of the movement direction in the heart 80 and can assist in determining landmarks.

In addition, as the mapping catheter 100 is moved through the heart 80, as illustrated in FIG. 8, pulsative pressure exerted on the balloon portion 102 can be measured with the pressure meter 152 to determine a pressure pulse exerted on the balloon portion 102. The pressure pulse can be illustrated as a wave form that can be used to assist in identifying various locations in the heart 80, or other locations in the patient 26. The measured waveform may be low fidelity due to compressible gases and also due to the use of a small lumen in the lumen 106 of the catheter 100, but may be of enough fidelity to identify anatomical landmarks or portions. As the data points are collected regarding the location of the mapping catheter 100, in particular the electrodes 108, 110, a pressure pulse related to these positions can also be determined. The workstation 38 can save or associate each of the pressure pulses with the data points regarding the location of the mapping catheter 100 when the pressure pulse was measured. Accordingly, each of the data points 198 of the mapping data 194 can include information collected with the mapping catheter 100. In addition, the mapping catheter 100 can be used for electrogram recording and display. For example, equal atrial and ventricular contributions to the endocardial electrogram could help confirm a location proximal to the tricuspid or pulmonic valves. Therefore, each of the data points 198 of the mapping data 194 can have information associated therewith other than a position of the catheter 100.

The additional information can be used in conjunction with the position information to assist in identifying various regions of the heart 80, such as landmarks. For example, different portions of the heart, such as valves, chambers and the like can be identified using the electrograms, pressure information, and the like. This information, which is associated with the data points 198, can be used to identify landmarks in the mapping data 194 of the heart 80. Accordingly, as illustrated in FIG. 6, the landmarks can be illustrated on the display device 58 to assist a physician in identifying or recalling selected regions of the heart 80 determined with the mapping catheter 100. The landmarks 204, 206 can be identified using the physician's knowledge, information collected from the mapping catheter 100, and information collected from other instruments such as an electrocardiogram (ECG).

The landmarks can be labeled on the display device 58 in an appropriate manner. Landmarks displayed and labeled on the display device 58 can include a label line 220 that interconnects the landmark 204 with a text box 222. The length of the lead line 220 and the position of the text box 222 can be calculated to ensure that the position of the text box 222 does not obscure or obscures as few as possible the data points 198 displayed on the display device 58. In addition, the labeling of the landmarks 204, 206 or the identification landmarks that should be labeled or identified can also be done with the foot pedal 64 and/or the joystick 62. For example, depressing the foot pedal 64 can be used to show a menu of possible landmarks and the joystick can be used to highlight the landmarks and the foot pedal 64 can select a landmark label. The workstation 38 can then illustrate the landmark on the display device 58 and further provide the text box label 222 and the lead line 220 in an appropriate manner.

Returning reference to FIGS. 6 and 7, identification of landmarks in block 202 can be illustrated on the display device 58 as briefly discussed above. Selected landmarks, such as the cannulum of valves, ostia of veins or vessels, can be illustrated using the toroid 204. The toroid landmark 204 includes a radius centered on an axis 204'. The axis 204' and a radius of the toroid 204 can be based upon the data points 198 acquired near the toroid 204 or the location of the landmark which the toroid 204 identifies. For example, a selected portion of the data points 198 near the toroid 204, such as one or two or any appropriate millimeters on either side of the toroid 204 can be used to determine the direction of the central axis 204' for display on the display device 58. In addition, the data points 198 within the toroid 204 can be used to determine the radius of the toroid 204 for display on the display device 58. Therefore, the landmark toroid 204 can, in addition to identifying a selected landmark, also provide additional information to the user 22 regarding the size of the particular area, such as an area of a valve or vessel, and a relative orientation of the valve or vessel to the other acquired data.

The data points 198 of the mapping data 194 can also include the time stamps, such as discussed above. The time stamps can further be used to identify those data points acquired in a recent period, such as the data points 198', which can be illustrated as darker or a different color than older acquired data points 198". The illustration of a decay or timing of the illustration of the data points can be used by the user 22 to identify a most current location of the mapping catheter 100, the lead 120, or any other appropriate reason.

Surface Display

As discussed in the process 180 in FIG. 7, rendering of a surface can occur in block 200. Rendering the surface can proceed based upon techniques, as exemplary described herein, to render a surface relative to or with the data points 198 of the acquired data 194. Rendering the surface can occur using at least two surface rendering techniques.

Figure 9:
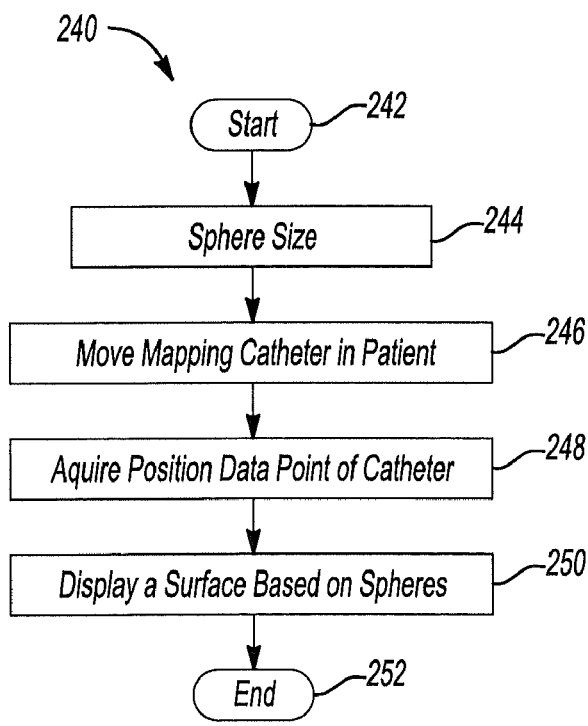
FIG. 9 is a flow chart illustrating a method of rendering a surface based on mapping information, according to various embodiments.

A first surface rendering technique for block 200 can include a "swept surfaces". The swept surfaces rendering technique can include a swept surface process 240 illustrated in FIG. 9 that can render the swept surfaces image data 241 illustrated in FIG. 10. The swept surfaces process 240 can begin in a start block 242. As discussed in relation to FIG. 7, the mapping catheter 100 can be prepared and introduced in the patient 26 as a part of the start block 242.

The swept surfaces process 240 can include selecting a sphere size in block 244. The sphere size selected in block 244 can be any appropriate size, such as a relative diameter of the electrode, such as the electrode 108 or 110. According to the swept surfaces process 240, the size of the electrode can be determined or estimated to be a sphere. Therefore, the sphere size in block 244 can substantially be the physical size of the electrodes 108, 110 of the mapping catheter 100. For example, the sphere or radius size can be about 1 mm to about 50 mm, including about 1 mm to about 15 mm, or about 1 or 5 mm to about 15 mm.

Once a sphere size is determined in block 244, the mapping catheter 100 can be moved in the patient in block 246. As the mapping catheter is moved in the patient in block 246, the data points 198 regarding the position of the catheter 100 can be acquired in block 248 and illustrated as the data points 198, illustrated in FIG. 10. As each position data point 198 is acquired, a sphere based on the sphere size input in block 244 can be determined. The plurality of spheres can be used to form the swept surface rendering 241 in block 250. The display of the surfaces of a plurality of spheres generates or renders three dimensional data regarding each of the position data points acquired regarding the position of the mapping catheter in block 248. The rendering, however, can be limited by the size of the sphere selected in block 244, but can be performed in substantially real time.

Because three dimensional data is displayed on the display device 58, an appropriate three dimensional surface can be displayed using the three dimensional data displayed in block 250. Moreover, the surface can be illustrated in real time allowing a real time acquisition and growth of the 3D surface. Accordingly, a three dimensional swept surface 241 representing a passage of the mapping catheter 100 can be displayed on a display device 58 rather than simple individual points 198.

The swept surfaces process 240 can then end in block 252. The rendered surface in block 200 using the swept surfaces process 240 in FIG. 9 can create a substantially real time surface model using the mapping catheter 100. In addition, as illustrated in FIG. 10, the display device 58 can display both of the individual points 198 of the mapping data and the swept surfaces rendering 241 of the mapping data for viewing by the user 22.

Figure 11A:
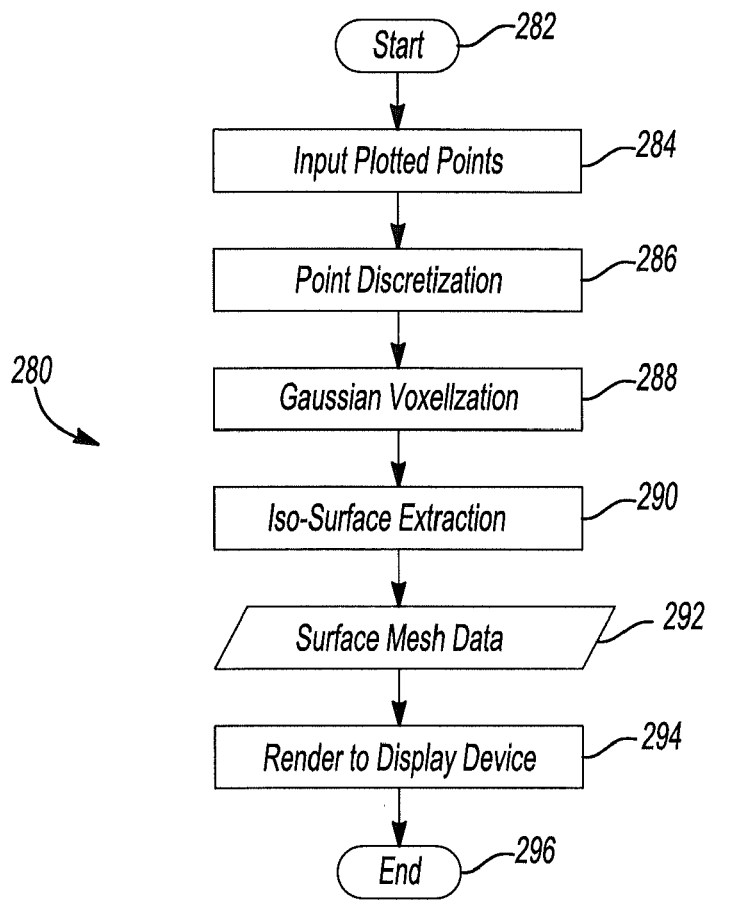
FIG. 11A is a flow chart illustrating a method of rendering a surface based on mapping information, according to various embodiments.

Again, returning reference to FIG. 7, and additional reference to FIG. 11, rendering the surfaces in block 200 of the procedure 180 can also or alternatively occur with a second process including isometric or other appropriate surface extraction procedure 280. Using the data points 198 acquired and displayed on the display device 58 a surface rendering 281, illustrated in FIG. 12, can be produced with the surface extraction procedure 280.

The surface extraction procedure 280 can begin in start block 282, which can include preparing and positioning the mapping catheter 100 within the patient 26. The data points for rendering according to the surface extraction procedure 280 can be acquired as discussed above, plotted relative to the patient 26, and saved in a memory that can be accessed by the workstation 38 or any appropriate processor. Accordingly, the plotted points can be inputted into the surface extraction procedure 280 at block 284. Once selected plotted points have been inputted, the surface extraction process 280 can proceed to point discretization in block 286. Point discretization can include appropriate hierarchies or organizational methods, including known cube grid or octree arrangements.

If a cube grid organization method is chosen, each of the points from the plotted points in block 284 can be assigned to a cube of a selected size in a grid pattern. Each of the cubes could be assigned the data points that fall within the perimeter of the cube of the grid when the position data points 198 are overlaid or aligned with the cube grid. The cube grid could then be queried to identify those points that exist within a selected cube. In this way, the position point data 198 can be identified and further processed or rendered, as discussed further herein.

According to various embodiments, an octree procedure can also be used. The octree structure is a data organization structure that includes a hierarchal or trunk structure with nodes or leaf nodes where data points exist. Accordingly, a leaf node does not exist on the hierarchical structure unless a data point exists at the particular location. Accordingly, position data points 198 would exist on the trunk structure where they were determined. Thus, there is no memory wasted for empty cubes, as may exist if no data happen to be acquired for a particular cube or grid location.

According to various embodiments, point discretization in block 286 allows for an indexing or layout of the data for access and further processing steps in the surface extraction process 280. Accordingly, the point discretization can include appropriate discretization or indexing processes including those discussed above. Point discretization is used to determine an appropriate location of the data acquired and for querying in further processing, discussed below.

After point discretization in block 286, a Gaussian Voxelization can occur in block 288. The Gaussian Voxelization in block 288 is used to voxelize the data into 3D data along a selected grid, such as in x, y and z directions. The voxelization of the data can include the formation of a three dimensional voxel data set along the grid pattern.

The voxelization can proceed by visiting each cube or voxel in the grid and identifying the distance of a data point that is a selected distance from a center of the voxel by querying the point discretization data. This can include finding all data points that are within a selected radius from a center of each of the voxels. If a data point is found for a particular voxel, a scalar value is computed based upon the point's distance from the center of the voxel. A Gaussian function can be used to determine the discretization value given to the point where the value decreases in the known Gaussian manner as the point deviates or is further from the center of the voxel. Accordingly, a data point closer to the center of the voxel is given a higher value than a point that is further from the center of the voxel. Each of the points within a voxel could have different values. The value a point receives is determined by its distance from the voxel's center. So a point at the dead-center of a voxel will have a different value than a another point, which is still in the same voxel, but deviates slightly. The value is determined by the Gaussian function discussed above. A voxel with no data points can be assigned a zero. A voxel may, according to various embodiments, be given a single value even if it contains multiple points, such as the value of the highest valued point in the voxel.

Once the data has been voxelized in block 288, an Isometric (Iso) surface extraction can occur in block 290. The Gaussian Voxelization in block 288 creates a substantially three dimensional volume set from which a surface can be extracted in block 290. Appropriate surface extraction algorithms can be used to extract the surface based upon the Gaussian Voxelization in block 288. For example, a marching cubes algorithm can be used to extract a surface based upon the Gaussian Voxelization data in block 288. The marching cubes algorithm can be implemented from various sources such as the visualization tool kit at http://public.kitware.com/vtk, incorporated herein by reference. Various other techniques are also described in U.S. Pat. No. 4,710,876 to Cline and Lorensen, incorporated herein by reference. Other appropriate extraction techniques can also include marching tetrahedrons. Regardless, the surface extraction algorithm can use the voxelized data in block 288 to determine a surface.

Once the surface extraction is completed in block 290, the extracted data can be saved as a geometric mesh in block 292. The geometric data can include triangle data relating to the marching squares extraction that occurs in block 290. The saved geometric mesh data in block 292 can then be rendered on the display device 58 in block 294. An appropriate rendering system can be used, such as the OpenGL® rendering software or system (Silicon Graphics, Inc., having a place of business in Mountain View, Va., USA) that defines an interface to hardware, such as the hardware of the PSU 40. The rendering of the data to the display device 58 in block 294 can display the extracted three dimensional surface 281 of the data acquired with the mapping catheter 100.

Figure 12:
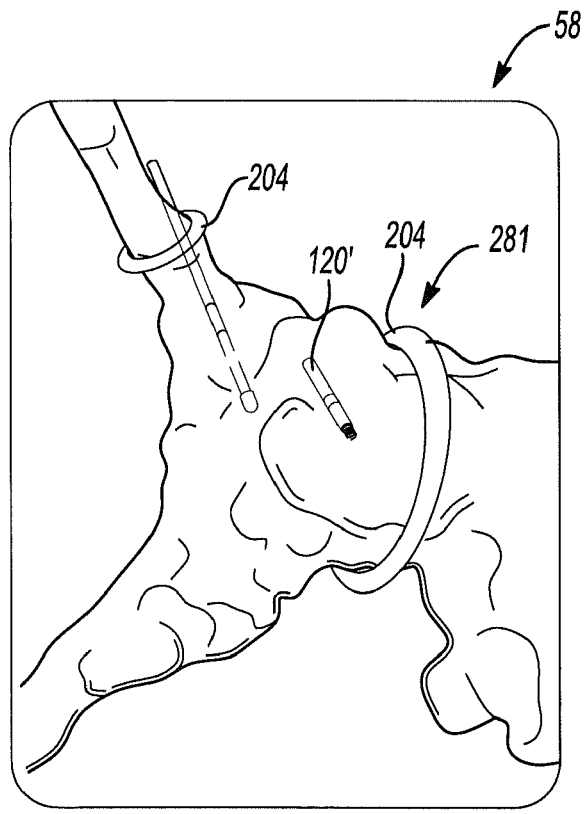
FIG. 12 is a display device illustrating surface rendered data.

The extracted three dimensional surface 281 that can be viewed by the user 22 to assist in identifying locations within the anatomy, such as within the heart 80, or for understanding the anatomy of the heart 80 or positions of the mapping catheter 100 or lead 120 within the heart 80. It will be understood, that landmark icons 204 can also be displayed relative to the extracted three dimensional surface 281, as illustrated in FIG. 12. In other words, landmarks that are identified in the position data points 198 can be super-imposed on the extracted three dimensional surface 281 as well. It will be further understood, that landmarks can be illustrated on any appropriate data, such as the swept surfaces data 241 as well. The surface extraction process 280 can then end in block 296.

Accordingly, the surface extraction process 280 can be used to render or display a surface of the data points 198 acquired with the mapping catheter 100.

The data points 198 acquired with the mapping catheter 100 can also be displayed unrendered or unfiltered on the display device 58. That is, as illustrated in FIG. 7, the mapping data can be displayed on the display device 58 as the multiple points determined with the mapping catheter as a part of the position sensing unit system 40. Thus, a plurality of data points can be displayed on the display device for viewing by the user 22.

In addition, the mapping data 194 displayed on the display device 58 can be displayed with or without any selected filtering. For example, the data points being displayed on the display device 58 can be displayed in substantially real time as they are acquired and calculated. That is, as the voltage is sensed and the impedance calculated, the determined location of the mapping catheter 100 or the lead 120 can be displayed on the display device 58.

The position sensing unit 40 can also filter the data displayed on the screen 58. The data displayed on the screen 58 can be a smoothed or average location. For example, a point displayed on the screen can include an average location of the data points acquired and determined for the mapping catheter 100 or the lead 120 for a set period of time. For example, an average location of the mapping catheter 100 or the lead 120 for five seconds can be displayed on the display device 58. It will be understood, however, that a selected amount of filtering may or may not be used to display the data points on the display device 58. It may be selected, such as when positioning the lead electrode 126 into the heart 80, a substantially unfiltered view be given to the user 22 to allow for a substantially precise illustration of a position of the lead electrode 126 relative to the data points or surface displayed on the display device 58. This can assist in a substantially precise location and implantation of the lead electrode 126 during a selected procedure.

Multiple Electrode Tracking

As illustrated in FIG. 12, and discussed above, data acquired with the mapping catheter 100 can be illustrated on the display 58 and a surface can be rendered relative to the data. In addition, various other instruments, such as the lead 120, can be tracked or its position determined with the PSU 40 and its position can also be illustrated on the display 58 relative to the map data. In various embodiments, multiple electrodes can be positioned along the length of an instrument. For example, multiple electrodes can be positioned along the lead body 120, as illustrated in FIGS. 12Ai-12Ci.

One or a plurality of electrodes can be positioned along a body of the lead 120. The lead 120 can include the implantable electrode 126 and a body of the lead 120b can include a catheter or other portion through which the lead 120 is positioned. As illustrated in FIG. 12Ai, a tracking electrode 121 can be positioned relative to the implantable electrode 120a either directly on the body of the lead 120 or on a catheter through which lead 120 is positioned. The tracking electrode 121 can be interconnected with the PSUI/O 42 via a connection, such as a wire 121a. As discussed above, the PSU 40 can be used to identify a relative location of an electrode, such as the implantable electrode 126 and the tracking electrode 121.

The tracking electrode 121, can include a ring or a band of metal, such as a solid band of metal, that can be positioned on an insulator portion or positioned directly on the lead body 120b or catheter through which the lead 120 is positioned. The tracking electrode 121 can then be used to measure a voltage or impedance at its position on the lead 120.

If the lead 120 is positioned, such as extending through or out of a catheter, the tracking electrode 121 can be used to track a position of a lead 120 other than the distal tip of the lead based only on the position of the implantable electrode 126.

The tracking electrode 121 can be fixed relative to the implantable electrode 126 along the length of the lead 120 that can be selectively removed after implanting the implantable electrode 126. The tracking electrode 121, according to various embodiments, can be fixed to the lead wall, formed integrally or as one member with the lead wall, or removable therefrom. For example, a frangible piece could be broken by pulling on the connection wire 121a to remove the tracking electrode 121. Alternatively, the tracking electrode 121 can be provided to be implanted with the lead 120 and not be removed.

Regardless of the connection of the tracking electrode 121 to the lead 120, the display 58 can be used to display the relative position of the various electrodes of the lead 120. The surface data 281 can be illustrated on the display 58. A first icon element 126' can be illustrated relative to the surface data 281. For example, the icon 126' can be used to illustrate the implanted position of the implantable electrode 126. A second icon element 120i' can be used to illustrate a position of the tracking electrode 121 positioned on the lead 120. Accordingly, the user 22, such as a surgeon can determine or be informed of a position of a selected portion of the lead 120 relative to the implanted electrode 126.

For example, the user 22 may use the tracking electrode 121 which is positioned at a known location on the lead 120 to determine the amount of lead slack within the patient 26. If the tracking electrode 121 is positioned five centimeters from the implantable electrode 126, but the icons 126' and 121' on the display 58 are near each other, such as within one centimeter of each other, the user 22 can estimate the amount of lead positioned within the patient 26, such as within the heart 80.

FIG. 12Bi illustrates that the tracking electrode 121 can include a plurality of tracking electrodes 121i, 121ii, 121iii and 121iv. Each of the tracking electrodes 121i-121iv can be interconnected with a wire 121a to the PSU I/O 42. Each of the tracking electrodes 121i-121iv can be constructed substantially similarly to the tracking electrode 121 illustrated in FIG. 12Ai. Accordingly, multiple positions of the lead body 120b can be determined by tracking the multiple tracking electrodes 121i-121iv. The greater the number of tracking electrodes 121 the greater the resolution of the determined or illustrated geometry. Accordingly, the number and spacing of the tracking electrodes 121 can be selected for illustration and tracking resolution.

As illustrated in FIG. 12Bii, the icon element illustrating the implantable lead 126' and the position elements or position lead/electrodes 121i'-121iv' are illustrated. Therefore, the user 22 can determine or have knowledge of a plurality of positions of the electrode body 120b relative to the implantable electrode 126. Again, the various positions of the electrodes can be illustrated relative to the surface data 281 or the map data 198 on the display 58. The user 22 can have knowledge of a plurality of points of the electrode body 120b to determine a contour, length of lead within the patient 26, or other appropriate information.

The position element or electrode 121, illustrated in FIGS. 12Ai and 12Bi can be provided as a single position electrode element 123, according to various embodiments, as illustrated in FIG. 12Ci. The single position electrode element 123 can include a plurality of tracking electrodes 123i-123iv. It will be understood that any appropriate number of individual tracking electrodes can be provided on the single electrode element 123 but six are exemplary illustrated. The tracking electrode assembly 123 or the single position electrode portions can be connected to the PSU I/O 42 with the wire 121a. Each of the individual electrode portions 123i-123iv can be positioned on a single flexible or rigid portion sleeve 123a. The sleeve portion 123a can be flexible and formed of an insulator material or of any appropriate material to be positioned on the lead 120. Also, the several electrode portions 123i-123vi can be formed with the lead 120.

The position of the individual position electrode portions 123i-123iv can be illustrated on the display 58, as discussed above. Multiple icon elements 123i'-123iv' can be illustrated relative to the surface data 281 or the map point data 198 to illustrate their position relative to the surface data 281 the map points 198. The position of the plurality of the tracking electrode portions 123i-123iv can be used and illustrated on the display 58 to provide information to the user 22 regarding a plurality of positions of the lead body 120b. Again, the contour of the lead body 120b can be used to determine the amount of lead slack or the amount of lead positioned within the patient 26 or a position of various specific portions of the lead body 120b.

Guidewire Tracking

In addition to tracking multiple locations on a lead or instrument, a guide wire 125 can also be tracked. As illustrated in FIG. 13A, a guide wire 125 can be positioned within the patient 26, such as relative to the heart 80, a vein of the patient 26, or any appropriate portion. The guide wire 125 can include a metal portion, or be substantially all metal and be guidable within the patient 80. The guidewire can be any appropriate guide wire, such as Silverspeed™ guidewire. Generally, the guide wire 125 can include a distal end that is blunt, bent, or very flexible to resist or reduce possibly perforating the heart 80. The guide wire 125 can be used to assist in positioning the lead 120, including the lead electrode 126, relative to the heart 80 of the patient. As is understood, the guide wire 125 can be used to guide a later positioned lead into the patient 26. The position of the guide wire 125, as discussed herein, can be illustrated for use by the user 22 to assist in selecting an implantation site or confirming appropriate direction of movement of the guide wire 125. For example, even when no map is illustrated, the PSU 40 can be used to determine that the guide wire is moving generally inferiorly, superiorly, laterally, or medially in the patient 26.

The position of the guidewire 125, as discussed herein, can be determined from an insertion point. The insertion point can be a point when the guidewire 125 first ends the conductive medium of the patient 26, such as blood. The insertion point can be when the guidewire 125 first enters the patient 26, such as insertion point 310 into a vein of the patient 26 or when the guidewire 125 exits another insulating portion, such as a catheter or lead sheath. The catheter or sheath can include an electrode 129 that can be a position element. The lead can also include a lead electrode 126.

Generally, the guide wire 125 and the lead electrode 126 or the electrode 129 of the catheter or sheath can be electrically insulated from one another so that each can separately and independently be used to sense a voltage within the patient 26. The guide wire 125 can be used to measure a voltage or determine a bioimpedance. The guide wire 125, therefore, can be connected with the PSU I/O 42. With the PSU 40 a current, as discussed above, can be generated within the patient 26 and a voltage can be measured with an exposed and conductive portion of the guide wire 125. The guide wire 125 can also be determined to be exposed to a conductive portion of the patient 26 by measuring an impedance in a circuit including the guidewire 125. It will be understood that the guide wire 125 can be positioned substantially independently within the patient 26 of the lead 120 or any other portion, such as a catheter. For example, the guide wire 125 can be moved to a selected location within the patient 26, such as to position the guide wire 125 in contact a particular apex (e.g. the right ventricular apex), and a dilator and catheter can then be passed over the guide wire 125. The catheter can be moved using the guide wire 125 to guide the catheter to the selected location.

Once the guide wire 125 is positioned within the patient 26, and it is connected to the PSU I/O 42 of the PSU 40, a voltage can be sensed and/or a bioimpedance can be determined at the guide wire 125. The position of the guide wire 125 can be determined from with the PSU 40, as discussed above including sensed voltages or determined impedances. Also, the position of the guidewire can be illustrated as a single point or a path or surface can be illustrated to show the past path and positions of the guide wire 125.

The measurement of the voltage or determined bioimpedance of the guide wire 125 is a single value, since the guide wire 125 is a conductor, the voltage along it can be understood to be single value. The exposed length of the guide wire 125 will produce a voltage value that effectively sums the average values that would be measured at the plurality of locations which it occupies. This is because the guide wire 125 can include a substantial length that is exposed, rather than a relatively small portion or member such as the lead electrode 126. As shown in FIG. 13B, the position of the guide wire can be illustrated as an icon 125' relative to the surface 281 or the map points 198 on the display 58. If the lead 120a is also positioned relative to the guide wire, the lead electrode 126 (shown in phantom) can be illustrated as an icon 126' (shown in phantom) on the display 58. Alternatively, or in addition to a lead electrode 126, the catheter with the tip electrode 129 can be used and an icon 129' can illustrate the location of the tip electrode 129. The position of the tip electrode 129 can be determined with the PSU 40.

The position of the guide wire 125 can be determined according to a method illustrated in a flowchart 300, shown in FIG. 13C. As illustrated in the flowchart 300, the guide wire position determination procedure or algorithm can begin at start block 302. The guide wire 125 can be positioned in the patient 26 in block 304 and an initial position or insertion determination in block 306 can be made when the guide wire 125 is first inserted into the patient 26 or exposed to a conductive medium (e.g. when exiting a catheter). The insertion position can be based on selected information. For example, the insertion position can be based on an initial measurement or determination taken when only a selected length of the guide wire 125 is positioned in the patient in block 306a. For example, it can be selected to position the guide wire 125 a length into the patient 26 such that a measured bioimpedance is substantially equivalent to a point or single location. Alternatively, the insertion location of the guidewire can be a distal end of the catheter 120 which has an electrode 129 or position element at the distal end. The measurement with the electrode at the distal end can be used as the insertion point determination in block 306b and illustrated as icon 129' on the display 58. Also, the guide wire may extend from any appropriate portion such as the lead and may extend past the lead electrode 126. The lead electrode, if insulated from the guidewire 125, can used similar to an electrode on a distal end of the catheter 120. Also, the insertion position can be manually input in block 306c.

Based on the insertion position in block 306, as illustrated in FIG. 13B, the surface 281 can be generated to illustrate a surface of a selected portion of the patient 26. It will be understood, however, that the position of the guide wire 125 need not be illustrated relative to the surface 281 or the map points 198 but can be illustrated as a relative location on the display 58. Regardless, the insertion point of the guide wire 125 can be an insertion point 310 illustrated in FIG. 13A. This insertion point 310 can be any appropriate point in the patient 26 for positioning the guide wire 125 within the patient for performing a procedure. The insertion point can also be a point where the guide wire 125 first extends from an insulated sheath, such as the catheter 120 or past the lead electrode 126. Regardless, the insertion point determined in block 308 can be used to illustrate the position of the guide wire 125 within the patient when a selected or substantial length of the guide wire is exposed within the patient 26.

The guide wire can then be advanced in block 312. A measurement of the bioimpedance on the guide wire can be made at any selected point or substantially continuously in block 314. The measured bioimpedance along the guide wire in block 314 can be measured in any appropriate matter, similar to the manner of measuring the bioimpedance of any appropriate electrode as discussed above. For the guide wire 125, however, the determined bioimpedance can be understood to be an average or cumulative measurement along the length of the exposed wire in block 316. In other words, the voltage sensed or the impedance determined is a single value, but is based on the entire length of the guide wire 125 that is exposed. Thus, the single value of the guide wire 125 is determined to be at a midpoint of the exposed portion of the guide wire 125. As discussed above, the determined bioimpedance at any electrode can be used to illustrate a relative position of the electrode on the display 58. Accordingly, the measured impedance at the guide wire in block 314 can be used to determine a single position in block 318.

The reported position of a guide wire 125 is simply a point that is related to the single value (average) of the measured impedance and is generally the midpoint of the guide wire 125. The position of the distal end of the guide wire 125, however, can be determined in block 320 and is based on the known insertion point form block 308. The position of the distal portion of the guide wire 125 can be determined, and represented on the display device 58, as a point that extends from the insertion point (e.g. where it exits the lead or catheter) to twice the length from the insertion point, determined in block 308, and the determined position in block 318. Accordingly, a projection of the length of the guide wire 125 that is twice the distance from the insertion point determined in block 308 and the determined position of the guide wire 125 based on the determined bioimpedance in block 318 can be performed in block 320.

The position of the guide wire 125 can be illustrated on the display 58, as illustrated in FIG. 13B, as a single point 125' that is representative of a position of the distal end of the guide wire 125. Alternatively, or in addition thereto, the guide wire 125 can be illustrated as an icon 125a' that extends from the insertion position to the point that is twice the length of the distance from the insertion position to the determined position in block 318. Also, multiple points can be displayed to show a surface or a trail of points showing a determined path of the guide wire 125. It will be understood, however, that the represented position of the distal end of the guide wire 125 may have a certain error if the guide wire 125 physically bends within the patient 26.

Once the length of the guide wire is projected or the position of the distal tip is determined, it can be projected or displayed on the display 58. It will be understood that the displayed position of the guide wire 125 can be updated substantially continuously or sequentially as selected by the user 26. After the projection of the guide wire 125 in block 320, a decision of whether the guide wire will be further advanced can be made in block 322.

If it is determined that the guide wire 125 should be further advanced, then the YES routine 324 can be followed to advance guide wire 125, further in block 312. If it is determined that the guide wire 125 is at a selected or appropriate location, such as for guiding the lead 120 to a selection location within the patient 26, the NO routine 326 can be followed to an end block 328. It will be understood that the end block 328 can simply illustrate an end for determining a position of the guide wire 125 and not an end of a complete surgical procedure. For example, as discussed above, the guide wire 125 can be used to guide the lead 120 to a selected position within the patient 26. Accordingly, once it is determined that the No routine 326 should be followed to end the guide wire advancement procedure that the lead 120 can be advanced over the guide wire 125 to its selected location.

Clarifying a Three Dimensional Nature of Data

The display 58 can be a two dimensional display that is displaying the map data in a three-dimensional manner. As illustrated in FIGS. 15A and 15B, however, the virtual view of the data can be changed to more clearly and/or distinctly represent the three-dimensional (3D nature) of the map data. Rocking or rotating a view of the map data can clarify or enhance an understanding of the 3D nature of the map data on the display 58.

As illustrated above, for example in FIGS. 6 and 12, an image of map data can be displayed on the display 58 that represents the anatomy of the patient 26. The display 58, however, can include a video monitor, such as a CRT or LCD display, that is substantially two dimensional. As further discussed above, the mapping data generated regarding the patient 26 can be substantially three dimensional. As illustrated in FIG. 2, three axis, x, y, and z, can be generated relative to the patient 26 through the use of the various electrode patches 46a-50b.

As illustrated in FIG. 6, the data, for example, the map points 198, can be displayed from various perspectives. An anterior-to-posterior and medial-to-lateral perspective or oblique perspective can be viewed on the display 58. The views on the display 58, however, can be substantially static. Although one skilled in the art will understand that the static images represent a single view of the patient 26, based on the data that is mapped of the patient 26, various three dimensional features that have been mapped may remain substantially hidden in a background because of the three dimensional nature of the data being displayed on a two dimensional surface of the display device 58. Accordingly, a rocking or vibrating method can be used to illustrate an image on the display device 58 that is substantially not static or at least a view of the image where the data is not static. A virtual camera can be provided to move relative to the plotted or displayed map data points 198 or the surface 281 to allow the user 22 to more clearly understand the three dimensional nature of the data.

As illustrated in FIG. 14, a method 370 illustrated in a flowchart can be used to illustrate a three dimensional nature of a data, such as the mapping data acquired of the patient 26, on a substantially two dimensional display. As further illustrated in FIGS. 15A-15B, a rotating virtual camera (VC) can be used to generate or display a changing two dimensional view of a three dimensional object, whether real or virtual. The image on the display 58 is from the viewpoint of the virtual camera VC. According to the method 370 in FIG. 14, the rocking procedure can begin in block 372. After starting the method 370, display of the mapped data, including either or both of the points or surfaces, can be done in block 374, as illustrated in FIG. 15A. Discussion herein to FIGS. 15A and 15B of a "T" is merely for clarity. The user 22 can then make a decision on whether to turn rocking ON or OFF in block 376. If the user turns OFF or does not start rocking, the OFF routine can be followed to the stop block in block 378. If the user turns ON the rocking, then the ON routine can be followed to select a focal point relative to the displayed map data in block 378.

When selecting a focal point F in block 378, illustrated in FIG. 15A, the focal point can be selected substantially automatically by an algorithm, manually by the user 22, or in a combination thereof. For example, the focal point can be selected by the algorithm as a substantially geometrical center of the mapped data displayed in block 374. Alternatively, the user 22 can identify an area or point within the displayed map data or at a position relative to the displayed map data for selection as the focal point. Accordingly, the focal point need not be within a boundary of the map data.

Once a focal point is selected in block 378, a circle or arc, as illustrated in FIG. 15A can be defined around a y-axis, generated or defined relative to the map data displayed in block 374, or a center at the focal point selected in block 378. A radius R, as illustrated in FIG. 15A, can also be defined based upon a current location of the camera or at any selected radius in block 380. It can be selected, for example if the rocking is not to interfere or be substantially seamless with viewing of the map data, that the radius of the circle defined in block 380 be equal to the distance defined from the focal point to the current view point of the virtual camera for viewing the map data. It will be understood, however, that the radius can be predefined by the user or automatically by the system and the virtual camera can be moved to that radius.

After the circle is defined, including the radius in block 380, the arc of the circle in which the camera is to travel can be defined in block 382. Again, it will be understood, that the arc for moving the camera in block 382 can be defined manually by the user 22, by a system, such as the PSU 40, or in a combination thereof. For example, the PSU 40 can include a preset arc of movement such as about 15 degrees. The user 22 can augment the arc of movement, however, either before or after viewing a set number of repetitions of rocking to an arc greater or less than a preset amount. Additionally, or alternately thereto, if the user selects to turn ON the rocking in block 376, an initial pop-up or configuration menu can be provided and the user can select various features, such as the radius in block 380, the arc in block 382, and various other features as discussed herein.

For example, the direction for movement of the VC along the arc can be set in block 384. Again, the direction for movement along the arc can be user selected, system selected, or a combination thereof. The direction for rocking can also be selected prior to illustrating any rocking, after a set number of repetitions of rocking, or at any appropriate time. Generally, however, the camera is able to rotate or move along the arc in a clockwise or counter clockwise direction which can be selected or started in block 384.

The VC can be moved for one time step or increment along the arc defined in block 382 defined in block 386, as illustrated in FIG. 15B. The VC will move in the direction set in block 384. The time step can include a distance of travel, such as a set number of degrees, per camera movement. For example, the system or user 22 can select to move the camera one degree, two degrees, three degrees, or any appropriate number of degrees. For example, if the arc is defined as 15 degrees in block 382, and the user 22 wishes to view five views of the data, then a time step can be defined as three degrees. Accordingly, the camera can be moved three degrees per time step and one time step can be traveled in block 386.

The map data can then be redisplayed in block 388 based upon the position of the camera in block 386. As discussed above, the map data, including the map data points 198 or the surface 281, is data or points generated by measuring a portion of the patient, such as the heart 80. Accordingly, if the data does not move, but a perspective of viewing the data moves, then the view of the data may be altered. For example, as illustrated in FIG. 6, anterior-to-posterior and oblique views can be provided to illustrate the data from a different perspectives to show various anatomical features. A further example is illustrated in FIGS. 15A-15B.

After the points are re-displayed in block 388, the user 22 can determine whether rocking should be stopped in block 390. As discussed above, the query for stopping rocking can occur at any time such as after a set number of repetitions of rocking, a set number of time steps, or at any appropriate time. Therefore, manual input from the user 22 may or may not be necessary to follow the YES routine to the stop block 378. Similarly, manual input from the user 22 may or may not be necessary to follow the NO routine to the decision block 392 of whether the camera has reached the end of the arc.

As discussed above, the length or extent of the arc can be identified or determined in block 382. If it is determined that the VC has not reached the end of the arc, then the no routine can be followed to move the VC one more time step in block 386. At that point, such as at a second time step from the initial position (i.e., i+2) of the VC, the data points can be redisplayed in block 388 and the user can again be queried as to whether the rocking should be stopped in block 390.

Returning reference to the decision block of whether the camera has reached the end of the arc in block 392, the YES routine can be followed to switch direction of travel in block 394. If switching the direction of travel is determined in block 394, the camera can move one time step along the arc in the current direction of travel in block 386, which can be the reverse of the initial direction selected in block 384. This can allow the rocking motion, as the VC can move along the arc in selected time steps and then seamlessly reverse direction. At each time step, the points can be redisplayed in block 388.

As illustrated in the flowchart 370, a rocking of the viewing of the map data can be performed substantially automatically after defining a focal point and moving a VC relative to the data. Returning reference to FIGS. 15A and 15B a three dimensional object 400 is illustrated in FIG. 15A. The three dimensional object 400 can be any appropriate object and is illustrated as a "T" for simplicity of the current discussion. A focal point F can be identified, as in block 378. The vertical or y-axis can also be identified relative to the data. A virtual camera (VC) can be determined or positioned at some radius (R) along the x-axis. An arc a can also be defined, as in block 380. As discussed above, a direction and the time step of the VC can then be identified in blocks 384 and 386 and the VC can move.

As illustrated in FIG. 15B, once the VC has moved a first time step, (i+1), the perspective of the virtual camera has changed relative to the three dimensional data 400 from the initial position "I" of the VC. A different perspective can show hidden data or data not viewable from the first perspective at position (i) on the arc α. For example, an open or hollow area 402 is clearly seen from the second perspective at the first time step (i+1) that can not be seen due to the surface data 404 at the first perspective at the first point (i).

The VC can continue to move along the arc as discussed in the flowchart 370. Once the VC reaches a final point (f), which can be two time steps (i.e., i+2), the virtual camera (VC) can switch directions, such as in block 394, or be stopped such as in the user 22 stopping the rocking in block 390. Regardless, the changed perspective relative to the data 400 can allow the user 22 to more clearly understand the data 400 in its three dimensional nature even though the display is a substantially two dimensional display, such as the display 58. The rocking can enhance the user's perception of the spatial relationships of the data displayed on the display device.

Implantable Device

As discussed above, the PSU 40 can be used to implant any appropriate system, for example an implantable medical device (IMD) 600 can be implanted, shown in FIG. 16. The IMD 600 and its associated lead or leads 120 can be implanted without the external imaging device 28. Although, it will be understood, that the imaging device 28, or appropriate imaging device, can be used during an implantation procedure, such as to confirm placement of the lead 120 once positioned with the PSU 40. It will also be understood, that the PSU 40 can be used to supplement placement of an implantable member, such as the lead 120, with the imaging device 28, to reduce the number of images acquired, or eliminate direct imaging of the patient 26 and instruments entirely.

The IMD 600 can include implantable pacemakers, implantable cardioverter defibrillator (ICD) devices, cardiac resynchronization therapy defibrillator devices, or combinations thereof, exemplarily illustrated. An exemplary dual chamber IMD can include the Concerto Model C154DWK, sold by Medtronic, Inc. of Minneapolis, Minn., USA, but appropriate single chamber IMDs can also be implanted. The IMD 600 can include an implantable case or body assembly 602. The implantable case 602 can be formed of appropriate materials and include appropriate features, such as a hermetically sealed body wall. The body wall can be made of a substantially inert material or of a conducting material.

The lead assembly 120 can be interconnected with the implantable case 602 at a selected time. As discussed above, the lead can be guided to an implant location, such as in a right ventricle, with the PSU 40. The lead 120 can then have its electrode 126 fixed to the heart 80. It will be understood, however, that any appropriate number of leads can be interconnected with the implantable case 602 and can include any appropriate number of electrodes.

The PSU 40 and the various methods discussed above can be used to implant the lead 120 and other portions, such as an implantable medical device. The implantable medical device can be programmed once it is implanted, as illustrated in FIG. 16. A programmer or programming system 610 can be provided to program the implantable medical device. The programmer 610 can include a telemetry system that is operable to wirelessly transmit a signal to the processor within the case body 602. It will be understood that a wired communication system can also be used. In addition, an induction system can be used where a coil is positioned near the case body 602 and a signal is sent from the programmer via induction. The programmer 610 can also receive information from the IMD 600 (e.g. time and duration of arrhythmias and programming settings) to assist in providing an appropriate program for pacing. The programmer 610 can include any appropriate programming system, including one generally known to those skilled in the art, such as the Medtronic 2090 or Carelink™ programmer, provided by Medtronic, Inc. of Minneapolis, Minn., USA.

Distortion Correction

The map data, or the illustration thereof, may be distorted because of various effects. Correction for the distortion, as discussed herein and illustrated in FIGS. 17-19B, can assist in displaying the map data points and determining a position for implanting leads or the IMD 600. As discussed above, map data can be generated and used to illustrate map data points 198 or a surface 281 on a display 58. The lead 120 can then be tracked or guided with the PSU 40 or any appropriate tracking system relative to the patient 26. To appropriately collect and illustrate the data on the display 58, however, various corrections can be made to the data or calibrations to the system 40 to ensure correct and plausible illustration of the data on the display 58. According to various embodiments, a calibration or correction can be performed to correct for distortions that may be realized or encountered within the patient 26 when using the PSU 40. As illustrated in FIG. 17, a flowchart 650 illustrates a method 650 for correction of various inherent or encountered distortions within the patient 26.

With continuing reference to FIG. 17, the method 650 illustrated in the flowchart can begin in start block 652. An instrument, such as the mapping catheter 100 including the tip 108 and ring 110, can then be positioned in the patient in block 654. It will be understood that the discussion of a tip and ring herein is merely a specific example of an instrument that can include two or more electrodes that are positioned a relatively fixed distance to one another. As an example, as illustrated above, the mapping catheter 100 can include the tip electrode 108 positioned on the distal end of the instrument and a ring electrode, such as the ring electrode 110 positioned proximally of the balloon 102 portion of the mapping catheter 100. Accordingly, the tip and ring discussed in the flowchart 650 can exemplary be the tip and ring electrode illustrated in the mapping electrode 100. It will be understood, however, that the tip and ring may simply be any two electrodes on an instrument. For example, the tip and ring can be a distal and proximal electrode that are positioned at a substantially fixed location relative to one another of any instrument. For example, a bipolar pacing lead can be positioned relative to the heart 80 for mapping or for implantation. Using the calibration or correction of the flowchart 650 can also be used to calibrate or correct the position of the two electrodes of a bipolar lead.

Once the instrument with a tip and ring electrodes are positioned in the patient in block 654, electrode impedance data can be collected for the tip and ring electrodes in block 656. As discussed above, the PSU 40 can include the electrode patches 46a-50b that can inject currents into the patient 26. The currents cause a voltage change or current to be formed between pairs of the electrodes and an impedance can be measured within the patient 26. Accordingly, as discussed above, impedances can be measured with the electrodes and a relative position of the electrodes can be determined.

A position of the tip and ring can be determined in block 658. The collection of the electrode impedance data in block 656 can be used to determine the position in block 658. The collection of the tip and ring electrode impedance data in block 656 for determining the position in block 658, can be performed substantially immediately after both the tip and ring electrodes are within the patient 26. Accordingly, positioning the tip and ring instrument in the patient 26 in block 654 can simply be positioning the tip and ring electrodes within the patient 26 so that they can be used to measure an initial or first impedance within the patient 26.

A vector can be calculated from the ring to the tip based upon the determined position of both the tip and ring electrodes in block 660. As discussed above, the ring electrode can simply be an electrode that is proximal to the tip electrode. Accordingly, the vector can be understood to be a vector that is defined from a proximal electrode through a distal electrode. Additionally, as discussed above, determining the position of the tip and ring can be performed substantially immediately after placing the tip and ring electrodes within the patient 26. Thus, the initial measurement can be a standard or undistorted measurement of the relative position of the tip and ring.

Also, the first measurement may include a plurality of first measurements. For example, a first measurement in each of the axis that are generated within the patient can be made. Thus, calibration or error correction can be made for each of the axis. Moreover, the calibration can be performed once the mapping catheter 100 is positioned within the heart 80. Accordingly, identifying the portion of the heart 80 for a location of the mapping catheter 100 can be used to assist in calibration of the PSU 40.

As discussed herein, the flowchart 650 illustrates a method of correction or accounting for distortion in a current or sensed impedance within the patient 26. Accordingly, the correction using the flowchart 650 can be used to ensure that all or substantially all of the impedance measurements collected within the patient 26 used to plot map data points 198 are positioned at a known or similar position relative to one another. In other words, using a standard or calibrated distance of the tip from the ring allows distortion of the determined or measured distances between the two to be reduced or eliminated.

After a vector is calculated based upon a determined position of the tip and ring electrodes in block 660, a distance can be selected from the ring electrode in block 662. The distance from the ring electrode can be the measured distance from the ring electrode to the tip electrode, also based upon the determined position of the tip and ring electrodes in block 658. Alternatively, any appropriate distance can be selected for the tip electrode from the ring electrode. For example, it may be selected to determine a distance that is slightly less than the physical distance of the tip electrode from the ring electrode to ensure that the tip electrode is touching or imbedded a selected distance into a physical surface when displaying the tip electrode is at or on a surface. Alternatively, it can be selected to determine a distance in block 662 that is greater than the physical position of the tip electrode from the ring electrode. This ensures that there is a space between the tip electrode and any surface when it is displayed that the tip is at a mapped surface. For example, if a surface is determined with the mapping catheter 100 and the lead 120 is to be implanted, it can be selected to navigate the lead 120 to an implanted location with the illustrated map data, but while attempting to maintain a distance between the lead 120 and any surface of the patient 26 prior to implantation of the lead 120 into the patient.

Once the vector is calculated in block 660 and a distance from the ring electrode is determined in block 662, a plotted position of the ring can be performed in block 664. Additionally, a point along the vector calculated in block 660 and at the distance selected in block 662 can be plotted in block 666. After plotting the position of the ring electrode and plotting the position of the second point in blocks 664, 666 respectively, two points can be plotted that represent a position of the ring electrode and the tip electrode. As discussed above, a measurement of an impedance of the ring and tip electrodes can be performed in block 656. Accordingly, the PSU 40, which the tip and ring instrument can be a part of, can determine a position of the ring electrode based upon the measured impedance. The measurement of the impedance at the ring electrode can be used to plot the position of the ring electrode based upon its determined position in block 658. However, to correct for various distortions, calculating or selecting a distance of the ring electrode from the tip electrode in block 662, can ensure that all measurements or plotting of the tip electrode are the same. In other words, rather than determining two positions individually for each electrode, only one is determined by measurements. Thus, distortion can be reduced or eliminated for the display of two points if the second is always a fixed distance from the first. Also, the determination of position can be made for only one electrode and the position or orientation of the second as only a direction from the first.

Decision block 668 is used to determine whether more data are to be collected. If the YES routine 670 is followed, then measurements of impedance at the tip and ring electrodes can be performed in block 656. A second decision block can be used to determine whether the measurement in block 656 was a first measurement in block 672. If the YES routine is followed in 674, then a determined position of the tip and ring, calculated vector in block 660, and selected distance can be performed in block 662. If the NO routine is followed in 676, for example, if a vector has already been calculated in block 660 and distance has already been selected in block 662, a position of the ring electrode can be determined in block 678 based upon the subsequent measurement. A position of the ring can then be plotted in block 664 based upon the determined position in block 668. Further, a position of the second point can be plotted in block 666 based upon the calculated vector and selected distance in blocks 660, 662.

If no further data is collected in block 668, then the NO routine 660 can be followed to optionally render the map data points 198 or the surface 281 in block 682 or to end the procedure in block 684. It will be understood, that rendering a surface in block 662 is optional, at least because the correction method in the flowchart 650 can simply be a calibration procedure.

To graphically illustrate the differences between collecting data with an uncorrected and with a corrected tipping ring or dual electrode position, FIGS. 18A and 18B illustrate icons representing a dual electrode or tip and ring instrument in an uncorrected and corrected display, respectively. FIGS. 19A and 19B also illustrate a plurality of map data points illustrated on the display 58, also in both an uncorrected and corrected manner, respectively. Briefly, without correction, the data in FIGS. 18A and 19A is more spread out and distorted than in corrected FIGS. 18B and 19B.

With additional reference to FIG. 18A, an icon 100' can be illustrated on the display 58. The icon 100' can include a first icon portion illustrating the determined or measured position uncorrected of the ring electrode 110$u$C. The display 58 can further include an icon portion illustrating a position of the tip electrode 108 as an icon 108$u$C. The uncorrected positions of the ring and tip electrodes 110$u$C, 108$u$C, can be determined to be a position or distance $D_{UC}$ apart. The distance $D_{UC}$ can be a determined distance based only upon the measured distance or measured impedance at the two electrodes, such as the ring and tip electrodes, 110, 108 of the mapping catheter 100.

As illustrated in FIG. 18B, however, the display 58 can display an icon of the mapping catheter 100 relative to map data points 198 and further include a first icon portion representing a corrected position of the ring electrode 110$c$ and a second icon portion representing a corrected location of the tip electrode 108$c$. The distance between the corrected ring electrodes $D_c$ can be less than, greater than, or any corrected distance relative to the uncorrected distance $D_{uc}$. As discussed above, during an initial or first placement of the mapping catheter 100 within the patient 26, a distance can be selected of the tip electrode from the ring electrode. The distance selected can be used to illustrate the corrected position of the icon 108c relative to the ring electrode 110c icon. The corrected distance can be a calibrated distance that is to maintain the selected or measured distance on the display 58 for all points that are measured within the ring electrode when illustrating the tip electrode relative thereto.

As illustrated in FIG. 19A, when the map data points 198 are displayed on the display device 58, uncorrected map data points 198uc may be expanded where a distance may be present between various map data points such as in regions 198uc' and 198uc" compared to corrected or calibrated map data points 198c illustrated in FIG. 19B. A more compact region of the map data points can be seen in regions 198c' and region 198c" in FIG. 19B, The region 198uc' compared to the region 198c' illustrates that the corrected data illustrates more compact map data points in the corrected map data 198c. The compact data and the corrected map data point 198c are based upon the substantially known and unchanging position of the ring electrode relative to a distal tip of the instrument, which can include the tip electrode 108. Within the patient 26, however, the measured impedance may be altered due to lateral (or distorted) electrical current flow within the patient, soft tissue within the patient, or other distortion causing features of the patient 26. Although the measured distance of the tip electrode relative to the ring electrode may differ based upon the distortions, the physical position of the tip electrode relative to the ring electrode can be substantially fixed based upon the physical properties of the mapping catheter. Accordingly, accounting for the physical properties of the mapping catheter, a single measure of points, such as a measured point of the ring electrode, can be used to map at least two points relative to the ring electrode. Also, the ring electrode is less likely to extend to or near a chest or thorax wall and, therefore, is less likely to be close to the outside of the body and therefore, more likely to measure an accurate position than a tip electrode.

It will be understood that although the method illustrated in the flowchart 650 is discussed to determine a position of a distal tip electrode relative to a more proximal electrode that the alternative or reverse may also be performed. For example, a corrected or calibrated position of a proximal electrode can be determined relative to a distal electrode by determining a vector from the distal electrode towards the proximal electrode and selecting a distance between the two. Accordingly, measuring from the ring electrode or any proximal electrode is not necessary.

In addition, it will be understood, that the PSU 40 can allow the user to select display types or simultaneously view both corrected and uncorrected map data points. Therefore both corrected and uncorrected map data points can be displayed on the display 58. They can be displayed sequentially on a same area of the display or next to each other on the display 58 for view by the user 22. In addition, it will be understood that the map data points 198 can be illustrated alone, as illustrated in FIGS. 19A and 19B, or a surface can be rendered and displayed without the map data points 198. The rendered surface can be generated or based upon the corrected or uncorrected data points and a corrected or uncorrected surface can also be displayed on the display 58 similar to the map data points 198.

According to various embodiments, the correction for the position or distance between two or more measuring electrodes within the patient can include a scaling factor that can be used to correct the map of data. This can be an alternative to or in addition to the method 650 illustrated in FIG. 17. The scaling factor can be determined based upon points identified or determined of the two electrodes positioned relative to one another. The two electrodes, such as on the mapped catheter 100, can be substantially fixed relative to one another for the correction procedures. The position of the two electrodes can be collected continuously during a procedure or at any appropriate time. The scaling factor can be used to correct the map, such as the map data points 198 or the surface 281.

With Reference to FIG. 20, a method of formulating a scaling factor and interpolating the map data 194 is illustrated in the scaling factor interpolation (SFI) flow chart 421. In the SFI flowchart 421, the method can begin in Start block 423. The volume or surface to be mapped can then be explored and mapped in an acquire map data or points block 425.

As previously discussed, the mapping catheter 100 can include two or more electrodes, such as the tip and ring electrodes 108, 100 (although any instrument can include any appropriate number of electrodes, and only two electrodes are discussed for simplicity of the present discussion). Each of the electrodes can be used to measure impedance within the volume, such as within the heart 80 of the patient 21. During each cycle of acquisition, the PSU 40 can also determine the measured distance between the two electrodes 108, 110. The distance between the two electrodes 108, 110 can be known based upon an input or predetermined distance. The known distance can be recalled in block 427 from a memory or input system.

The measured distance can be compared to the known or input distance. The comparison can be used to determine a scaling factor in block 429. Because the map data can be three dimensional, a scaling factor in each of three coordinates, x, y, and z can be determined. The scaling factor can be determined for one or any appropriate number "n" of points. Thus, scaling factors $r_{nx}$, $r_{ny}$, and $r_{nz}$ can be determined for n points of map data 194.

The scaling factors $r_{nx}$, $r_{ny}$, and $r_{nz}$ can all be determined based on the initial of determined scaling factor based on a distance between at least two electrodes or position elements on the instrument, such as the electrodes 108, 110 on the mapping catheter. The two electrodes 108, 110 will be at relative positions to one another in three dimensions. Accordingly, the scalar distance can be calculated based on the known orientation between the two electrodes 108, 110 and applied to the map data in the three dimensions.

The scalar distance can be used to determine a vector based on a measured or determined orientation of the two electrodes 108, 110 relative to one another when collecting the map data. A correction vector based on the scalar distance and a determined three dimensional position of the tip electrode 108 and the ring electrode 110. The correction vector, using the scalar value or distance, can then be used to determine a scalar value in all three dimensions to determined or generate the scaling factors $r_{nx}$, $r_{ny}$, and $r_{nz}$.

Using the scaling factors $r_{nx}$, $r_{ny}$, and $r_{nz}$ the measured or sensed positions of the electrodes 108, 110 that generate the map data points 194 can then be corrected to generate an interpolated map data in block 431. The interpolated data can be similar or identical to that in FIG. 19B, which is corrected data. The uninterpolated data can be similar or identical to the uncorrected data in FIG. 19A. As illustrated above, in FIGS. 19A and 19B, the difference between the interpolated and un-interpolated data can be significant if distortions exist in the various currents used to generate the map data points. The interpolation can be performed with any appropriate algorithm, such as the griddata3 function of Matlab® computer software, sold by MathWorks Inc. The interpolation can correct each measured map data point to a corrected or interpolated map data point.

In essence, the scaling factor is a difference, such as a mathematical ratio, between the determined position in the acquired map data points of the electrodes and the known position of the electrodes. If the map data points determine that the two electrodes are 3 cm apart, but it is known that they are 2 cm apart then the scaling factor serves to normalize the measured data. Further, because the data can be collected in three spatial dimensions the scaling factor can be determined and applied in all three spatial dimensions.

The interpolated map data can be displayed on the display 58 in block 433. As illustrated in FIG. 19B, the interpolated or corrected map data can correct for distortions. Further, the map data can be displayed as points 198 and/or the surface 281. The interpolated map data can then be used for navigation or guidance, if selected, in block 435. It is not required, however, that the interpolated data, or any data, be used for navigation. The method can then end on block 437.

Virtual Map Data

The map data, whether corrected or not, can be collected solely by measuring impedances with electrodes, such as with the mapping catheter 100. Map data, however, can also be determined by knowing the dimensions or surface of a physical structure relative to the electrodes measuring impedance or other tracking members. As illustrated in FIGS. 21A-21C, virtual map data points can be collected or determined relative to the mapping catheter 100. The map data can be collected based on knowing or determining relative locations of an instrument used to collect the map data points. Thus, the map data points or the surface, illustrated for viewing by the user 22, according to various embodiments can be generated and displayed without requiring information from another imaging system, such as a fluoroscope, MRI, etc.

The map data points 198 illustrated on the screen or display 58 can be points that are generated based upon a sensed or measured impedance within the patient 26, as discussed above. In addition, the data that is illustrated as the map data points 198 is based upon map data 194 collected with the PSU 40. As illustrated in FIG. 21a, the map point 194 can be based upon an actual measurement of a voltage or bioimpedance at selected locations within the patient 26. For example, the impedance measured at the tip electrode 108 and the ring electrode 110 can be used to determine a position of the specific location or relative location of the tip and ring electrodes 108, 110.

In addition to the actual positions of the tip and ring electrodes 110, 108 that are measured with the mapping catheter 100, various positions that are known locations relative to the ring and tip electrode can also be inferred by the PSU 40. The PSU 40, as discussed above, can include a processor that is interconnected with a memory system that can store executable instructions for various calculations. Calculations can include the determination of relative or inferred or determined positions of various physical portions of the mapping catheter 100 relative to the two electrodes of the tip and ring, 108, 110.

Exemplary inferred positions can include points on or a complete surface of a physical structure of the mapping instrument or catheter 100. As discussed above, the mapping catheter 100 can include the balloon 102 that is inflated between the tip and ring electrodes. The balloon can include a known physical dimension, such as a diameter that can be used to infer or determine one or more points or a surface along a sphere between the tip and ring electrodes 108, 110. These points or surface, also referred to as virtual points or surface, can be inferred or determined based upon the measured impedances of the tip and ring electrodes 108, 110. The virtual surface can be defined by a plurality of virtual points defined on the physical surface of the mapping instrument.

As illustrated in FIG. 21A, if and when only the measured impedances of the tip and ring electrodes 108, 110 are used to determine map points 194 there are only two points that can be measured per time step or measurement instant. Points 108p and 110p can correspond to the two points of the measured impedance with the tip electrode 108 and the ring electrode 110, respectively. These points can be displayed on the display 58 as map data points 198 and can be used to accumulate a plurality of points for illustrating the surface 281. Because the balloon 102 is positioned at a fixed location between the tip and ring electrodes 108, 110, and if inflated sufficiently so when in blood, does not noticeably compress, the surface of the balloon 102 can also be used to identify known points relative to the tip and ring electrodes 108, 110.

Determining points on the surface of the balloon 102 uses the known geometry of the balloon 102 relative to the tip electrode 108 and the ring electrode 110. Once the balloon 102 is inflated, it can be substantially rigid and at a fixed location between the tip and ring electrodes 108, 110. This allows the surface of the balloon 102 to be defined relative to the tip and ring electrodes 108, 110. For example, a center of the balloon can be identified as 102c and as a point along a line between the tip and ring electrodes 108, 110. The geometry of the balloon relative to its center 102c can be any appropriate geometry. For example, the balloon 102 can be substantially a perfect sphere. Accordingly, the surface of the sphere can be determined relative to the center 102c. Alternatively, as illustrated in FIG. 21B, the balloon 102 can have an ovoid shape. Regardless, the surface of the balloon 102 can be determined relative to its center 102c and the two electrodes at the tip and ring 108, 110 of the mapping catheter 100.

Once the surface of the balloon 102 is determined relative to the tip and ring electrodes 108, 110, the surface of the balloon 102 can be used to generate map data 194 in addition to the two points based only upon the measured impedance of the tip and ring electrodes 108, 110. For example, at each time increment where an impedance measurement is taken from the tip and ring electrodes 108, 110, a determination of one or more points defined by a surface of the balloon 102 can be determined. For example, as illustrated in FIG. 21B, surface point's 102p1-102p6 can be determined. As illustrated in FIG. 21C, it will be understood that the balloon 102 is a substantially three dimensional object. Accordingly, points around the surface can be determined, which can include a point 102p7 that can be across or substantially opposite the point 102p2 and rotationally offset from other points 102p1 and 102p3 by 90 degrees or about 90 degrees.

The determined points of the surface of the balloon 102 need not be specifically measured or be based upon a measurement of an impedance within the patient 26. Rather, the points on the surface of the balloon 102 can be determined as specific location relative to the locations of the tip and ring electrodes 108, 110 based upon the impedance measurements at the tip and ring electrodes 108, 110. Accordingly, each time a measurement is taken of an impedance with the tip and ring electrodes 108, 110 and positions of the ring and tip electrodes 110, 108 are determined based upon the impendence measurements, a number of points defined by a surface of the balloon 102 can also be determined. The points defined by the balloon 102 can be determined by calculating the geometry of the points of the balloon 102 relative to the tip and ring electrodes 108, 110. Each of the points determined relative to the balloon 102, based upon the geometry of the balloon 102 relative to the tip and ring electrodes 108, 110, can also be used to add to the map data 194 for the PSU 40. This can be used to substantially increase the number of map data 194 calculated or collected for each time increment of collecting the map data 194 with the mapping catheter 100.

In addition, the balloon 102 can be expanded to have an exterior diameter or geometry greater than an external geometry of the catheter 100 and can contact the surface of a structure, such as the heart 80, even though the tip and ring electrodes 108, 110 need not specifically contact the surface. Accordingly, the balloon 102 can contact a surface while the tip and ring electrodes 108, 110 do not and this allows a determination of a position of a surface while only measuring impedance at the tip and ring electrodes 108, 110. This is because the position of the surface of the balloon 102 is known relative to the tip and ring electrodes 108, 110 and points on the surface of the balloon 102 can be used to determine map data 194 based upon the known geometry of the balloon as discussed above.

A mapping catheter 100 that includes the balloon 102 and the electrodes 108, 110 can have a substantially fixed geometry near or between the electrodes 108, 110. The balloon 102 can be expanded to a fixed and known geometry between the two electrodes 108, 110. Because of the fixed geometry of the balloon 102, the virtual points 102p defined by the balloon 102 can be known based upon the measured and determined positions of the electrodes 108, 110.

A virtual point on the balloon 102, such as the point 102p4, can be calculated to be at a specific axial location between the electrodes 108, 110 and at a distance from the longitudinal axis of the mapping catheter 100, and also at a known angle or orientation relative to the mapping catheter 100. The calculation of the virtual point 102p4 can be made substantially continuously with a processor, such as a processor of the PSU 40. In addition, or alternatively, the location of each of the virtual points 102p can be calculated relative to the electrodes 108, 110 and collected substantially continuously during the measurements taken with the electrodes 108, 110. Regardless of the method, multiple data points can be collected and generated for each of the measured impedances with the electrodes 108, 110.

Pathway Icon

A pathway icon 456 can be displayed on the display device 58, as illustrated in FIGS. 22A and 22B. The pathway icon 456 can assist the user 22 in returning a second instrument or a path previously identified. The path can be generated with a first instrument during a first time in a procedure. As discussed herein, the pathway icon 456 can be generated based substantially only or entirely on determined positions of the first instrument, such as the mapping catheter 100 prior to insertion of a second instrument, such as the lead 120. Accordingly, the pathway icon can be generated only with the PSU 40.

Map data points 198, illustrations of the map data 194, can be illustrated on the display 58 to illustrate a surface of a portion of the patient 26, such as a surface of the heart 80. As discussed above, the illustrated surface or information regarding the patient 26 can be used for determining an implantation or positioning of an implant, such as the lead 120 for an implantable medical device. A lead, such as the lead 120, can be positioned in the patient 26 in any appropriate manner. Nevertheless, the lead, such as the lead 120, is generally positioned in the patient 26 subsequent to the mapping of the selected portion of the patient 26 and even subsequent to removal of the mapping catheter 100. The user 22 can determine appropriate or selected positions for implantation of the lead 120 within the patient 26 using the map data points 198 on the display 58.

Information can be displayed relative to the map data points 198 or the surface 281 on the display 58 to identify a selected location or appropriate location for implantation of the lead 120. The user 22 can identify points on the display 58 and have an icon illustrated on the display 58 relative to the map data points 198 or the surface 281 to assist in later positioning of the lead 120 relative to the patient 26. As discussed above, the lead 120 can be tracked or its position can be determined by the PSU 40 or any other appropriate tracking system. Accordingly, the position of the lead 120 can be illustrated on the display 58 relative to the map data points 198.

As exemplary illustrated in FIG. 22A, the surface 281 can be illustrated on the display 58 based upon the map data 194. The surface 281 can be any appropriate surface, such as a surface illustrating a portion of the patient's heart 80. A landmark icon 450 can be illustrated relative to the surface data 281 that can identify or be used as a marker for identification of a position for implantation of the lead 120. As discussed above, various information can be used to identify the position for the implantation such as pressure data, motion data, and other data including the map surface 281.

Illustrated in FIG. 22A, as the user 22 withdraws the mapping catheter 100, the tip icon 108' can be illustrated on the display 58. In addition, an elongated tube icon 456 can be illustrated relative to the surface data 281. The elongated tube icon 456 can also be referred to as a driveway or pathway icon to be used during an implantation procedure. The pathway icon 456 can be generated based upon identifying or determining a diameter and drawing a three dimensional cylinder or tube around points determined with the mapping catheter 100. It will be understood that the pathway icon 456 can be generated in any appropriate manner, and can include defining a substantially continuous line interconnecting multiple determined position of the electrodes 108, 110 of the mapping catheter 100 as it is withdrawn from the patient 26. Also, the pathway icon 456 can be generated and illustrated at any appropriate time.

The pathway icon 456 can be a substantially three dimensional icon generated relative to the mapping data, such as the surface 281. The three dimensional nature of the pathway 456 can be used to assist the user 22 in guiding the lead 120 back to the position of the implantation represented with the icon 450. As discussed above, removal of the mapping catheter 100 from the patient 26 can be performed after identifying the location for implantation and representing it with the icon 450. Accordingly, the path of removal of the mapping catheter 100 can represent at least one pathway, which can include the most efficient pathway, to return to the implantation site represented by the icon 450.

In addition, the mapping catheter 100 can be placed within the patient 26, via a deflectable or steerable sheath, as is known in the art. Accordingly, the removal of the mapping catheter 100 can be through the sheath allowing for a substantially smooth and efficient removal of the mapping catheter 100. Although the mapping catheter may be within the sheath, determining a position of the mapping catheter 100 within the sheath can be done with the PSU 40. For example, as discussed herein, the sheath may include a plurality of holes or windows to allow for body fluids to enter the sheath to assist in or allowing the mapping catheter 100 to measure an impedance within the sheath.

Once the mapping catheter 100 has been removed from the patient, the lead 120 can be positioned into the patient. As illustrated in FIGS. 22B and 22C, the position of the lead 120 can be illustrated on the display 58 with an icon 120'. The icon 120' can identify the position of the implantable electrode or any other portion on the lead 120. The pathway icon 456 can be displayed on the display 58 relative to the displayed surface 281 or any other appropriate data on the display 58. The pathway icon 456 can identify a selected pathway for moving the lead 120 to the position for implantation represented by the icon 450.

As illustrated in FIG. 22B, the lead 120, represented by the icon 120', can be followed or moved along the pathway icon 456 by the user 22. The substantially three dimensional nature of the data can be more easily visualized in FIG. 22C that illustrates that the icon 120', representing the position of the lead 120, can be illustrated within a three dimensional tube of the pathway icon 456. It will be understood that a single display, such as the display 58, can illustrate perspective views of the pathway icon 456 and the lead icon 120', as illustrated in both FIGS. 22B and 22C. Accordingly, more than one view of the lead icon 120' relative to the pathway icon 456 can be illustrated on the display 58. Regardless of the perspective provided, the pathway icon 456 can be used by the user 22 to assist in positioning the lead 120 to the selected implantation site represented by the icon 450.

The mapping data 194 of the patient 26, for example illustrated by the surface 281, can be substantially three dimensional. Thus, providing a three dimensional view of the pathway icon 456 can assist in assuring that the appropriate path is followed by the lead 120. The path or position of the lead 120 can be illustrated by the lead icon 120'. In maintaining the lead icon 120' at a selected position relative to the pathway icon 456 the selected path of the lead 120 can be maintained within the patent 26. This may be helpful if the position for implantation represented by the implantation icon 450 is within or near an anatomical feature that may require a specific three dimensional positioning or approach of the lead 120.

Cannulation and Surface Refinement

To better illustrate small or hard to find surface features, a blank or smooth surface can be generated, as illustrated in FIG. 23A. The mapping catheter 100 can be moved and a surface 480 can be augmented to clearly show small deviations relative to a flat or smooth surrounding. Also, additional measurements, such as temperature, can be used to determine locations of anatomical structures.

The surface 281 can be displayed on the display device 58 to illustrate a surface based on the map data collected with the mapping catheter 100 or other appropriate instrument. Alternatively, or in addition thereto, map data points 198 can be displayed on the display 58 as well. The various points and surfaces generated and displayed on the display 58 are based on, according to various embodiments, positions determined by measurements of impedance with the PSU 40. The surface generated based on incremental or additive measurements can be referred to as a positive surface. In other words, the positive surface is based upon map data 194 that is generated based only upon measurements of impedance by a mapping instrument, such as the mapping catheter 100 in an additive process. In the additive process, each new point is added to the previous set of points and a surface can be generated based upon the complete set of points or any portion of the set of points. Various portions of the anatomy, however, may be hard to visualize or find using an additive process. For example, during positioning of an implant in a left portion of the patient's heart atrium, it may be selected to identify a coronary sinus ostium. Identifying the ostium may be difficult if the position of the ostium is not identified.

During the additive process, additional points are added to the mapping data 194 and illustrated as the map data points 198 or the surface 281. Therefore, depressions or small crevices may be difficult to identify and enhance. However, if a surface or volume were generated and a portion removed from the volume in a subtractive or inverse process, a small structure can be easily identified within a large, undisturbed area. In the subtractive or inverse mapping process, the mapping catheter 100 can be used to identify points where a surface is not. Accordingly, rather than building or adding to map points 194 or managed or map data points 198, as discussed above, points can be removed from the volume or surface to illustrate an area where anatomical structures are not present. This can be used to identify where an anatomical structure is present.

As illustrated in FIG. 23A, according to various embodiments, an internal view of the surface 281 can be viewed. For example, a slice or cross section 484 can be generated to allow viewing of an interior of a surface or structure, such as an interior of the heart 80. A virtual filled or pristine volume or surface 480 can also be generated (e.g. a generated filled volume) in a selected portion of the display 58 relative to the surface 281. The volume 480 can be any appropriate shape or surface geometry and is illustrated as a cube simply for this discussion. Further, the volume 480 is a virtual volume that is generated by a processor, such as a processor of the PSU 40 and displayed relative to a the surface 281 or map data points 198. A probe icon 482, which can be an icon representing the position of the mapping catheter 100, can also be displayed on the display 58.

As illustrated in FIG. 23A, the complete volume 480 can be displayed to illustrate a substantially virtual pristine surface or volume relative to the surface 281. The pristine volume 480 can generally be understood to be within the volume defined by and over the surface 281, for example within the cutaway or slice view of the surface 281, the cross section portion 484. The pristine volume 480 can be positioned at a selected region or to cover a selected region, such as a region that may include the coronary sinus ostium.

With reference to FIG. 23B, the mapping catheter 482 can be moved relative to the pristine surface 480 to generate a disturbed or inverse mapping volume 480'. The inverse mapping volume 480' can include an inverse or subtracted region 486. The subtracted region can be bound by an edge 488 that can be used to identify a portion of the anatomy of the patient 26. As discussed above, the coronary sinus ostium may be identified relative to the patient 26 by a depression or other appropriate geometry of the patient's 26 anatomy.

Accordingly, the subtracted region 486 can be identified or illustrated as a depression relative to the disturbed volume 480'. The subtracted region 486 can be determined as that part of the heart 80 that does not include a physical wall rather than only a portion of the virtual surface generated relative to the previously acquired map data. To form the subtracted region 486, rather than adding map data 198 points or managed points to a data set, map data points 198 or managed points can be removed based upon tracking the position of the mapping catheter 100, as illustrated on the display by the icon 482. As map data points are removed from the pristine volume 480, to generate the disturbed volume 480', an anatomical region can be identified and illustrated. The anatomical region can be clearly illustrated and seen relative to the remaining undisturbed portions 490 relative to the subtracted portion 486. The substantially sharp edge 488 surrounding subtracted region 486 can be used to efficiently or quickly identify portions of the anatomy of the patient 26. The edge 488 can be identified by the user 22 or substantially automatically with a processor, such as the processor of the PSU 40 or other appropriate processor.

The subtracted portion 486 can be generated substantially similarly to generating a data set of map data, as discussed above. Rather than adding map data to a data set, however, map data, map data points 198, or manage points within the pristine volume 480 are removed. Accordingly, the pristine volume 480 can be a complete set of points within a selected region relative to the surface 281. The map data that is determined with the mapping catheter 100, as illustrated by the icon 482, can be those points that are based upon a determined position of the mapping catheter 100 by measuring an impedance with an electrode on the mapping catheter 100. By removing these points from the pristine surface or volume 480, the subtracted region 486 is clearly illustrated.

The subtracted region 486 can then be illustrated alone, with the other map data points generated or determined, relative to generated the surface 281 without a remaining pristine portion 490. By removing the remaining pristine portion 490 from the augmented or disturbed volume 480', a view of the anatomy of the patient 26 can be more usefully displayed. As discussed above, the pristine volume 480 is not based upon mapping data relative to the patient 26, but merely describes or includes a data set of an entire volume of points. Accordingly, the pristine volume 480 is not based upon the patient's 26 anatomy, but is used to efficiently generate the subtracted region 486. Also, the subtracted region 486 can be illustrated relative to the surface 281 either from an internal or external view. As illustrated, the subtracted region 486 can be viewed from the interior of the surface 281.

Thus, the subtracted region 486 can be used for identifying anatomical portions of the patient 26, such as the coronary sinus ostium. The coronary sinus ostium or other portions can be used for landmark identification and performing a selected procedure relative to the patient 26. Other anatomical depressions or crevices can also be identified. In addition, a volume can be generated relative to any portion, as selected by the user 22 or automatically. This can allow the user 22 to explore any selected region for a depression or crevice as selected by the user 22. For example, the user can examine an area of an infarct for diseased or necrotic tissue.

In addition to mapping and illustrating the map data points 198 or the surface 281 on the display 58, various techniques can be used to easily illustrate various anatomical structures. Identification of the coronary sinus can be used for cannulation of the coronary sinus or placement of leads in the patient 26 can be performed. Also, other anatomical features can be identified in the patient 26.

Identification of anatomical features can be for cannulation. As illustrated in FIG. 24A, the heart 80 generally includes several and various anatomical structures. Generally, for discussion of cannulation of the coronary sinus, the anatomical structures can include the superior vena cava (SVC) 500, which enters a right atrium (RA) 502 and an inferior vena cava (IVC) 504 that can exit the RA 502. Near the right atrium 502, a tricuspid valve (TCV) structure 506 separates the RA 502 from a right ventricle (RV) 508. Within the RA 502 is the coronary sinus ostium (CSO) 510. As discussed above, for a mapping catheter, such as the mapping catheter 100 including the balloon 102, can be moved through the patient 26 to map various anatomical structures. For example, cannulation of the coronary sinus can assist in the identification of position and locations for implanting leads into the patient 26. By positioning the mapping catheter 100 through the CSO 510 cannulation of the CSO 510 can occur.

Various map data points can be illustrated on the display 58 or a surface can be rendered to illustrate cannulation of the CSO 510. As illustrated in FIG. 24B, a surface 281c can be used to illustrate the ostium of the CSO 510 by illustrating a surface 510'. Any appropriate views of the surface 281c can be displayed on the display 58 to provide the user 22 varying perspectives of the surface 281c.

The data points used to generate the surface 281c can be generated as the mapping catheter 100 passes through the SVC 500, illustrated on the display 59 as surface 500', into the RA 502, illustrated on the display 58 as the surface 502'. As illustrated in FIGS. 23A and 24B, the mapping catheter 100 can be moved through the patient 26 as discussed above. As the mapping catheter 100 is moved through the patient 26, the ring and tip electrodes 108, 110 can be used to measure impedance within the patient 26 to determine or generate the map data points and surface 281, 281c as discussed above.

Alternatively, various other instrumentation can be used such as a mapping catheter 520 that includes a balloon 522, as illustrated in FIG. 25. The mapping catheter 520 can be any appropriate catheter, such as the model 6215 catheter sold by Medtronic, Inc. having a place of business in Minneapolis, Minn., USA. The mapping catheter 520 can be positioned through a deflectable sheath 524, which can include any appropriate deflectable sheath such as the model C304 deflectable sheath sold by Medtronic, Inc. having a place of business in Minneapolis, Minn., USA.

A guide wire 526 can also be positioned through a lumen 527 defined by the mapping catheter 520. The guide wire 526 can be positioned to be exposed and extend a selected distance 526d, such as about 1 to 2 millimeters, past a distal end 522d of the balloon 522. An exposed portion of the guide wire 526e can allow the guide wire 526 to be used to measure impedance within the patient 26. Accordingly, the mapping catheter 100 can be replaced or augmented with the mapping catheter 520 for measuring a bio-impedance or voltage within the patient 26 and generating or collecting the mapping data 194 for illustration on the display 58 as the map data points 198 or the surface 281.

The guidewire 526 can include a diameter or other cross-sectional dimension that is less than that of the catheter, such as the mapping catheter 100. The guidewire 526, therefore, can be introduced in to small enclosures and used to determine fine or small movements of a position element defines by the exposed portion of the guidewire 526. To this end the guidewire 526 can be used to assist in identifying the CSOS and other small areas. The guidewire 526 can, therefore, be used to identify regions for cannulation or that are cannulated.

It will also be understood, according to various embodiments, that any appropriate navigation or tracking system can be used to determine map and data points for display on the display 58. Accordingly, the map data points 198 that are displayed on the display 58 can be generated with a tracking system such as an electromagnetic tracking system. The electromagnetic tracking system can be any appropriate tracking system, such as the Stealthstation® Axiem® System for Electromagnetic Tracking sold by Medtronic Navigation, Inc., having a place of business in Louisville, Colo., USA. The electromagnetic tracking system can be used to determine a location of the mapping catheter, such as the mapping catheter 100 or the mapping catheter 520, in any appropriate manner. For example, an electromagnetic sensing coil or electromagnetic tracking device can be positioned on the mapping catheter 100 or the mapping catheter 520. According to various embodiments, an electromagnetic tracking device can be included or formed within the guide wire 526 to track the mapping catheter 520 within the patient 26. Similarly, a tracking device can be formed within the mapping catheter 100, such as a wire coil formed near the tip electrode 108, the ring electrode 110, or at any appropriate location along the mapping catheter 100. Accordingly, the map data points 198 can be generated or determined using any appropriate tracking system and the PSU 40 can be used to illustrate the map data points 198 or a surface 281 on a display device 58.

The surface 281 can also be updated in substantially real time according to various embodiments. For example, a rotating buffer system or an update area can be used to illustrate the surface 281 in substantially real time. Techniques for displaying the surface 281 as data points are added to the surface points 281 are described in co-pending U.S. Provisional Patent Application No. 60/105,597, filed on Oct. 16, 2008 and incorporated herein by reference.

In addition to identifying various anatomical structures, such as a depression as discussed above with map data points, other information can be acquired regarding the heart 80 of the patient 26 to assist in the determination of various anatomical structures or features. For example, one or more temperature sensors, such as a thermal couple, can be included on the mapping catheter 100. A thermocouple, thermosistor, temperature sensitive integrated circuits, or other appropriate temperature measuring devices can be positioned at any appropriate location such as near the electrodes of the mapping catheter 100. By positioning a temperature sensor on the mapping catheter 100, a temperature signal can be transmitted to the PSU 40 at the location of the mapping catheter 100. The position of the temperature sensor can be known relative to the electrodes of the mapping catheter 100 so that the temperature of a specific map data point can be determined. Although temperature is an example of any appropriate condition that can be sensed, such as pressure, flow rate, etc.

Various regions of the patient 26 can include a temperature differential based upon a proximity of an anatomical structure. The anatomical structure can be any anatomical structure, for example, the coronary sinus ostium 510 illustrated in FIG. 24A. Coronary sinus drains blood from the heart's circulation so it is generally warmer blood than blood returned from the systemic circulation.

As illustrated in FIG. 24C, temperature indicating map data points 510" or surface 510''' can be displayed on the display 58 relative to the mapped data points 198 or the surface 241 of the heart 80. The mapped data points or area 510" can include a feature, such as a color, contrast, blink rate, or the like, to identify a temperature relative to other or surrounding surface areas or map data points. As illustrated on the left portion of the display 58, the temperature map data points 510" can include a color that is darker than the other map data points 198. The color may indicate a higher relative or absolute temperature, which can indicate that they are near the coronary sinus 510. A temperature of the blood in the region of the coronary sinus 510" can be higher than blood in other areas of the heart 80. A threshold can be selected for determining whether a different color should be displayed or a gradient of many colors can be selected. Further, rather than a color other indicia of temperature change can be provided.

When the temperature differential is illustrated on the display 58, such as with mapped data points or surface 510", relative to the remaining mapped data points 198 or surface area 241, the user 22 can identify a region of the temperature differential. The region of the temperature differential can help identify the anatomical structure. The anatomical structure can be further displayed on the display 58, such as with the removed region 486, as illustrated in FIG. 23B. Therefore, it will be understood, that multiple information can be displayed on the display 58 to assist in identifying anatomical structures and features. It would be further understood that measuring a temperature in any appropriate location of the anatomy can assist in identifying anatomical structures in that portion of the anatomy. It will be further understood that a processor, such as a processor of the PSU 40, can be used to identify anatomical structures based on the temperature differential. Alternatively, or in addition thereto, the user 22 either alone or with the assistance of the processor can identify anatomical features based upon the measured temperature.

State or Location Determination System

The heart 80 of the patient can include one or more measurable features or characteristics that can be used to identify or determine a state or a location of the instrument measuring the feature. For example, the mapping catheter 100 or the lead 120 can be used to measure pressure or an electrogram (EGM) within the patient 20 to assist in identifying a specific location within the patient 26. In identifying a location within the patient 26, the user 22 can obtain additional location and orientation information relating to the information displayed on the display device 56, such as a rendering of the map data 194. It will be understood that information can be measured at any appropriate location within the patient 26 to assist in identifying a specific location within the patient 26. For example, pressure and an electrogram can be measured in any circulatory portion, pulmonary portion, or organ of the patient 26 with an instrument. The measurement of a characteristic can also be done manually or automatically at any selected rate, such as once per heart beat. The discussion herein relating to measuring information within the heart 80 of the patient 26 is understood simply to be an example for the discussion herein.

With reference to FIG. 26A, the mapping catheter 100 can be positioned in the patient 26 at various locations. As illustrated in FIG. 26B, various portions of the heart 80 can be identified in the anatomy of the patient 26. For example, a superior vena cava SVC, right atrium RA, inferior vena cava IVC, right ventricle RV, a pulmonary artery PA, a tricuspid valve TCV, and a pulmonic value PV. Each of the portions of the heart 80 can be accessed with the mapping catheter 100.

As particularly illustrated in FIG. 26A, the mapping catheter 100 can be connected with the PSU I/O 42. In addition, various patient monitoring systems can include an electrocardiogram (ECG) 570. The ECG 570 can be connected with the patient 26 using various electrodes exemplary illustrated as electrodes 572*a-c*. Each of the ECG electrodes 572*a-c* can be connected with the ECG 570. The ECG 570 and the PSU 40, in turn, can be interconnected or incorporated. By interconnecting the ECG 570 and the PSU 40, information from the ECG 570 can be used by the PSU 40. As one skilled in the art will understand, a cardiac rhythm or cycle can be measured with the ECG 570 and selected portions of the cardiac cycle can be determined. Various phases of cardiac cycle can be identified automatically (e.g. by a processor executing instructions and receiving a signal from the ECG 570) or by one skilled in the art viewing a graph produced from the ECG 570. Various portions of the cardiac cycle can include a P-wave, a R-wave, T-wave, and other specific features of the cardiac electrical cycle. The cardiac cycle can also be used to identify or diagnose conditions of the patient 26.

The ECG electrodes 572*a-c* of the ECG 570 can measure or detect electrical signals from the outside of the patient's body 26, such as a voltage, which can be measured by the ECG 570. As discussed above, the electrodes of the mapping catheter 100, such as the ring and tip electrodes 108, 110 can also be used to measure electrical signals of the patient 26. Measuring or sensing electrical activity of the patient 26 by the mapping catheter 100 can be done in addition or alternatively to acquiring the mapping data 194. Electrical signals from electrodes in the body, especially from within the heart, are called electrograms (EGM). The electrodes of the mapping catheter 100 can be used to measure EGMS to be used by the PSU 40. As discussed further herein, a comparison of a measurement of an EGM with the mapping catheter 100 and a measurement with the ECG 570 can be used to assist in identifying locations of the mapping catheter 100. For example, as one skilled in the art will understand, various portions of a recorded ECG, such as the P-wave, can be matched or aligned in time to measurements or deflections with EGM's measured with the mapping catheter 100 to determine the location of the mapping catheter 100. Also, the balloon 102 or other appropriate sensors can be used to measure pulsative pressure at a selected location of the mapping catheter 100, such as the substantially near the distal end.

Figure 27A:
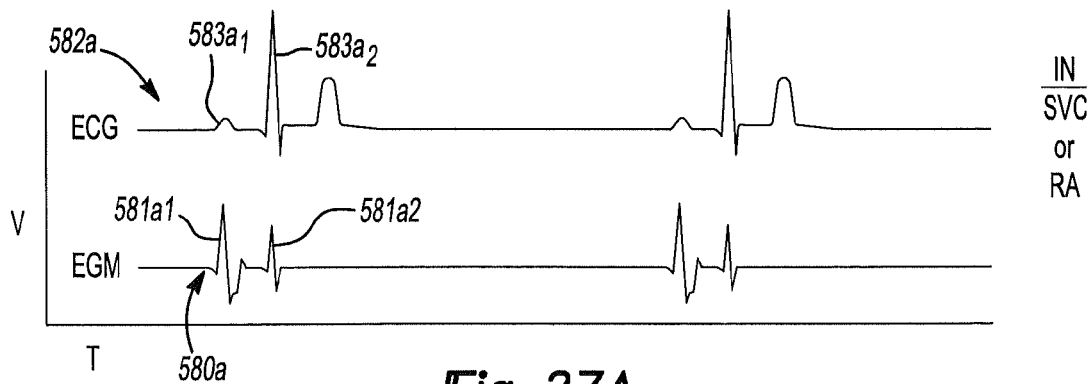

The mapping catheter 100 can be inserted into the patient 26 through an introducer, as discussed above, into an axillary vein that extends into the SVC, as illustrated in FIG. 26B. The mapping catheter 100 can generally be understood to substantially always or selectively pass through the SVC at least in an initial state when introduced through an axillary vein. The mapping catheter 100 may move into the heart through the IVC if it is initially inserted into a leg of the patient 26, however, when the mapping catheter 100 is low in the SVC or the RA, an electrical measurement or deflection measured with the mapping catheter 100 can measure an electrogram (EGM) as illustrated in FIG. 27A. The voltage (V) can be plotted over time (T) in a line 580$a$. The EGM line 580$a$ can include a large spike or deflection 581$a_1$ which represents a spike in voltage. The timing of the spike 581$a_1$ can be compared to the timing of a portion of the ECG line 582$a$. For example, the position of the spike 581$a_1$ of the EGM line 580$a$ can be compared to the P-Wave spike 583$a_1$. When the spike 581$a_1$ of the EGM 580$a$ occurs coincident in time or before the P-Wave spike 583$a_1$ of the ECG 582$a$, it is an indication that the electrode measuring the EGM is in the SVC or RA. A smaller spike 581$a_2$ may also be measured in the EGM line 580$a$ which is coincident with the R-wave 583$a_2$ even when the EGM is measured in the SVC or RA. The smaller spike 581$a_2$ can represent a ventricular activity.

Figure 27B:
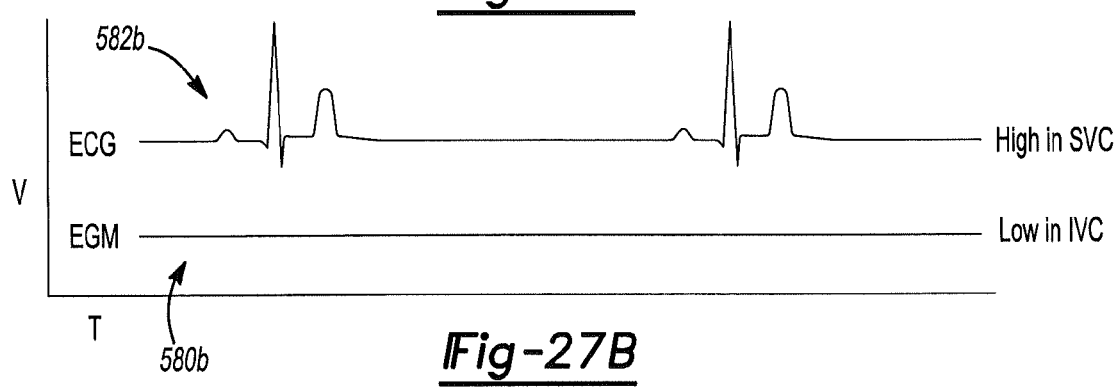

With reference to FIG. 27B, an EGM line 580$b$ can be plotted as voltage as a function of time relative to the ECG 582$b$, as similarly illustrated in FIG. 27A. Relatively little or not deflection or measured voltage is illustrated. When relatively no or little voltage is measured by an electrode in an EGM it is an indication that the electrode measuring the EGM is either very high in the SVC or very low in the IVC. That is, if the electrode is in the SVC or the IVC it is a relatively large distance from the heart, such as an atrium of the heart.

Figure 27C:
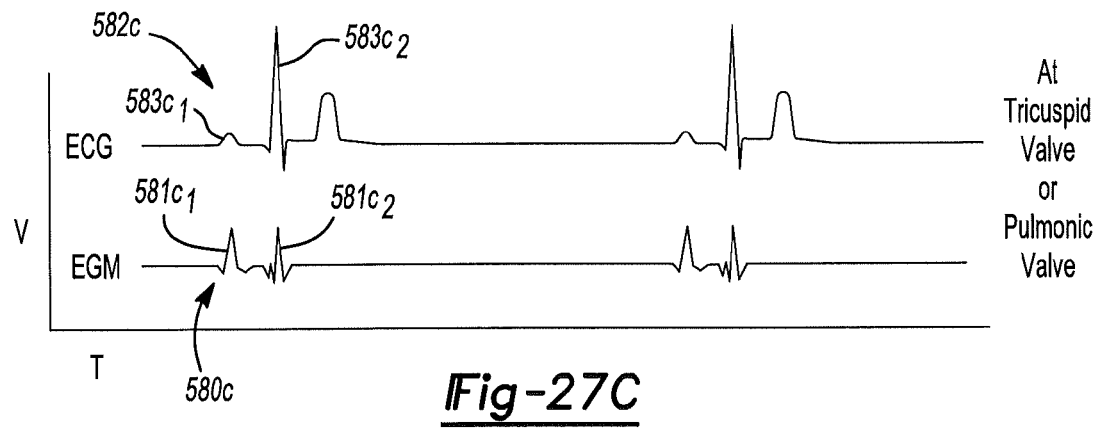

With reference to FIG. 27C, an EGM measuring voltage represented as a function over time can be displayed as line 580$c$. The EGM can include two spikes or large deflections 581$c_1$ and 581$c_2$. An ECG line 582$c$ can include or illustrate two voltage measurements or deflections representing a P-Wave 583$c_1$ and an R-Wave 583$c_2$. If the two spikes 581$c_1$ and 581$c_2$ correspond substantially in time with the P-Wave 583$c_1$, R-Wave 583$c_2$ an indication can be made that the electrode measuring the EGM is in or very near the TCV or the PV.

Figure 27D:
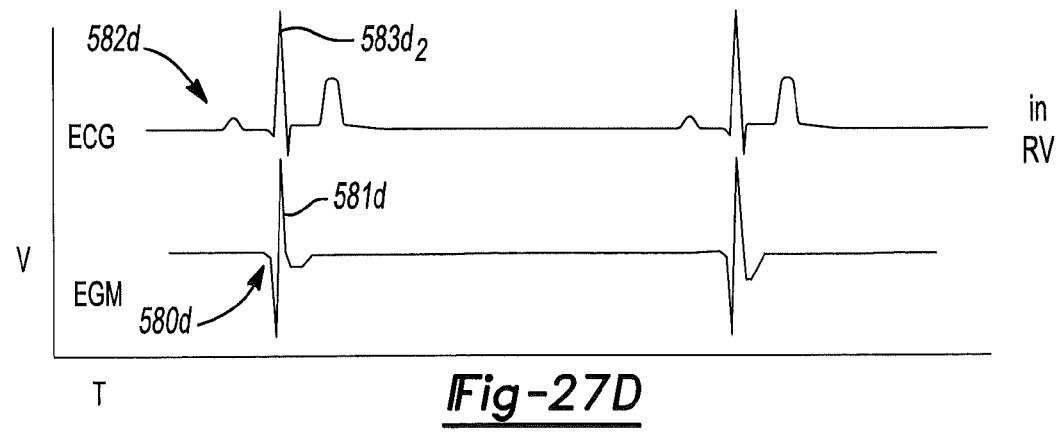

With reference to FIG. 27D, the electrode can measure the EGM and be plotted as a voltage amplitude line 580$d$ as a function of time. The EGM can include a large deflection or voltage spike 581$d$. An ECG line 581$d$ can also be plotted over the same function of time and illustrates an R-Wave 583$d_2$. If the single large spike 581$d$ of the EGM line 580$d$ and the R-Wave 583$d_2$ of the ECG 582$d$ substantially corresponds or match in time it can be an indication that the electrode measuring the EGM is in the RV.

The determination of the location of the mapping catheter 100 can be made with the assistance of information collected from various instrumentation relative to the patient 26 in addition to the mapping data 194, such as the ECG 570 or recording an EGM with the electrodes on the mapping catheter 100. The mapping data 194 that is collected with the mapping catheter 100 can be used to illustrate and identify various portions of the anatomy of the patient 26. The mapping data 194 can also be used to identify various portions of the patient 26. Nevertheless, identifying various portions of the patient 26 independent of or in addition to the mapping data 194 can be helpful to the user 22.

As illustrated in FIG. 28, the display 58 can include partitions to assist in illustrating various portions of the anatomy of the patient 26. For example, a block, square, or other appropriate geometric shape can be used to surround the map data points 198 within the SVC and the block can be identified with a label SVC'. It will be understood that the map data points or the managed points 198 can be illustrated on the display 58 in any appropriate manner to assist in identification. For example, the map data points or surface illustrated on the display 58 of the SVC can be illustrated in a different color, intensity, blinking rate, or the like. Similarly, other markings can be used to illustrate the right atrium, such as a label RA', the right ventricle, such as the label RV, pulmonary artery, such as a label PA', tricuspid valve TCV', and the pulmonic valve PV'.

With continuing reference to FIGS. 26A-28, and further reference to FIGS. 29A-29C', a processor can be used to at least assist in identifying various portions of the heart 80 of the patient 26. The processor can be that of the PSU 40 or separate therefrom and execute an algorithm or a computer program, including an algorithm, to assist in identifying, automatically or with input from the user 22, various portions of the heart 80 or other portions of the patient 26. According to various embodiments, a state machine can be used to assist in identifying various portions of the anatomy of the patient 26, such as of the heart 80.

Briefly, as listed in FIG. 29A there are only a limited number of states or locations an instrument can travel (without perforating the heart 80) from any given location in or near the heart 80. FIG. 29B illustrates a flowchart 590 that shows a method that can be used as an algorithm or in a computer program to automatically determine a state or location of an instrument based on inputs illustrated and described in FIGS. 29C and 29C'. The inputs can be automatically received by the processor, such as the processor of the PSU 40, from electrodes in the heart 80 (e.g. the electrodes 108, 110 of the mapping catheter 100) and the ECG 570. The method in the flowchart 590 can be run or processed at any given interval, such as once per heart beat. The method of the flowchart 590 can also be run or processed with no further intervention from the user 22 (i.e. substantially or completely automatically).

As understood by one skilled in the art, by passing through various natural openings of the heart 80, the mapping catheter 100 can move from one particular region to another particular region within the heart 80. From a particular region, such as the superior vena cava, the mapping catheter 100 can only move to a limited number of other anatomical regions. A position of the mapping catheter 100 can, therefore, be identified with measurements taken with the mapping catheter 100, the ECG 570, and with reference to previous states or locations of the instrument (e.g. mapping catheter 100) to identify a location of the mapping catheter 100.

As illustrated in FIG. 29A, from selected anatomical locations, as listed in the left column under "If last known location", the mapping catheter 100 can only go to specific other anatomical locations listed in the right column under "Only possible new current location(s)". As illustrated in FIG. 29A, from the SVC the mapping catheter 100 can only go to the RA. From the RA, the mapping catheter 100 can return to the SVC, or it can go to the IVC, the RV, or the CS. From the IVC, the mapping catheter 100 can only return to the RA. From the RV, the mapping catheter 100 can only return to the RA or go to the PA. From the PA, the mapping catheter 100 can only return to the RV. It will be understood that each of the current locations can be determined based upon a change or a measurement that is made. In addition, any appropriate instrument can be used, and discussion of the mapping catheter 100 is merely exemplary. Further, states can be identified for any appropriate anatomical portion, and the heart 80 is discussed here only as an example.

As illustrated in FIG. 29B, a flow chart 590 is illustrated that can be used to illustrate an algorithm using the state rules illustrated in the chart in FIG. 29A. FIGS. 29C and 29C' illustrate specific queries and information that can be used when determining the state or location of the instrument. Reference herein to the determination blocks in FIG. 29B can include the various queries and measurements illustrated in FIGS. 29C and 29C'. The queries can include position of the instrument, EGM comparison to ECG (e.g. are any EGM spikes coincident in time with ECG spikes), and pulse pressure (e.g. is a pressure measured that is greater than a zeroed or initial pressure). The state determination can be made at any appropriate frequency, such as with each beat of the heart 80, timestep, etc.

For the current discussion, it will be understood that the mapping catheter 100, begins within the SVC in block 592. The mapping catheter 100 can, however, begin in the IVC. The state changes would be the same from the IVC as well. Once it is determined that the mapping catheter 100 is in the SVC, measurements can be taken or information regarding the patient 26 and the mapping catheter 100 can be queried. Initially, the mapping catheter 100 can be determined to be in the SVC by identifying a substantially concurrent deflection or measurement of electrical activity in the patient 26 with the EGM measured by the electrode of the mapping catheter 100. If the mapping catheter is high in SVC, no EGM signal may be recorded, as illustrated in FIG. 27B. If the electrode is near the RA an EGM signal coincident with P-wave, as measured by the ECG 570, may be present as illustrated in FIG. 27A.

A query can then be made in determination block 594 of whether the lead moved to the RA. As illustrated in FIGS. 29B and 29C', the mapping catheter 100 can only move to the RA from the SVC. In the determination block 594, the determination can be based upon any appropriate information. For example, if the EGM measured with the mapping catheter 100 has a deflection that substantially coincides in time with the P-wave of the ECG 570, as illustrated in FIG. 27A, that is significantly larger than a previous measurement, then the YES routine 596 can be followed to determine that the mapping catheter is within the RA in block 598. It will be understood that the query in determination block 594 can include other measurements or considerations as well. For example, the physical location of the mapping catheter 100 can be determined to be further inferior relative to the patient 26. This indicates that the mapping catheter 100 has moved inferiorly relative to the heart 80. A further query can be whether a pulse pressure is measured. If a pulse pressure is non-existent or determined to not be present, such as less than or equal to about 1 mmHg, then the instrument can be determined to still be in the SVC. It will be understood that if either the three conditions discussed above and illustrated in block 594 in FIGS. 29C and 29C', or any other appropriate conditions, are determined to not have been measured or to have not occurred then the NO routine 600 can be followed to determine that the mapping catheter 100 remains within the SVC in block 592. It will be understood, above and herein, that the measured changes may be weighted when determining a state change.

The flowchart 590 can be further followed or analyzed to determine that the mapping catheter 100 has moved from the right atrium in block 598 to any other portion of the anatomy, as allowed by the state transition rules illustrated in FIGS. 29C and 29C'. Once it has been determined that the mapping catheter or other measuring portions is within the RA in block 598, further determinations can be made based upon measurements with the mapping catheter 100. As illustrated in the state chart in FIG. 29A, and FIG. 29C' there are four possible locations for the mapping catheter 100 to go from the RA. Accordingly, a determination block 602 can query whether the mapping catheter 100 went to the SVC, a determination block 604 can query whether the mapping catheter 100 went to the IVC, a determination block 606 can query whether the mapping catheter 100 past the tricuspid valve (TCV) went to the RV, and a determination block 608 can query whether the mapping catheter 100 went to the Cs.

The SVC, RA, and IVC can all have similar physiological characteristics, as discussed herein. They are, however, separated by inferior and superior positioning. Thus, although it can be selected to identify these three regions as one (e.g. with a single cantor on the display 58) an attempt can be made to distinguish them, as discussed below.

In the determination block 602, the YES routine 610 can be followed if there is a decrease in the EGM voltage amplitude that coincides in time with the ECG P-wave. As discussed above, if there is an increase in the amplitude of the EGM that coincides with the P-wave, the mapping catheter 100 can be determined to be in the RA in block 598. Accordingly, if there is a decrease in the EGM amplitude that is aligned with the ECG S-wave, then it can be determined that the mapping catheter 100 has transitioned back to the SVC in block 592. This determination can be further augmented by measuring a pulsative pressure with the mapping catheter 100. Generally, the pulse pressure in the SVC is weak, but can substantially match that in the RA as there is no valve or other mechanical features separating the SVC and the RA. Thus, the pulse pressure may be determined to not be present, as discussed above. In addition, as discussed above, the position of the mapping catheter 100 can be determined using the PSU 40. As illustrated in FIGS. 26A and 26B, the SVC and the RA can be substantially aligned and at a distance from one another. Accordingly, if the position of the mapping catheter is determined to have moved physically from the RA to the location previously determined to be the SVC, this can also be used to determine that the mapping catheter 100 did move to the SVC in block 602 and the YES routine 610 should be followed.

If it is determined that none of the occurrences in the determination block 602 has happened, then the NO routine 612 can be followed to the determination block 604 and a query as to whether the mapping catheter 100 has moved to the IVC can be made. The queries can include whether there has been a decrease in the EGM that coincides with the ECG P-wave or no EGM at all, as illustrated in FIG. 27B. If the decrease in the EGM that coincides the P-wave is determined or measured, it can be determined that the mapping catheter has moved to the IVC and the YES routine 614 should be followed to the determination that the mapping catheter 100 is within the IVC in block 616. A second query in determination block 604 can be if no change in pulse pressure in conjunction with a decrease in the EGM coincides with the ECG P-wave, if this is so then the mapping catheter 100 is may be within the IVC in block 616. Also, the pulse pressure may be determined to be non-existent, as discussed above. A third query can be directed to the position of the mapping catheter 100. If a decrease in amplitude of the EGM coincides with the ECG P-wave and no pulse pressure change has been measured, but the mapping catheter 100 has moved away from the SVC or has moved inferiorly within the patient 26, a determination can be made that the YES routine 614 should be followed to determine or mark the state that the mapping catheter 100 is in the IVC in block 616.

Turning briefly from the determination of the position of the mapping catheter 100 from the RA, the position of the mapping catheter from IVC in block 616 can be determined. From the IVC, the mapping catheter 100 can only be determined whether or not it has moved back to the RA in determination block 618. If it has been determined that the mapping catheter has not moved back to the RA, then the NO routine 620 can be followed and it can be determined that the mapping catheter 100 has remained in the IVC in block 616. However, a determination can be based upon a query of whether an increase in the EGM amplitude coincide with the ECG P-wave has occurred, as illustrated in FIG. 27A. Also, a query of whether the mapping catheter 100 has moved closer to the previously determined RA region. Further, a pulse pressure that is non-existent, as discussed above, can be used to determine that the instrument has not changed state. If any of the queries are true, a determination that the YES routine 622 should be followed and the mapping catheter 100 can be determined as having returned to the RA in block 598. As illustrated in FIGS. 29A and 29A', the mapping catheter 100 can only move to one other state from the IVC which is to return to the RA.

As noted above, it may be difficult to determine the state of the mapping catheter 100, or any appropriate instrument, between the SVC, the RA, and the IVC. As discussed, however, the determination rules or transition rules identified in blocks 594, 602, 604 and 618, as illustrated in FIGS. 29B, 29C, and 29C', can be used to attempt to make a determination of the state or position of the mapping catheter 100. It will be understood, however, that the position of the catheter determined with the PSU 40 can be the most indicative of the location of the mapping catheter 100 within the heart 80 as in any of the three states or locations of the SVC, the RA, and the IVC. As illustrated, the anatomy of the heart 80 is such that the superior venacava is at a location superior to the right atrium and the inferior venacava. The right atrium is inferior of the superior venacava and superior of the inferior venacava. Finally, the inferior venacava is directly inferior of the right atrium and also inferior of the superior venacava. Accordingly, if an initial starting position of the mapping catheter 100 is made, such as starting in the superior venacava, if the mapping catheter 100 is introduced through an axillary vein, then an inferior and superior position of the mapping catheter 100 can be used to assist in determining its location or state within the heart 80.

Turning back to the determination of whether the mapping catheter has left the RA 598 in FIG. 29A' and FIG. 29B, if it is determined that the mapping catheter 100 has not moved to the IVC in block 604, then the NO routine 624 can be followed to the determination block 606 to query whether the mapping catheter has moved to the RV. Initially, however, the mapping catheter would first pass the TCV, as illustrated FIG. 29C'.

Prior to the mapping catheter 100 moving into the right ventricle, the mapping catheter 100 would pass through the tricuspid valve TCV. Accordingly, when the mapping catheter 100 is in the RA, it can be determined that the mapping catheter is on the atrium side of the tricuspid valve. The mapping catheter 100 would then need to move to the ventricle side of the tricuspid valve to be in the right ventricle RV. When the mapping catheter 100 is at or near the tricuspid valve or the annulus of the tricuspid valve, a pressure pulse can be measured that is an increase over the pressure pulse measured when the mapping catheter 100 is within the RA. At the TCV the pulse pressure may be medium, which can be defined as about 5 mmHg to about 15 mmHg. Additionally, an EGM can include two spikes or amplitude deflections of voltage where one is coincident with the P-wave and the second is coincident with the R-wave, as illustrated in FIG. 27C. As discussed further herein, an EGM that is coincident with the R-wave can indicate that the mapping catheter 100 is within the RV. However, at the TCV, the EGM can measure electrical activity of both a right atrium and the right ventricle. Accordingly, the EGM measured with the mapping catheter 100 can include or have two peaks that coincide with both the R-wave and the P-wave of the ECG.

The determination of whether the mapping catheter has moved to the RV in block 606 can be based upon whether an increase in pulse pressure is measured. If an increase in pulse pressure is measured it can be determined that the mapping catheter 100 has moved from the RA to the RV. In particular, if a significantly larger pulse pressure is measured then the mapping catheter 100 is likely in the RV. The large pulse pressure can be greater than about 10 mmHg to about 15 mmHg, and include a pulse pressure greater than about 10 mmHg. In addition, the comparison of the EGM and the ECG can be made. For example, when the mapping catheter 100 moves into the right ventricle and an EGM is measured with the electrode on the mapping catheter 100, a large voltage amplitude that coincides with the R-wave of the ECG is measured, as illustrated in FIG. 27D. Accordingly, if any of the queries are positive, it can be determined to follow the YES routine 630 from the determination in block 606 to the RV block 632. If the determination is made that the mapping catheter 100 is moved from the RA to the RV by following the YES routine 630, further determinations can be made of whether the mapping catheter has moved out of the RV in block 632.

The mapping catheter 100, as illustrated in FIG. 29A, following the state of the mapping catheter 100 from the RV it can move back to the RA or further on to the PA. Turning briefly from the movement of the catheter from the RA, a first determination can be made as whether the mapping catheter has moved from the RV to the RA in determination block 634. A decrease in measured pulse pressure can be used to determine that the mapping catheter 100 has moved from the RV back to the RA in block 634 in FIGS. 29B, 29C, and 29C'. In addition, if the EGM has a large voltage amplitude that is substantially coincident with the P-wave and if the EGM no longer has a large voltage amplitude that is coincident with the R-wave, then the determination in block 634 can follow the YES routine 636 and determine the mapping catheter 100 has moved back to the RA in block 598. It will also be understood that the instrument would again traverse through the TCV to return to the RA. When going back through the TCV an EGM with two spikes coincident with the R and P wave would be measured, as would an initial pulse pressure measurement of medium from large before returning to non-existent.

If none of the determinations are made to be YES, then the NO routine 638 can be followed to determination block 640 to determine whether the mapping catheter 100 has moved from the RV to the PA. The mapping catheter 100 can move from the right ventricle to the pulmonary artery and a determination can be made in block 640. However, prior to the movement of the mapping catheter 100 from the RV to the PA, the mapping catheter 100 would pass through or be in with the pulmonic valve PV annulus. At the pulmonic valve, an EGM measured with the mapping catheter 100 can include two voltage amplitudes that are substantially coincident with the P-wave and the R-wave, as illustrated in FIG. 27C. The EGM of the heart measured with the mapping catheter at the PV can be similar to the EGM measured at the TCV. This can be so because the mapping catheter 100 is moving from the right ventricle to an area near the right atrium. In addition, a pulsative pressure transition from a higher to a lower pulse pressure can be measured with the mapping catheter 100 as it moves from the right ventricle to the pulmonary valve. The pulse pressure can be measured to be medium (e.g. about 5 mmHg to about 15 mmHg) and can be measured to be less than that in the RV, but greater than that in the RA. A second indication can be that the EGM measured with the mapping catheter 100 can be more similar to that measured in the RA, as illustrated in FIG. 27A, but may include some EGM spike coincident with the R-wave as well, as illustrated in FIG. 27C. Accordingly, if the mapping catheter 100 is determined to be previously in the right ventricle, the two queries in block 640 can be used to determine that the mapping catheter 100 has moved to the PA from the right ventricle.

If the determination is made that the mapping catheter 100 has moved from the RV to the PA, the YES routine 642 can be followed to the determination that the mapping catheter is within the PA in block 644. If the determination that the mapping catheter 100 has not moved to the PA from the RV, the NO routine 646 can be followed. Accordingly, the determination can be made that the mapping catheter has remained in the RV in block 632.

Once it is determined that the mapping catheter 100 is within the PA in block 644, a determination of whether the mapping catheter has returned to the RV can be made in block 646. In determination block 646, a query of whether an EGM measured with the mapping catheter 100 has a large deflection or amplitude that is substantially coincident with the ECG R-wave, as illustrated in FIG. 27D, is made. Additionally, a measurement of an increase in pulse pressure can be queried to determine that the mapping catheter 100 has again returned to the RV from the PA. As discussed above, the pulse pressure in the RV is large, as defined above, and is greater than that in the PA and this increase in pulse pressure can be used to determine that the mapping catheter 100 has returned to the RV. If the determination is made that the mapping catheter 100 has moved from the PA to the RV, then the YES routine 648 can be followed to the RV block 632. If it is determined that the mapping catheter 100 has not moved from the PA to the RV, then the NO routine 650 can be followed to determine that the mapping catheter remains in the PA in block 644.

Returning again to a state change or movement of the mapping catheter 100 from the RA in block 598, a determination can be made as to whether the mapping catheter 100 has moved from the RA to the CS in the determination block 608 in FIGS. 29B and 29C. The mapping catheter 100 can be used to measure a pulse pressure, as discussed above. From the RA, if a slight or small pulse pressure increase is measured, it can be determined that the mapping catheter 100 has moved into at the coronary sinus annulus. The slight or small pulse pressure can be about 1 mmHg to about 5 mmHg. According to one theory, a physical compression of the balloon 102 of the mapping catheter 100 can be the reason for the slight pulse pressure measurement. The heart, when contracting, can physically squeeze the balloon 102 when the balloon 102 is within the coronary sinus. Accordingly, the small pulse pressure increase measured when the mapping catheter 100 is otherwise in the RA, can be used to determine that the mapping catheter 100 has moved to the CS. Also, as illustrated in FIG. 26B, the CS is medial of the RA. Thus, if the position of the instrument is determined to be medial of the RA or to have moved in a medial direction it can be an indication that the instrument has moved to the CS. A temperature measurement can also be made to determine the location of position of the instrument in the CS. As discussed below the temperature of the blood in and near the CS can be about 0.1 degrees warmer than the other blood. Further, the direction of flow of blood at the CS will be away from the CS. As discussed herein, flow direction can be determined and this can also be used to determine a state or location of the instrument and the location of the CS. If it is determined that none of the above noted measurements or changes occurred, then the NO routine 660 can be followed to determine that the mapping catheter remains in the RA in block 598. If the determination block 608 is made that the mapping catheter 100 has moved to the CS, then the YES routine 662 can be followed to the determination of the mapping catheter 100 is within the CS in block 664.

A determination block can then be used to determine whether the mapping catheter has moved from the CS in block 664 to the RA in block 598 or has remained in the CS in block 664. In the determination block 666, the determination of whether the mapping catheter 100 has moved to the RA can be based upon querying if a slight increase in pulse pressure has been removed. As discussed above, a slight increase in pulse pressure can be used to determine that the mapping catheter 100 has moved into the CS. Accordingly, if the slight pulse pressure increase is not measured any longer, it can be determined that the mapping catheter 100 has moved back to the RA and out of the CS. Also, the instrument would move lateral from the CS, in a direction opposite the medial direction discussed above. If the determination is made that the mapping catheter 100 has not moved to the RA, then the NO routine 668 can be followed to determine that the mapping catheter 100 has remained in the CS in block 664. If the determination is made, however, that the query is positive, the YES routine 670 can be followed to make the determination that the mapping catheter 100 is in the RA in block 598.

The flow chart 590 can be used to determine a state or position of the mapping catheter 100 as discussed above. A signal to make a determination can be based upon manual input, a change in a measurement, or a time step or time differential. For example, the user 22 can move the mapping catheter 100 and an initial a determination of whether the mapping catheter 100 is within the patient 26, such as within the heart 80, can be made.

The measurements for the determinations discussed above can be made or collected over a selected period of time, such as one, two, or more complete cycles of the cardiac cycle of the heart 80. Also, the timing can be based upon position sampling timing, such as one or more position samples. Position sampling can be at a rate of one per about 80 milliseconds (about 12.5 per second). As discussed above, the ECG 570 can be connected with the patient 26. The ECG 570 is also connected with the PSU 40. Accordingly, a portion or number of cardiac cycles can be determined based upon ECG 570. In addition, a processor in the ECG 570 can identify the various waves of the ECG, such as the P-wave, the T-wave, or the R-wave. Any other appropriate processor can also be used for the wave determinations. Further, the wave determinations can be made manually. It will be understood, therefore, that the position of the mapping catheter 100 can be based upon various measurements taken of the patient 26, such as with the ECG 570, and include the state identifications illustrated in FIG. 29A and other appropriate information as discussed above.

The location or state of the various portions of the map data on the display can be updated or corrected. That is that the indication of the particular state on the display can be corrected to redisplayed at a later timestep. As illustrated in FIG. 28, therefore, the state indications need not be static.

Further, the flowchart 590 and the related queries are made based on assumptions that the heart 80 of the patient 26 is in normal or sinus rhythm. The ECG, pressure, and other measurements of a sick patient may be different. Different state information, however, can be used to determine a state of the instrument is included in the various query blocks. Also, further inquiries can be added, such as change in diastolic pressure, rate of change of pulse pressure, mean diastolic pressure, and other measurements can be made and queried to determine a state of the instrument. Accordingly, those discussed above are exemplary of queries that can be made when determining a state or location of the instrument.

In addition to the various measurements taken with the mapping catheter 100 that can be compared to the ECG timing, as discussed above, it will be understood that the mapping catheter 100 is tracked for position within the patient 26. Accordingly, as discussed above, the inferior and superior location of the mapping catheter 100 can be used to assist in distinguishing the SVC, the RA, and the IVC from each other. Additionally, medial and lateral positions can be used to assist in determining the position of the pulmonary valve and artery from the tricuspid valve and the right atrium. As illustrated in FIGS. 26A and B, the PV and PA are laterally displaced from the TCV and the RA. Accordingly, the position of the mapping catheter 100 can also be used to assist in determining the position of the mapping catheter 100 and determining the state of the mapping catheter 100 within the patient 26.

Anatomical Synchronization

As illustrated in FIG. 26A, the PSU 40 and the ECG 570 can be connected with the patient 26. The ECG 570, or any appropriate physiological monitoring system, can be used to measure patient physiological functions. This information can be used to synchronize the position determinations with physiological cycles of patient functions. The position determinations can be those made using the electrodes on the mapping catheter 100 to determine a position of the mapping catheter 100 within the patient 26. In addition, the reference electrodes 52*a*, 52*b* can be used to determine a reference impedance $Z52a52b$ which can be used to determined a position of the reference electrodes 52*a*, 52*b* relative to the patient 26 and the other electrode patches 46*a*-50*b*.

The ECG 570 can be used to identify the cardiac cycle of the patient 26 and determine in which portion of the cardiac cycle the patient 26 presently exists. The reference patches 52*a*, 52*b* can be used to determine both cardiac and respiratory cycles of the patient 26 by measuring an impedance between the two reference patches 52*a*, 52*b*, positioned on a dorsal and anterior side of the patient 26.

According to one theory, the reference impedance $Z52a52b$ determined between the two reference patches 52*a*, 52*b* changes as the heart 80, for example the ventricles, fill and then empty of blood. As is understood by one skilled in the art, significant amounts of blood flow to the ventricles and then to the lungs and systemic circulation via the aorta. The blood of the patient 26 is highly conductive relative to surrounding tissues and other body constituents, such as skeletal muscle, bone and air. So, as the heart 80 beats and the blood travels in and out of the heart 80, the conductance of the portion of the patient 26 in the vicinity of the heart 80 changes as a function of time due to the shift in position of the bolus of blood being pumped. Accordingly, the change in the reference impedance $Z52a52b$ can be used to determine or follow the cardiac cycle.

In addition to the heart 80 pumping blood, the pressure in the chest and thorax region can alter based on the respiratory cycle of the patient 26. As lungs of the patient 26 fill during inhalation the chest expands and the relative negative pressure within the thorax decreases. During exhalation, for example when the lungs are at peak exhalation, the relative negative pressure in the thorax helps draw blood into the ventricles of the heart 80. When the lungs are at peak inhalation, the negative pressure is less and filling of the heart is less. Also, as the lungs expand and contract, the heart position changes relative to other anatomical structures, such as the xiphoid process. Accordingly, the volume of blood within the heart 80, and the related determined impedance, during peak inhalation will have a different amount of blood than during peak exhalation.

As discussed above, the reference patches 52*a*, 52*b* can be placed over the xiphoid process and directly dorsal to the xiphoid process. As discussed above, the heart 80 can moved during inhalation and exhalation. Accordingly, a difference in determined reference impedance $Z52a52b$ can also be used to determine the position of the heart 80 and the respiratory cycle. Moreover, because the reference impedance $Z52a52b$ is based on both respiratory and cardiac cycles, the signal of the reference impedance $Z52a52b$ can be filtered to determine information about both cycles.

The PSU 40 can, therefore, be used alone or with other physiology monitoring systems to determine both cardiac and respiratory cycles of the patient using the impedance and/or information regarding position of the reference patches 52*a*, 52*b* and the ECG 570. The portion of the physiology cycles can be used to classify the mapping data 194. For example, a first map data point can be determined to be within a filling (e.g. diastole) portion of the right ventricle cycle. A second map data point can be classified to be within an emptying (e.g. systole) portion of the right ventricle cardiac cycle. Similarly, the map data 194 can be classified to be within an exhalation or an inhalation portion of the respiratory cycle. Accordingly, each of the map data 194 can be classified into an appropriate or a selected group based upon the cardiac cycle and the respiratory cycle.

The physiological cycles, however, need not only be split into two groups or viewed separately. For example, map data can be collected and classified as (1) in systole and during exhalation, (2) in systole during inhalation, (3) in diastole during exhalation, and (4) in diastole during inhalation. Other classifications can also be provided or selected to further segment the map data during collection. The map data, however, need not be classified, but can be classified in any appropriate number of classes for reasons or purposes discussed herein.

With reference to FIG. 30A, once an appropriate data set of the map data 194 is collected, based upon a selected class which can be regarding a portion of a selected cycle, such as the diastole portion of the cardiac cycle of the right ventricle, a diastole surface rendering 700 can be displayed on the display 58. On or relative to the surface 700 the user 22 or the PSU 40 can then identify a first point 702, a second point 704, and a dimension 706 between the first and second points, 702, 704 for analysis. The points on the surface 702, 704 can be used for analysis of the heart 80, such as volume change, etc.

With reference to FIG. 30B, an appropriate data set regarding a systole state of the right ventricle can also be collected and a surface 720, illustrating a systole state of the heart 80 on the display 58 can also be rendered. Corresponding points 702' and 704' can be determined on the systole surface 720. A dimension 722 between the two points 702' and 704' can also be determined for analysis. The points on the surface 702', 704' can be used for analysis of the heart 80, such as volume change, etc.

Accordingly, the map data 194, illustrated as the map data points 198 on the display 58, or as the surfaces 700 and 720 on the display 58 can be selected by the user 22. The user can then view the various surfaces or models of the heart 80 to identify lead implants positions, anatomical functioning, and other selected information. It will also be understood that the data used to render the surfaces can also be collected in different states of the respiratory cycle. Accordingly, the surfaces displayed can include different states of the respiratory cycle. The various surfaces, such as the systole and diastole state surfaces, can illustrate differences in the heart 80 based upon a state of the heart 80 in the cardiac cycle. This information can be used by the user 22 or any appropriate system to diagnose diseases of the heart 80, implant lead locations (e.g. for optimum stimulation), etc.

As one skilled in the art understands, a position in three-dimensional space or patient space, of a portion of the heart, such as an interior wall position of the right ventricle, is based upon at least the cardiac rhythm and respiration of the patient 26. Accordingly, the map data 194 that is collected with the mapping catheter 100 can be identified or classified to classify the map data relating to the position of the various portions being mapped, such as the wall of the heart 80. This can allow for a substantially precise anatomical map of the heart 80 at the various contraction, relaxation, and respiration positions.

Classifying, saving, and rendering only or substantially only similarly classified map data can also allow for a plurality of surfaces to be determined, rendered, and displayed on the display 58. According to various embodiments, the technique of assigning map data to different classes can be used to provide at least a 1) stable display of the heart, 2) video or motion "image" synchronized to the patient's 26 physiology, or 3) slow motion video or motion image without reference to any current patient 26 physiology. The motion of the heart 80 and the various instruments, such as the mapping catheter 100 within the heart 80, imparts information utilized by the user 22. The motion can be generated by display successive images of map data that are classified as successive parts of a respective cycle or multiple cycles. The resulting map data points or surface can be used to illustrated a natural and true position and movement of the heart 80. It will be understood, however, that map data can be collected for any appropriate region of the patient 26 and the heart 80 is merely an example. Nevertheless, the image on the display 54 need not be a static image that relates only to an average of maximum distance within the heart 80, but can be a moving image based on a successive display of multiple renderings of the map data classified from the patient 26.

As one example, a stable image of the heart can be rendered from data of a particular or single selected map data class (e.g. diastole and expiration). Such an image can impart great understanding and confidence by the user 22. Rendering of the instruments, such as the electrodes 108,110 of the mapping catheter 100, can also be presented with the same classification so the representation of physical position is in the same context as the rendered image of the heart chambers/vessels.

A motion video, such as one generated by sequential morphing of stable images synchronized to the patient's 26 physiology can mimic a position of the heart 80 and motion as it occurred when the map data were gathered, classified, and stored. While particular care can be taken during changes in rhythm, such as sighs or extrasystolic cardiac activity, such a motion video allows rendering of the instruments, such as the mapping catheter 100, to be essentially in real-time. That is, localization of electrodes or other sensors can be drawn to the display 54 as they are received and super-imposed over a moving background. This can be compared to the stable image of the heart 80 which can be drawn from the same classification of the map data. Displaying motion of the instrument super-imposed on a stable or fixed image may be confusing; that is, it may show the lead moving and penetrating a wall of the heart 80 when, in reality, the heart 80 is in motion, but not shown as such on the display 54. Playing a video as a background image on which the instrument position is displayed assumes the heart position and motion remain the same as when the data were acquired. While this may not be precisely true, it can provide information to the user 22 not seen or provided with a stable image based on unclassified data or only a single class of map data.

A slow motion video of the heart 80 and instruments could help the user 22 understand the data being presented. This could be a replay of the saved map data so the relative positions of the heart and instruments can be easily seen. Such video could be selected from recently saved map data and replayed during an implantation procedure. In addition, the map data can be replayed for training, review, or planning purposes.

As a further specific example, map data can be gathered for any appropriate portions of the cardiac cycle and respiratory cycle. The different classified data can then be displayed on the display 58, as illustrated in FIGS. 30A and 30B, to illustrate the surface rendering 700, 720 of the heart 80 at different cardiac cycle positions. A selected number, such as 2, 4, 16, or any appropriate number, of renderings can then be displayed in succession or synchronized with the ECG 570 or displacement between two electrodes such as xiphoid and back. This can allow the display on the display 58 to substantially mimic the cardiac cycle and respiration cycle of the patient 26.

The surfaces 700, 720, can be based on rendering the map data 194 collected with the mapping catheter 100. Image data, collected with an imaging system, external to the patient 26 or separate from the PSU 40 and the mapping catheter 100, need not be required to generate the surfaces 700, 720, illustrated in FIGS. 30A and 30B. Nevertheless, the display on display 58 can be used to display a substantially correct anatomical position of the heart 80 based on classifying the map data 194 to the cycle of the patient, such as the cardiac and respiration cycle. Thus, the surface rendering on the display 58 can be generated to show sequential motion, and other appropriate information to the user 22 without requiring an external imaging system to continuously image the patient 26.

Bi-Polar and Uni-Polar Measurements

As previously discussed, the mapping catheter 100 can include two electrodes, such as the tip electrode and the ring electrode 108, 110. When both electrodes are exposed bipolar measurements can be made and when only one is exposed, unipolar measurements can be made. The two electrodes of the mapping catheter 100 can be delivered to the patient 26 in a specific location through a sheath or other sleeve portion. When the two electrodes are within the sheath, either no electrodes or only the tip electrode 108 is exposed to fluids that allow the electrode to measure an impedance or voltage within the patient 26. When both of the electrodes, including the tip and ring electrodes 108, 110, are exposed then both electrodes can measure an impedance within the patient. In addition, other instruments positioned within the patient 26 can include one or more electrodes to measure an impedance. The electrodes 108, 110 of the mapping catheter 100 can also be used to measure electrical activity within the patient 26, such as measuring electrical activity in the heart 80 of the patient 26 to generate an electrocardiogram of the patient 26.

Because the number of electrodes exposed to the anatomy of the patient 26 can differ over time, the PSU 40, including the PSU I/O 42, can determine whether the system PSU 40 should measure, such as the EGM, in a unipolar or bipolar manner. When two electrodes are exposed, the PSU 40 can measure in the bipolar manner, such as an EGM or an impedance of the patient 26. When only one of the two electrodes is exposed, then the system PSU 40 can measure in a unipolar manner. Accordingly, the PSU 40 and other appropriate systems can measure in a uni-polar or bi-polar manner (e.g. measuring with one electrode or two or more electrodes) and can be switched, manually or automatically, between unipolar and bi-polar.

The PSU 40 can switch between a unipolar and bipolar manner based upon various inputs. For example, the user 22 can input when the lead or the mapping catheter 100 is being pushed past the end of a sheath or other isolating covering. Accordingly, a substantially manual input can be used to instruct the system PSU 40 to measure in a unipolar or bipolar manner.

The PSU 40 can substantially automatically determine whether to measure either unipolar or bipolar, depending upon the number of electrodes exposed. The PSU 40 can determine that two electrodes are exposed when two electrodes measure impedance and/or EGM at a time step that are substantially identical, when at a substantially immediate time step the EGM and/or impedance was substantially different. In this manner, when one electrode is exposed to the body fluids of the patient 26, an impedance can be measured while the other substantially insulated electrode is not measuring an impedance within the patient 26. At a second time step, when the second electrode is exposed to the patient 26, it can measure the impedance of the patient 26. In addition, when both electrodes of the mapping catheter 100 are exposed, the impedance measured by both should substantially match. Other appropriate methods can be used to determine when electrodes are exposed or pushed past the end of the sheath, such as those disclosed in U.S. patent application Ser. No. 12/421,375 incorporated herein by reference.

When switching between measuring the EGM or the impedance in the patient either in a bipolar or unipolar manner, differences or similarities can be measured. For example, the impedance of the patient measured with the first and second electrodes, such as the tip electrode 108 and the ring electrode 110 of the mapping catheter 100, that are near each other then the impedance measured of the patient 26 should be substantially similar. Therefore, a confidence measure can be obtained when an appropriate measurement is taken. In addition, an EGM measurement can be changed between a bipolar and unipolar measurement such as by determining when an electrode is withdrawn. For example, when an electrode is insulated or withdrawn into a catheter, the EGM signal disappears.

Flow Direction

Direction of flow of material within the patient 26 can be determined with the PSU 40, according to various embodiments, as illustrated in FIGS. 31A-34B. In addition, the flow of material within the patient 26 can be displayed on the display 58, also according to various embodiments. The direction of flow of material within the patient 26 can be used for various purposes, such as determining a location of the coronary sinus, other openings, flow of material within a vessel or vasculature, or other information. The direction of flow can be used to identify the coronary sinus ostium (CS OS) within the heart 80. The identification of the CS OS can be used to assist in identifying locations of appropriate implantation of a lead, such as within the left portion of the heart 80, and can be used to identify unexpected flow direction associated with congenital abnormalities of the circulation. Thus, flow direction can be used to identify or diagnose various illnesses.

With reference to FIGS. 31A and 31B, a mapping catheter 100 can be positioned within the patient 26, such as within the heart 80. As discussed above, the mapping catheter 100 includes electrodes that can measure an impedance within the patient 26 for position determination with the PSU 40. The direction of flow or movement within the patient 26, such as within the heart 80, can be calculated based upon the movement of the electrodes 108, 110 of the mapping catheter over time. The electrodes 108, 110 can move while holding steady or at a static location a portion of the mapping catheter 100, such as a proximal end of the mapping catheter 100. Thus, movement of the electrodes 108, 110 can be substantially or only because of flow of a material at a distal end of the mapping catheter 100.

For example, as illustrated in FIG. 31A, at a first time, a tip electrode point 108', representing a position of the tip electrode 108, can be determined relative to a point 740 on a portion of the surface 281. A distance 742 can be calculated between the two points 740, 108'. At a second time later than the first, such as at a fraction of a second, a complete second, or any appropriate portion of time, a second position or point 108" of the tip electrode 108 can be determined and a second distance 744 relative to the same point 740 on the surface 281 can be calculated.

The difference between the two distances 742 and 744 can be used to calculate an amount of flow or force of flow. The direction of movement of the tip electrode 108 can also be determined based upon the two points 108', 108" to determine a direction of flow relative to the point 740 on the surface 281. Accordingly, a direction of flow and an indication of force of flow can be calculated based upon the change in position of the mapping catheter 100 over time.

The balloon 102 can be used to assist in determining the direction of flow by causing resistance within the flow within the patient 26. As discussed above, the balloon 102 can be inflated once positioned within the patient 26 and the balloon 102 can have a cross section greater than that of the remaining portions of the mapping catheter 100. The balloon 102, with its large area, can cause drag relative to the electrodes 108, 110 of the mapping catheter 100 to assist in a flow direction and force determination. The flow of material, such as blood, can drag the balloon 102 to determine motion.

Flow direction within the patient 26 can also be determined by a physical difference between two points. Because the PSU 40 allows for a determination of a three dimensional position of an electrode positioned within the patient 26, based upon the measured impedance or voltage within the patient 26. Accordingly, if two electrodes are positioned relative to one another and a flow is allowed to act on at least one (i.e. a moveable electrode) of the two electrodes, a direction of movement of the moveable electrode relative to the substantially more stationery electrode can be determined. The two electrodes on the mapping catheter 100 can be selected to move relative to one another to assist in determining flow direction. Nevertheless, other devices or an augmented mapping catheter 100 can be provided.

For example, as illustrated in FIG. 32 a mapping catheter 750 is illustrated. The mapping catheter 750 can be similar to the mapping catheter 100, discussed above, and can include more than one electrode or the balloon 102, like the mapping catheter 100. The mapping catheter 750, however, is discussed as including only a single catheter electrode 752 for simplicity of the current discussion. The mapping catheter 750 can include a sheath or cannulated tube 754 that can be positioned within the patient 26. Passing through an inner cannula or passage 756 can be a second flexible electrode body 760. The flexible electrode body 760 can include an electrode tip 762 and a length that can be insulated with a covering 764. The electrode tip 762 can be used to measure an impedance or voltage within the patient 26, similar to the electrodes discussed above, such as the tip and ring electrodes 108, 110 of the mapping catheter 100.

The catheter electrode 752 can be used to measure a first position and the flexible member electrode 762 can be used to measure a second position. The flexible member electrode 762 can be allowed to flex and move relative to the catheter electrode 752 based upon a flow of material within the patient 26. To allow the flexible member electrode 762 to move relative to the catheter electrode 752, the flexible member 760 can be formed of any appropriate material that is flexible enough to move when influenced by a flow of material within the patient relative to the catheter electrode 752. Also, the outer portion 750, particularly a distal end thereof, can be held at a static location within the heart other appropriate volume during flow or motion determination. According to various embodiments, the flexible member 762 can be formed of a substantially small diameter wire that can be formed of any appropriate material, such as gold or copper. In addition, it will be understood that the dimensions of the mapping catheter 750 and the flexible member 760 are illustrated simply for clarity and can be provided in any appropriate dimensions. For example, the flexible member 760 can have an external diameter that substantially fills an internal diameter of the cannula 756.

As illustrated in FIG. 33, a mapping catheter 750a can include an internal cannula 756a that has an interior diameter that substantially matches an external diameter of the flexible member 760. Accordingly, the flexible member 760 can be held substantially fixed relative to a catheter electrode 752a save for forces acting upon the portion of the flexible member 760 extending from a distal end 770 of the mapping catheter 750a. Accordingly, substantially only flow motion will be indicated based upon a position of the flexible member electrode 762 relative to the catheter electrode 752a.

With reference to FIGS. 34A and 34B, the mapping catheter 750a can be positioned within the patient 26, such as within the right atrium of the heart 80. Once the mapping catheter 750a is positioned within the heart 80 (or at any appropriate time), the flexible member 760 can be extended a selected distance out of the catheter body 754a. Once the flexible member 760 is extended out of the catheter body 754a, such as a selected distance from the distal end 770, flow within the heart 80 can cause the flexible member 760 to bend or move. The flexible member electrode 762, being positioned substantially at a distal end or at any appropriate position on the flexible member 760 that is able to move relative to the distal end 770 of the catheter body 754a, can move within the flow. Once the force of the flow acts upon the flexible member 760 to move the flexible member electrode 762, the PSU 40 can determine the position of both the catheter electrode 752a and the flexible member electrode 762a.

As illustrated on the display 58 in FIG. 34B, a mapping catheter electrode icon 752a' can be displayed on the display 58 relative to the map point 194, such as the surface 281. It will be understood, however, that determining a flow direction does not necessarily require other map data 194 to be illustrated. The surface 281 is displayed for illustration purposes and this discussion as an example.

The PSU 40 can also illustrate a position of the flexible member electrode 762 as flexible member electrode icon 762'. The user 22 can then view on the display 58 the position between the mapping catheter electrode icon 752a and the flexible member electrode icon 762 to view a direction of flow. In addition, the PSU 40 can determine a direction of flow based upon the difference in position of the determined positions of the electrodes of the mapping catheter 752 and the flexible member 762. The direction of flow can be illustrated as an icon, such as an arrow icon 780. The arrow icon 780 can illustrate the direction of flow in a selected area. For example, flow of blood within the heart 80 may be away from the CS OS, but blood may flow in any various directions at other locations within the heart 80. It will be understood, that the direction of flow may also change based upon the position within the patient 26. Accordingly, one or more flow direction icons, such as arrows 782, 784, and 786 can be displayed on the display 58.

According to various embodiments, the display 58 can include any and all of the data discussed above. In addition, the display 58 can be manipulated according to any method, as discussed above. Accordingly, the rocking can be instituted to illustrate the substantially three dimensional nature of the varying positions for the flow direction as illustrated on the display in FIG. 34B. This can allow the user 22 to illustrate a two dimensional or three dimensional view of the mapping data and the flow direction determination. In addition, the position of the various electrodes, such as the mapping catheter electrode 752a and the flexible member electrode 762, can be done in substantially real time. This allows the display 58 to be updated in real time to illustrate the change in flow over time. The display 58 can also be used to display a plurality of flow directions in a single location over time. Accordingly, the user 22 can view a turbulent area and understand the turbulence in the single area based upon a plurality of flow direction measurements. Turbulence may be due to valvular dysfunction resulting in regurgitate flow.

Additionally, the force of flow can be determined based upon the amount of bending of the flexible member 760. The amount of bending can be based upon the known dimension of the flexible member 760 extended past the distal end 770 of the mapping catheter body 754a and the position of the flexible member electrode 762 relative to the mapping catheter electrode 752a. The further the flexible member electrode 762 is radially displaced from the mapping catheter electrode 752a, the greater the force of flow within a particular area can be inferred or determined.

In light of the above, the PSU 40 can be used to identify various points and/or locations and illustrate the various points on the display 58. By identifying a plurality of points and plotting or determining a location of each of the points relative to one another in a three dimensional space, a map is generated. As discussed above, the map can be illustrated on the display 58 as the map data points 198 or the surface 281. In addition, the PSU 40 can be used to identify and illustrate the locations of various landmarks or features within the patient 26, as discussed above.

Sheathing Detection

As discussed above, an electrode positioned within the patient 26 can be used to sense or measure a voltage and/or determine an impedance. The voltage or impedance can be used to determine a position of the electrode within the patient 26. The position of the electrode within the patient 26 can be illustrated on the display 58 and a map can be generated from the position data.

According to various embodiments, however, as illustrated in FIG. 3, the mapping catheter 100 can be introduced into the patient 26 through a sheath 104. The sheath 104 can substantially insulate the electrodes on the mapping catheter 100 such that the electrode does not properly sense the voltage within the patient 26, therefore altering the determined position of the catheter and electrode within the patient. Similarly, an electrode that is a retractable electrode can be retracted into an insulative housing thereby substantially rendering immeasurable any voltage and impedance determination.

Accordingly, it can be selected to include an algorithm or method that determines whether the electrode used for mapping or position determination is properly exposed within the patient 26. According to various embodiments, the PSU 40 can identify whether an electrode is sheathed or unsheathed. As discussed herein, a sheathed electrode can be any electrode that is covered by an insulator, such as a sheath for delivering the catheter or introducing the catheter. An unsheathed electrode can be any electrode that is exposed to a conductive medium within the patient 26 for properly sensing a voltage to determine an impedance.

With reference to FIG. 35, the display 58 can illustrate whether the catheter (e.g. an electrode moveable relative to the catheter), lead electrode that is retractable into a sheath, or other position element has been determined to be sheathed or unsheathed. As illustrated in screen 58a, a representation of a portion of the mapping catheter 100 is illustrated. The mapping catheter 100 can be illustrated as including a sheath portion 108 and an extendable electrode portion 102x. It will be understood that the icons 108 and 102x can be provided or illustrated in any appropriate color or grey scale. For example, as illustrated in FIG. 35, the sheath icon 108 can be shown heavier bordered or in a different color than the electrode icon 102x, which can be illustrated substantially empty or only as an outline. In addition, the map data points 198 can also be displayed relative to the icons 108 and 102x. If it is determined, as discussed herein, that the mapping catheter 100 is sheathed, an alternative display 58a' can display a sheathed icon 102x'. The sheathed icon 102x' can differ from the electrode icon 102x in color, shading, or grey scale, and is exemplary illustrated as a hatched icon, but may also be illustrated as a bright red or orange. The sheath icon 108, however, can remain the same color, shade, etc.

It will be understood that the unsheathed icon 102x can be illustrated in a blue, green, grey, or other appropriate color. The sheathed icon 102x', however, can be illustrated in a generally understood warning color such as red, yellow, orange, or the like. Regardless of the illustration, however, the display 58 can be used to identify or communicate to the user 22 that the mapping catheter or electrode is sheathed or unsheathed. Also, auditory warnings can be given to the user in addition to visual warnings that the mapping catheter or electrode has become sheathed.

According to various embodiments, measurements of the position, either relative or absolute, of the various mapping electrodes can be used to determine whether the electrodes are sheathed or not. One or more algorithms or methods can be used to determine whether an electrode of the mapping catheter 100 is sheathed or not. Accordingly, although multiple algorithms are disclosed or discussed herein, only one or any appropriate number can be selected to be used for sheath or unsheathed detection.

It will also be understood that if an electrode is sheathed, the position information may not be reliable or valid. Accordingly, if it is determined that the mapping catheter electrode of the mapping catheter is sheathed, it can be determined that the position information based upon the sheathed mapping catheter is not used or should not be used in generating the map data points 198 or surface that is displayed on the display 58.

Any appropriate time scale can be used to determine whether information is used to generate the map on the display 58, such as one or more time steps for collecting position information of the mapping catheter 100. Generally, the position of the mapping catheter can be sampled at about one sample per 80 milliseconds. For various purposes, detection of whether a mapping catheter is sheathed or unsheathed or has become sheathed can be selected to occur within one time period or at any other appropriate time period, such as two, three, or other sampling rates. For example, if it is selected that the determination of whether the mapping catheter has become sheathed and the position information should not be used, ten samples can be used to determine whether a particular position sample is valid or not.

An algorithm for sheath detection can be based upon various observations or determinations. Observations can include at least the following five observations:

1. If an electrode travels drastically further between two successive timesteps, whether immediate or not, than it did between previous timesteps, then an electrode has likely become sheathed.

2. If two electrodes belonging to the same instrument travel in very different directions, then the instrument has likely become sheathed.

3. If two electrodes belonging to the same instrument travel in very different amounts, then the instrument has likely become sheathed.

4. If the inter-electrode spacing on an instrument expected or known to be relatively closely spaced and inflexible has become very large in an absolute sense or relative to prior samples, then the instrument has likely become sheathed.

5. If the electrode or instrument is determined to have gone past a maximum distance, especially if over a selected period of time, it has likely become sheathed.

Each of the five observations can be encoded in a computer-readable program and follow an algorithm, as discussed further herein. Any or all of the five observations can be used to determine that one or more electrodes or an entire instrument (e.g. the mapping catheter 100) is sheathed. Further, the observations can be used to compare one or more samples of position information or data as discussed further herein.

With reference to FIG. 36, a general algorithm for sheath detection is illustrated in the flowchart 800. The method can begin in Start block 802. In a determination block 804 it can be determined if the electrode is sheathed, as discussed below according to various manners. If it is determined that the electrode is unsheathed, the NO path 806 can be followed and Map data can be collected and saved in block 808. As discussed above, the collected map data can be displayed on the display 58 for various procedures and purposes. The method 800 can then end in block 810.

If it is determined that the electrode is sheathed, according to any of the various manners discussed below, then the YES path 812 can be followed. The electrode can then be marked as sheathed and position data collected while the electrode is sheathed can be disregarded in block 814. The method can then proceed to unsheathing the electrode in block 816. Once the electrode is unsheathed, map data can again be collected and saved in block 808 and the sheath detection method can end in block 810.

Any or all of the manners discussed herein can be used to determine if an electrode is sheathed. Also, the determination can be made that all or less than all of the electrodes on an instrument are sheathed. The electrode or instrument that is then marked as sheathed can be illustrated on the display 58 in any appropriate manner, as discussed above.

In one manner of sheath detection, determining if an electrode has become sheathed can be based on an apparent determination that the electrode travels drastically further between two successive timesteps than it did between two or more previous timesteps. To make the determination, the PSU 40 can determine a vector relating to one or more electrodes for each incoming sample. A present vector, relating to the present time step, and all previous or selected number of time steps is recorded. If the present vector is significantly larger, such as at least a significance threshold, than a previous vector for a selected electrode, the selected electrode is marked as sheathed. It will be understood that any appropriate number of electrodes can be so tested and marked as sheathed or not. Generally, however, if at least one electrode of an instrument is determined to be sheathed then the entire instrument is marked as sheathed.

The significance threshold can be any selected and appropriate value. Also, the significance threshold can vary depending upon the size of previous vectors. Generally, a relationship of whether the present vector is significantly larger than the previous vector is inversely proportional to the magnitude of that vector. So if the vector is small then the value of the significance threshold has to be high; and if the vector is large, the significance threshold should be low. This is generally so because if the electrode is relatively still within the patient 26, there could be very little movement. Once the user moves the electrode, such as of the mapping catheter 100, the new motion could be magnitudes larger than previous motion, however it has not been sheathed. If the user is moving the electrode quickly and it becomes sheathed, then the amount of motion due to sheathing may not be much larger than the natural motion due to operation by the user.

In order to account for the relationship between the vector magnitude and the threshold, a determination can be made if the current distance traveled or vector magnitude is at least 4.5 times that of the previous movement or vector raised to the fourth power. In other words, if the magnitude of the previous vector of the electrode was determined to be 2 mm, which raised to the 4th power is 16 mm, and the current vector has a magnitude of 72 mm or more, then a determination that the electrode has become sheathed can be made by the PSU 40. Other appropriate thresholds could be selected, such as a multiplier of more or less than 4.5 or a power of more or less than 4.

Once it is determined that an electrode is sheathed, data collected is determined to be invalid. Valid data is not collected and used by the PSU 40 for mapping until the electrode is determined to be unsheathed. Once the PSU 40 determines that the electrode is sheathed the determination remains until an unsheathed determination is made. The sheathed determination is maintained until the electrode approaches a selected radius of the electrodes last known unsheathed location. In other words, when the electrode is determined to be near a point where the electrode was previously unsheathed it can be determined that the electrode has moved out of the sheath. This radius can grow over time in to compensate for natural movement which may occur as the electrode is sheathed.

In various manners, an electrode can be determined to be sheathed if two electrodes s are relatively close and on a rigid portion belonging to the same instrument, such as the lead or the mapping catheter 100, travel in very different directions. The two electrodes can be the tip and ring electrodes of the mapping catheter 100. The process for making the determination that two electrodes travel in significantly different directions can begin with determining the unit vector describing the direction of travel for the tip 108 and ring 110 electrodes. As discussed above, the ring electrode 110 is proximal and closer to the sheath 104 than the tip electrode 108. Initially, if the tip electrode 108 has moved a very small amount (e.g. less than about 2 mm, or less than about 1 mm), this process is deemed inaccurate as the determined motion could be due to noise in the PSU 40 system. Thus, the sheathed attribute for the ring electrode 110 is left unchanged by this process. If the determined movement of the tip electrode 108, however, is above the selected initial threshold then a dot-product is determined between the vectors of the tip electrode 108 and the ring electrode 110 to calculate the similarity in direction of travel. If the dot product is below a dot-product threshold then the ring electrode is marked as sheathed. The dot-product threshold can be selected by the user or automatically selected by and programmed into the PSU 40. For example, the dot-product threshold can be 0.25. It will also be understood that the instrument, such as the mapping catheter may include more than one ring electrode and, therefore, this process is repeated for each ring electrode.

Again, once an electrode has been marked as sheathed, it is not marked as unsheathed until an unsheathed occurrence is calculated. In this case, the electrode can be determined to be unsheathed if the tip-ring distance returns to some unsheathed factor of the last known good tip-ring distance. This unsheathed factor increases as time passes to account for non-linearities in the current fields generated in the patient 26 by the PSU 40, which may cause the tip-ring distance to naturally grow.

According to various manners, a determination that an electrode has become sheathed can be made if two electrodes belonging to the same instrument, such as the mapping catheter 100, travel significantly different amounts, e.g. past a movement significance threshold. To make the determination if the amount of movement is significantly different, the distances of travel for the tip and each ring electrode are determined. Again, if the tip has moved a very small amount, this process is deemed inaccurate as motion could be due to noise. Thus, the sheathed attribute for the ring electrode is left untouched by this test. Otherwise distances are compared to see if the ring electrode moved significantly further than the tip electrode.

The movement significance threshold can be selected by the user, automatically selected, or preselected. For example, the movement significance threshold can be a difference of three times. Thus, if the tip electrode is determined to have moved at least three times the distance of the ring electrode, the electrode can be marked as sheathed. Any appropriate movement significance threshold can be selected however, such as two times.

Again, once an electrode has been marked as sheathed, it is not marked as unsheathed until an unsheathed measurement is made. In this manner, the tip-ring distance is determined to have returned to some good distance unsheathed factor of the last known good tip-ring distance. This good distance unsheathed factor increase as time passes to account for non-linearities in the current fields generated in the patient 26 by the PSU 40, which may cause the tip-ring distance to naturally grow.

According to various manners, the electrode may have become sheathed if the inter-electrode spacing on a single instrument, such as the mapping catheter 100, has become significantly larger in an absolute sense or relative to prior samples. As discussed above, the position of the electrodes, such as the tip electrode 108 and the ring electrode 110 can be determined. Thus, a distance between them can also be determined. The distance between them can be an absolute value, such as 1 mm measured at any time in the patient 26, or a relative value when comparing two measurements. As discussed above, the distance between the tip and the ring electrodes, 108, 110 can be determined or corrected according to a tip-ring correction method. Determining the ring electrode is sheathed, however, can be an alternative determination as rather than simply correcting for distortions of the current fields in the patient 26 generated by the PSU 40.

The sheath detection method, can begin with determining and/or saving the distance between each electrode and its neighbor on the instrument. If the distance is above some absolute distance threshold then the proximal electrode (e.g. tip electrode 108) in the inter-electrode pair is marked as sheathed. This can be the absolute distance determination or portion of the sheathed determination process. The absolute distance threshold can be any appropriate distance, can be a known or initially measured distance. For example, it may be known that two electrodes are 5 mm apart. Thus, the absolute distance threshold can be 5 mm.

If the absolute distance threshold is not reached, the interelectrode spacing is compared to a previous sample to determine that a relative distance threshold has been reached. The previous sample could be an immediately previous sample or any appropriate previous sample. If the relative distance threshold is reached, then the proximal electrode in the pair is marked as sheathed.

The relative distance threshold can be any appropriate value. Generally, the significance of the relative distance threshold can relate to distance. The smaller the inter-electrode distance, the more it has to grow to be considered sheathed. Hence the relative distance threshold can be if the square of the current interelectrode distance is 2.5 times greater than the immediately previous interelectrode distance, the electrode can be marked as sheathed. For example, if the current interelectrode distance is 5 mm, its square is 25 mm. Thus, if the previous interelectrode distance is 10 mm or less than the electrode is marked as sheathed.

Again, the electrode is determined to remain sheathed until a measurement is made that the interelectrode distance has returned to some good interelectrode distance factor. The good interelectrode distance factor can be any appropriate factor, such as 1.1 times the last known good interelectrode distance. The last known good interelectrode distance can be the interelectrode distance measured immediately prior to the determination of sheathing.

Further, there is a finite distance that an electrode may travel within the heart 80 or vascular system. When past a finite distance, the electrode will run into an interior wall. Thus, if the PSU 40 tracks an electrode traveling at a relatively high velocity in a fairly uniform direction for several samples, then that electrode has likely become sheathed and is electrically immeasurable. The distance traveled can be dependent upon the known position of the electrode or previous known position of the electrode. For example, if it is known that the instrument was in a confined area, such as near the right ventricle apex, a short distance can be used as a threshold. Otherwise, any appropriate number of time samples, velocity, or distance can be used to determined that the electrode has become sheathed.

As discussed above, the most proximal electrode is nearest the sheath in any instrument, such as the ring electrode 110 being proximal on the mapping catheter 100 and nearest the sheath 104. Thus, generally, the proximal electrode may be the only electrode to have been sheathed. When marking the electrode as sheathed the entire instrument is marked as sheathed. When marked as sheathed, all position information during the time of marking as sheathed is determined to be invalid. Further, the PSU 40 can provide an indication to a user that the entire instrument is sheathed, such as a visual display on the display 58.

PSU Frequency Switching and Blocking

In addition to the various methods and procedures for determining valid an invalid data discussed above (e.g. sheath detection, tip-ring correction, etc.) others sources of interference or error can be detected by the PSU 40. The detection or correction of error can be based on hardware filters, processor determination, or other appropriate procedures. According to various embodiments, however, frequencies of current injected into the patient 26 for use other than by the PSU 40 may interfere with proper and correct functioning of the electrical feature used by the PSU 40 to determine a portion of the mapping instrument or other appropriate instrument.

Determination of biompedance and measurement of voltages can be in applications external to or in addition to the PSU 40. External examples of bioimedance include measuring hemodynamic performance, assuring patient electrode connection, and, other patient specific applications. In particular, the patient 26 may have a pacemaker implanted. If the patient 26 has an implanted pacemaker and is simultaneously undergoing a procedure utilizing the PSU 40, interference from the pacemaker may interfere with the PSU 40.

The PSU 40 injects a current through the patient 26, measures voltage between an electrode pair or pairs, and computes impedance. As discussed above the PSU 40 can injected current at any appropriate frequency or multiple frequencies for the different axis patch pairs. The frequencies are safely tolerated by the patient 26, efficient to detect, and provide high signal to noise characteristics. If signals are injected into the body, a system other than the PSU 40, also referred to as anomalous signals or currents, having may same or similar frequency as used by the PSU 40, the result in the fields being superimposed. If one system is in-band to another, interference can occur with misleading or distorted results to one or both systems. If interference occurs the anomalous signal or current, or non-PSU signal, can be an interfering signal or current.

Determination of whether an anomalous interfering signal is present can occur prior to initiation of position determination with the PSU 40. To detect if an interfering current or signal is present in the patient 26, the PSU 40 can perform an interference test that includes a signal generation and detection system and method. The interference test can include, prior to administration or injection of signals into the patient 26 by the PSU 40, determining whether interfering signals are present. If interfering signals are detected, the PSU 40 can then test detection of the electrodes of the instrument on an alternative, such as an adjacent, frequency. If the alternative frequency is clear, then the signal generator of the PSU 40 can be switched to the alternative frequency and the PSU 40 can then be used to determine a position of a position element, such as the electrodes 108, 110 of the mapping catheter 100. Accordingly, the PSU 40 can automatically detect whether an anomalous signal is an interfering signal based on in-band detection of a signal other than that generated by the PSU 40, whether the position information of the mapping catheter 100 is accurate, or other appropriate methods. The PSU 40 can also automatically switch to a frequency that is not interfered with by the anomalous signal.

A sampling system of the PSU 40 can be invoked to detect if an interfering signal interprets after a procedure with the PSU 40 begins. The sampling system can perform periodic interference checks to reveal if an interfering signal has appeared and switch frequencies in a manner transparent to the user 22. The sampling system of the PSU 40 can periodically cease signal generation to enable the detection circuits a period and freedom to sense an interfering signal and determine the frequency of the interfering signal. The periodic interference check can be manually initiated or automatic. When an interfering signal is detected a non-interfering frequency or channel can be selected for operation of the PSU 40. The PSU 40 can then be automatically or manually switched to a channel that would not be interfered with by the interfering signal. Having a wide selection of frequencies can allow concurrent operation.

The sampling system of the PSU 40 can include a system to switch frequencies for signal generation and detection. In the sampling system, signal generation can use tunable filters such that adjacent frequency operation is possible. In other words, once a signal frequency is detected that would interfere with the signal generation of the PSU 40 between the axis patches, the alternative frequency can be selected and generated between at least one pair of the axis patches for position determination by the PSU 40. It will also be understood, if an interfering signal is found or determined to exist the source of the signal could be blocked or eliminated. For example, an injected current form a pacemaker could be temporarily eliminated. This can occur in addition to or alternatively to changing a frequency.

Accordingly, the PSU 40 can be used to determine whether map data determined from the position element is valid or not. As discussed above, prior to initiation of a procedure with the PSU 40 or during a procedure with the PSU 40, interfering signal sampling can occur. If an interfering signal is found to be present certain map data can be marked as invalid and discarded or not used to generate the map data points 198 or the surface 241. The PSU 40 can also then switch to a non-interfering frequency, transparently to the user, to continue or begin map data collection.

Conclusion

The map of the patient 26, or any appropriate subject or feature, can be used as a graphical representation for navigation of an instrument, such as the lead 120, relative to a physical structure. The map displayed on the display 58 can be generated without the use of fluoroscopy or other imaging systems. Therefore, advantages of navigation, such as image-guided navigation, can be achieved without the need for an external imaging device. This can eliminate or reduce exposure of the user 22 to radiation and decrease procedure times by eliminating or reducing the necessity of requiring the acquisition of image data of the patient 26.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A method of determining a flow of a material in a volume of a patient, comprising:
   moving an instrument having a position element into the volume;
   evaluating an electrical property with the position element at a first time;
   determining a first position of the position element within the volume based on the evaluated electrical property at the first time;
   evaluating the electrical property with the position element at a second time later than the first time;
   determining a second position of the position element within the volume based on the evaluated electrical property at the second time;
   determining a change in position between the determined first position at the first time and the determined second position at the second time to determine a flow of material in the volume; and
   displaying a graphical representation of the determined change in position between the determined first position and the determined second position to illustrate a direction of the flow of material.

2. The method of claim 1, wherein determining a change in position includes determining a change in position between the determined first position at the first time and the determined second position at the second time to determine a flow of blood in a heart.

3. The method of claim 2, further comprising identifying congenital abnormalities based on the determined flow of blood in the heart.

4. The method of claim 2, further comprising determining a location of the coronary sinus ostium based on the determined flow of blood in the heart to determine a lead implantation site.

5. The method of claim 1, wherein displaying a graphical representation of the determined change in position includes:
   displaying a graphical representation of the first and second determined positions; and
   displaying an additional graphical representation indicative of the direction of the flow of material in the volume from the determined first position to the determined second position.

6. The method of claim 5, wherein displaying the additional graphical representation indicative of direction includes displaying an arrow pointing from the determined first position to the determined second position.

7. The method of claim 1, wherein moving the position element into the volume includes:
   fixing a proximal end of the instrument;
   placing the position element in contact with a conductive medium in the volume; and
   allowing the position element to move in a flow of material within the volume relative to the fixed proximal end of the instrument.

8. The method of claim 7, further comprising:
   providing three sets of axis generation electrodes on an exterior surface of the volume, each set of electrodes spaced apart and arranged to establish an axis via a conductive path therebetween, each axis of the three sets of electrodes being substantially orthogonal to each other and intersecting at a common point;
   injecting a current into the volume between each set of electrodes and generating a voltage gradient in the volume between each set of electrodes;
   wherein evaluating the electrical properties includes sensing voltage at the position element between each set of electrodes at the first time and the second time;
   wherein determining the first position of the position element includes determining a position of the sensed voltage of the electrical property at the first time along the voltage gradients between each of the three sets of electrodes so as to provide a determined three dimensional first position of the position element; and
   wherein determining the second position of the position element includes determining a position of the sensed voltage of the electrical property at the second time along the voltage gradients between each of the three sets of electrodes so as to provide a determined three dimensional second position of the position element.

9. The method of claim 8, further comprising determining a rate of movement of the position element from the determined first position to the determined second position at least by determining a distance between the determined first and second positions and an elapsed amount of time between determining the first position at the first time and determining the second position at the second time.

10. The method of claim 8, wherein displaying a graphical representation of the determined change in position includes:
    displaying a graphical representation of the first and second determined positions; and
    displaying an additional graphical representation indicative of a direction of flow of the material in the volume from the determined first position towards the determined second position.

11. The method of claim 1, further comprising providing a selectively inflatable member on a portion of the instrument arranged to be moved into the volume, and wherein the selectively inflatable member is arranged to be inflated prior to determining the first and second positions with the position element to cause a drag to facilitate determining flow direction.

12. The method of claim 1, further comprising:
    providing a selectively inflatable member on a portion of the instrument arranged to be moved into the volume; and
    inflating the inflatable member after determining the first position at the first time and prior to determining the second position at the second time with the position element.

13. The method of claim 1, further comprising:
    providing map data of at least a portion of an inner surface of the volume; and
    wherein determining a change in position between the first and second determined positions includes:
        determining a first distance between the first determined position and a point from the surface map data;
        determining a second distance between the second determined position and the point from the surface map data; and
        determining a difference between the determined first and second distances.

14. The method of claim 13, wherein displaying the graphical representation of the determined change in position includes displaying a graphical representation indicative of a movement from the determined first position to the determined second position.

15. The method of claim 13, wherein displaying a graphical representation of the determined change in position includes:
    displaying a graphical representation of the first and second determined positions; and
    displaying an additional graphical representation indicative of the direction of the flow of material in the volume from the determined first position to the determined second position.

16. The method of claim 1, further comprising:
    tracking map positions of a map position element on a mapping instrument in the volume;
    collecting the map positions of the map position element;
    determining a validity of the at least the collected map positions;
    generating a map based on at least the map collected positions;
    displaying the map on a display device;
    measuring a rhythmic feature of a volume;
    wherein tracking the position element, includes at least one of:
    selecting between a uni-polar and bi-polar collection of map positions;
    determining whether an interfering frequency is present during or prior to map collecting the positions;
    inflating a portion of the mapping instrument;
    fixing a location of the first position element relative to the second position element;
    moving a flexible member with the first position element relative to the second position element at the fixed location and measuring the position of the first member position element relative to the second position element;
    measuring a temperature within the volume with at least one of the map position element, the first position element, and the second position element; and
    displaying on a display device at least one of:
    a corrected map data, wherein the corrected map data is generated by reducing distortion of a measured position of a mapping instrument by determining a scaling factor between two position elements of the mapping instrument;
    a pseudo location of an axis electrode relative to the map;
    a location of a reference electrode relative to the map;
    a location of a feature determined by generating a filled volume and determining curvilinear portions to be displayed relative to the filled volume with the mapping instrument;
    a map point determined by generating a virtual point based on a known position of a physical portion of the mapping instrument relative to a position element of the mapping instrument;
    a map based on locations categorized relative to the measured rhythmic feature;
    a virtual map data point determined based on a geometry of the mapping instrument relative to the position element;
    a location of an introducer through which the mapping instrument or the procedure instrument is passed;
    an augmented generated map to include a virtual filled volume to illustrate three dimensional features located in a physical space on the generated virtual filled volume;
    a displayed representation of a temperature at a sub-plurality of locations in the generated map;
    a generated plurality of maps wherein at least one map of the generated plurality of maps of the volume is based on a portion of a heart rhythm and displaying the plurality of maps in time order; and
    generated maps that include a first map based only on a collected plurality of data categorized in a category and a second map based only on the collected plurality of data categorized in a second category.

17. A method of determining a flow of a material in a volume of a patient, comprising:
    providing an instrument having a position element on an exterior of a first portion of the instrument arranged to be moved into the volume;
    moving the first portion of the instrument into the volume and placing the position element in contact with a flowing conductive medium in the volume;
    fixing a second portion of the instrument relative to the first portion;
    providing three sets of axis generation electrodes on an exterior surface of the volume, each set of electrodes spaced apart and arranged to establish an axis via a conductive path therebetween, each axis of the three sets of electrodes being substantially orthogonal to each other and intersecting at a common point;
    injecting a current into the volume between each set of electrodes and generating a voltage gradient in the volume between each set of electrodes;
    sensing a first voltage at the position element between each set of the three sets of electrodes at a first time;
    determining a first position of the position element based on the sensed first voltage along the voltage gradients of each of the three sets of electrodes so as to provide a determined three dimensional first position of the position element at the first time;

sensing a second voltage at the position element between each set of the three sets of electrodes at a second time later than the first time;

determining a second position of the position element based on the sensed second voltage along the voltage gradients of each of the three sets of electrodes so as to provide a determined three dimensional second position of the position element at the second time;

determining a change in position between the determined first and second positions of the position element; and displaying a graphical representation of the determined change in position between the first and second determined positions that indicates a direction of flow of the conductive medium in the volume from the first to the second determined position.

18. The method of claim 17, further comprising providing a selectively inflatable member on the portion of the instrument arranged to be moved into the volume, and wherein the selectively inflatable member is arranged to be inflated prior to determining the first and second positions of the position element to cause a drag to facilitate determining flow direction.

19. The method of claim 17, further comprising determining a rate of movement of the position element from the determined first position to the determined second position at least by determining a distance between the determined first and second positions and an elapsed amount of time between determining the first position and determining the second position.

20. The method of claim 17, wherein fixing a second portion of the instrument relative to the first portion includes holding static the second portion of the instrument arranged to remain outside the volume after moving the first portion of the instrument into the volume.

21. A system for determining a flow of material in a volume of a heart of a patient, comprising:

an instrument having a position element and a selectively inflatable member each positioned on a portion of the instrument arranged to be moved into the volume so as to place the inflatable member and the position element in contact with a flowing conductive medium in the volume;

a position sensing unit having at least one set of axis generation electrodes to inject a current into the volume, the at least one set of electrodes adapted to be positioned on an outer surface of the volume to establish an axis via a conductive path therebetween, the injected current generating a voltage gradient in the volume between the at least one set of electrodes;

a display device; and a processor coupled to the position element, the position sensing unit and the display device;

wherein the position element is arranged to sense a first voltage and a second voltage along the voltage gradient between the at least one set of electrodes and communicate the sensed first and second voltages to the processor, the processor is arranged to determine respective first and second positions of the position element based on the first and second sensed voltages along the voltage gradient and to determine a change in position of the position element between the determined first and second positions to determine a flow of material in the volume;

wherein the display device is arranged to display a graphical representation of the flow of material in the volume between the determined first and second positions.

22. The system of claim 21, wherein the processor is further arranged to determine a rate of movement of the position element from the determined first position to the determined second position at least by determining a distance between the determined first and second positions and an elapsed amount of time between determining the first position and determining the second position.

23. The system of claim 21, wherein the processor is arranged to determine the flow of material in the volume using only the instrument and the position sensing unit.

24. The system of claim 21, further comprising:

a display processor operable to augment a map based at least on the determined position of a mapping instrument map on the display device, wherein the display processor is operable to at least one of:

determine a position of the position element that is positioned to sense a voltage formed in the volume;

determine a position of an input impedance reference electrode and display it on the display device relative to the map; and determine a pseudo position of the axis generation electrodes on the display device relative to the map;

a physiological measuring device;

an introducer operable to be located with the position determination processor;

a reference electrode at a fixed position on a surface of the volume and the position determination processor operable to determine the location of the reference electrode; and a procedure instrument with a second position element operable to be located relative to the map;

wherein the instrument having a position element and operable to be located in volume the further includes at least one of: an inflatable portion, at least two electrodes as the first position element, a guidewire operable to be positioned through a cannula, a plurality of the position elements along a length of the instrument, and a temperature sensor;

wherein displayed map point positions in the map on the display device for visualization by a user is based on determined positions of one or more of the position elements wherein the instrument includes a catheter having an opening in a sidewall of the catheter operable to allow a fluid into an interior of the catheter and a catheter cover operable to selectively cover the opening in the sidewall of the catheter, wherein the procedure instrument is operable to be moved within the catheter;

wherein the position determination processor is operable to determine the location of a sensed temperature with the temperature sensor and the display processor is operable to generate an icon representative of both temperature and position for display on the display device or change map color in a region as a function of temperature.

* * * * *